United States Patent
Fangrow, Jr.

(10) Patent No.: US 8,262,628 B2
(45) Date of Patent: *Sep. 11, 2012

(54) MEDICAL CONNECTOR WITH CLOSEABLE MALE LUER

(75) Inventor: Thomas F. Fangrow, Jr., Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/892,744

(22) Filed: Sep. 28, 2010

(65) Prior Publication Data

US 2011/0015581 A1   Jan. 20, 2011

Related U.S. Application Data

(63) Continuation of application No. 11/417,604, filed on May 3, 2006, now Pat. No. 7,803,139.

(60) Provisional application No. 60/696,894, filed on Jul. 6, 2005, provisional application No. 60/707,319, filed on Aug. 11, 2005.

(51) Int. Cl.
*A61M 5/00* (2006.01)

(52) U.S. Cl. ........................................ 604/246

(58) Field of Classification Search .......... 604/246, 604/249, 256; 251/149
See application file for complete search history.

(56) References Cited

U.S. PATENT DOCUMENTS 2,842,382 A * 7/1958 Franck ................ 251/149.4

(Continued)

FOREIGN PATENT DOCUMENTS

EP  0 791 371 A1  8/1997

(Continued)

OTHER PUBLICATIONS

U.S. Appl. No. 11/417,923, filed May 3, 2006, and its prosecution history, including office communications, amendments, remarks, and other potentially relevant documents, Gustus et al.

(Continued)

*Primary Examiner* — Nicholas D Lucchesi
*Assistant Examiner* — Aarti B Berdichevsky
(74) *Attorney, Agent, or Firm* — Knobbe, Martens, Olson & Bear LLP

(57) ABSTRACT

A luer connector comprising a housing with a hollow bore having first and second ends. The hollow bore also has a male luer tip and a tapering interior surface. The luer connector also comprises a rigid valve member configured to at least partially extend through the housing. The valve member has a first opened end and a second closed end. The valve member also comprises a passageway within the valve member and an outwardly extending flange near the second end adapted to seal the hollow bore at the second end of the housing when placed in contact with a tapering interior surface of the housing. The valve member further comprises at least one opening near the closed end of the valve member extending outward from the passageway through the valve member and at least one strut attached to the valve member. At least a portion of the strut extends substantially parallel to the central axis of the valve member. The luer connector also comprises a retaining member configured to couple the valve member and the housing and a sealing element disposed within the housing. The sealing element is configured to inhibit fluid communication through the hollow bore of the housing between the interior of the male luer tip of the housing and the first end of the housing.

33 Claims, 32 Drawing Sheets

U.S. PATENT DOCUMENTS

| | | | | |
|---|---|---|---|---|
| 2,931,668 | A | | 4/1960 | Baley |
| 2,968,497 | A | * | 1/1961 | Treleman .................. 251/149.4 |
| 3,127,892 | A | * | 4/1964 | Bellamy, Jr. et al. ........... 604/408 |
| 3,304,047 | A | * | 2/1967 | Martin .......................... 251/118 |
| 3,334,860 | A | * | 8/1967 | Bolton, Jr. ................. 251/149.1 |
| 3,707,972 | A | * | 1/1973 | Villari et al. .................. 604/249 |
| 3,729,031 | A | * | 4/1973 | Baldwin .......................... 141/2 |
| 3,986,508 | A | | 10/1976 | Barrington |
| 4,055,179 | A | * | 10/1977 | Manschot et al. ............ 604/322 |
| 4,066,067 | A | * | 1/1978 | Micheli .......................... 600/577 |
| 4,076,285 | A | * | 2/1978 | Martinez ....................... 285/332 |
| 4,080,965 | A | | 3/1978 | Phillips |
| 4,121,585 | A | * | 10/1978 | Becker, Jr. ...................... 604/86 |
| 4,133,441 | A | * | 1/1979 | Mittleman et al. ........... 215/247 |
| 4,143,853 | A | * | 3/1979 | Abramson ................. 251/149.1 |
| 4,150,845 | A | * | 4/1979 | Riuli et al. ...................... 285/81 |
| 4,195,632 | A | * | 4/1980 | Parker et al. .................. 604/411 |
| 4,233,982 | A | * | 11/1980 | Bauer et al. .................. 604/256 |
| 4,245,635 | A | * | 1/1981 | Kontos ..................... 604/167.03 |
| 4,324,239 | A | * | 4/1982 | Gordon et al. ................ 604/122 |
| 4,334,551 | A | * | 6/1982 | Pfister ........................ 137/614.03 |
| 4,340,049 | A | * | 7/1982 | Munsch .......................... 604/29 |
| 4,379,458 | A | * | 4/1983 | Bauer et al. .................. 604/264 |
| 4,387,879 | A | * | 6/1983 | Tauschinski ............. 251/149.1 |
| 4,397,442 | A | * | 8/1983 | Larkin .......................... 251/342 |
| 4,430,073 | A | * | 2/1984 | Bemis et al. .................. 604/119 |
| 4,436,125 | A | * | 3/1984 | Blenkush ...................... 141/330 |
| 4,457,749 | A | * | 7/1984 | Bellotti et al. .................. 604/29 |
| 4,511,359 | A | * | 4/1985 | Vaillancourt ................. 604/411 |
| 4,538,836 | A | * | 9/1985 | Krutten ........................ 285/24 |
| 4,610,469 | A | * | 9/1986 | Wolff-Mooij ................ 285/260 |
| 4,619,640 | A | * | 10/1986 | Potolsky et al. .................. 604/7 |
| 4,623,332 | A | * | 11/1986 | Lindmayer et al. ............ 604/68 |
| 4,629,159 | A | * | 12/1986 | Wellenstam ............... 251/149.6 |
| 4,660,803 | A | * | 4/1987 | Johnston et al. ........... 251/149.1 |
| 4,662,878 | A | * | 5/1987 | Lindmayer .................. 604/411 |
| 4,700,744 | A | * | 10/1987 | Rutter et al. .............. 137/614.04 |
| 4,723,603 | A | * | 2/1988 | Plummer ....................... 166/275 |
| 4,728,075 | A | * | 3/1988 | Paradis ......................... 251/122 |
| 4,745,950 | A | * | 5/1988 | Mathieu ..................... 137/798 |
| 4,771,964 | A | * | 9/1988 | Watanabe et al. ............ 242/250 |
| 4,774,965 | A | * | 10/1988 | Rodriguez et al. ........... 600/584 |
| 4,781,702 | A | * | 11/1988 | Herrli ............................ 604/244 |
| 4,804,015 | A | * | 2/1989 | Albinsson ................ 137/614.03 |
| 4,816,024 | A | * | 3/1989 | Sitar et al. ...................... 604/192 |
| 4,834,271 | A | * | 5/1989 | Litwin .......................... 222/511 |
| 4,862,913 | A | * | 9/1989 | Wildfang .................... 137/543 |
| 4,883,483 | A | * | 11/1989 | Lindmayer .................. 604/411 |
| 4,915,687 | A | * | 4/1990 | Sivert ............................ 604/83 |
| 4,917,669 | A | * | 4/1990 | Bonaldo ....................... 604/192 |
| 4,935,010 | A | * | 6/1990 | Cox et al. ..................... 604/122 |
| 4,950,260 | A | * | 8/1990 | Bonaldo ....................... 604/535 |
| D313,277 | S | | 12/1990 | Haining ....................... D24/129 |
| D314,050 | S | * | 1/1991 | Sone ........................... D24/129 |
| 5,006,114 | A | * | 4/1991 | Rogers et al. ................. 604/245 |
| 5,021,059 | A | * | 6/1991 | Kensey et al. ................. 606/213 |
| 5,047,021 | A | * | 9/1991 | Utterberg .................... 604/533 |
| 5,065,783 | A | * | 11/1991 | Ogle, II ...................... 137/68.11 |
| 5,070,885 | A | * | 12/1991 | Bonaldo ....................... 600/576 |
| 5,098,385 | A | * | 3/1992 | Walsh ........................... 604/131 |
| 5,108,376 | A | * | 4/1992 | Bonaldo ....................... 604/171 |
| 5,122,123 | A | * | 6/1992 | Vaillancourt ................. 604/192 |
| 5,139,483 | A | * | 8/1992 | Ryan ............................. 604/86 |
| 5,147,333 | A | * | 9/1992 | Raines .......................... 604/249 |
| 5,154,703 | A | * | 10/1992 | Bonaldo ....................... 604/244 |
| RE34,223 | E | * | 4/1993 | Bonaldo ....................... 604/192 |
| 5,199,948 | A | * | 4/1993 | McPhee ......................... 604/86 |
| 5,201,725 | A | * | 4/1993 | Kling ............................ 604/284 |
| 5,203,775 | A | * | 4/1993 | Frank et al. .................. 604/256 |
| 5,211,634 | A | * | 5/1993 | Vaillancourt ............ 604/167.02 |
| 5,215,537 | A | * | 6/1993 | Lynn et al. .................... 604/244 |
| 5,215,538 | A | | 6/1993 | Larkin |
| 5,242,393 | A | | 9/1993 | Brimhall et al. |
| 5,242,425 | A | * | 9/1993 | White et al. .................. 604/256 |
| 5,251,873 | A | * | 10/1993 | Atkinson et al. ........... 251/149.1 |
| 5,269,771 | A | * | 12/1993 | Thomas et al. ............... 604/539 |
| 5,273,533 | A | | 12/1993 | Bonaldo |
| 5,279,571 | A | | 1/1994 | Larkin |
| 5,281,206 | A | * | 1/1994 | Lopez ........................... 604/533 |
| 5,284,475 | A | * | 2/1994 | Mackal ......................... 604/247 |
| 5,295,657 | A | * | 3/1994 | Atkinson .................. 251/149.1 |
| 5,301,686 | A | * | 4/1994 | Newman ....................... 600/573 |
| 5,306,243 | A | * | 4/1994 | Bonaldo .......................... 604/86 |
| 5,312,377 | A | * | 5/1994 | Dalton .......................... 604/534 |
| 5,324,270 | A | * | 6/1994 | Kayan et al. ............ 604/167.03 |
| 5,330,450 | A | * | 7/1994 | Lopez ........................... 604/533 |
| 5,334,159 | A | | 8/1994 | Turkel |
| 5,334,414 | A | * | 8/1994 | Edie et al. ..................... 427/189 |
| 5,360,413 | A | * | 11/1994 | Leason et al. ................. 604/249 |
| 5,370,636 | A | * | 12/1994 | Von Witzleben ............. 604/535 |
| 5,380,306 | A | * | 1/1995 | Brinon .......................... 604/244 |
| 5,385,372 | A | | 1/1995 | Utterberg |
| 5,390,898 | A | | 2/1995 | Smedley et al. |
| 5,391,150 | A | * | 2/1995 | Richmond .................... 604/111 |
| 5,395,348 | A | | 3/1995 | Ryan |
| 5,397,314 | A | | 3/1995 | Farley et al. |
| 5,400,500 | A | | 3/1995 | Behnke et al. |
| 5,401,245 | A | | 3/1995 | Haining |
| 5,402,826 | A | * | 4/1995 | Molnar et al. ........... 137/614.01 |
| 5,402,982 | A | | 4/1995 | Atkinson et al. |
| 5,405,323 | A | | 4/1995 | Rogers et al. |
| 5,405,331 | A | * | 4/1995 | Behnke et al. .......... 604/167.02 |
| 5,405,333 | A | * | 4/1995 | Richmond .................... 604/257 |
| 5,411,499 | A | * | 5/1995 | Dudar et al. .................. 604/411 |
| 5,417,673 | A | * | 5/1995 | Gordon ......................... 604/539 |
| 5,423,791 | A | | 6/1995 | Bartlett |
| 5,425,465 | A | * | 6/1995 | Healy ............................ 215/355 |
| 5,433,330 | A | * | 7/1995 | Yatsko et al. .................. 215/247 |
| 5,439,451 | A | * | 8/1995 | Collinson et al. ............. 604/247 |
| 5,441,487 | A | * | 8/1995 | Vedder ..................... 604/167.03 |
| 5,445,623 | A | * | 8/1995 | Richmond .................... 604/251 |
| 5,456,668 | A | * | 10/1995 | Ogle, II ........................ 604/110 |
| 5,456,675 | A | * | 10/1995 | Wolbring et al. ............. 604/537 |
| 5,464,399 | A | * | 11/1995 | Boettger ....................... 604/533 |
| 5,470,319 | A | | 11/1995 | Mayer |
| 5,470,327 | A | * | 11/1995 | Helgren et al. ................ 604/411 |
| 5,474,536 | A | * | 12/1995 | Bonaldo .......................... 604/86 |
| 5,480,393 | A | * | 1/1996 | Bommarito .................. 604/523 |
| 5,492,147 | A | * | 2/1996 | Challender et al. ...... 137/614.05 |
| 5,501,426 | A | * | 3/1996 | Atkinson et al. ........... 251/149.1 |
| 5,507,744 | A | * | 4/1996 | Tay et al. ......................... 606/50 |
| 5,514,177 | A | * | 5/1996 | Kurz et al. ...................... 623/10 |
| 5,518,026 | A | * | 5/1996 | Benjey ..................... 137/512.15 |
| 5,520,665 | A | * | 5/1996 | Fleetwood .................... 604/537 |
| 5,520,666 | A | * | 5/1996 | Choudhury et al. .......... 604/537 |
| 5,527,284 | A | | 6/1996 | Ohnemus et al. |
| 5,533,708 | A | * | 7/1996 | Atkinson et al. ........... 251/149.1 |
| 5,533,983 | A | * | 7/1996 | Haining ........................ 604/249 |
| 5,535,785 | A | * | 7/1996 | Werge et al. .................. 137/843 |
| 5,540,661 | A | * | 7/1996 | Tomisaka et al. ............. 604/265 |
| 5,549,566 | A | * | 8/1996 | Elias et al. ................ 604/167.03 |
| 5,549,577 | A | | 8/1996 | Siegel et al. |
| 5,549,651 | A | * | 8/1996 | Lynn ............................. 604/537 |
| 5,552,118 | A | * | 9/1996 | Mayer ........................... 422/565 |
| 5,555,908 | A | * | 9/1996 | Edwards et al. ........... 137/329.1 |
| 5,569,235 | A | * | 10/1996 | Ross et al. ..................... 604/403 |
| 5,573,516 | A | * | 11/1996 | Tyner ............................ 604/249 |
| 5,575,769 | A | * | 11/1996 | Vaillancourt .................... 604/86 |
| 5,578,059 | A | * | 11/1996 | Patzer ........................... 604/249 |
| 5,584,819 | A | * | 12/1996 | Kopfer ......................... 604/239 |
| 5,591,137 | A | * | 1/1997 | Stevens ......................... 604/296 |
| 5,591,143 | A | * | 1/1997 | Trombley et al. ............. 604/534 |
| 5,597,536 | A | * | 1/1997 | Mayer ........................... 422/565 |
| 5,616,129 | A | | 4/1997 | Mayer |
| 5,616,130 | A | * | 4/1997 | Mayer ..................... 604/167.02 |
| RE35,539 | E | * | 6/1997 | Bonaldo ....................... 600/573 |
| 5,643,224 | A | | 7/1997 | Szapiro et al. |
| 5,645,538 | A | * | 7/1997 | Richmond .................... 604/256 |
| 5,674,206 | A | * | 10/1997 | Allton et al. .................. 604/249 |
| 5,676,346 | A | * | 10/1997 | Leinsing ................... 251/149.1 |
| 5,685,866 | A | | 11/1997 | Lopez |
| 5,685,868 | A | * | 11/1997 | Lundquist ..................... 604/523 |
| 5,699,821 | A | * | 12/1997 | Paradis ............................. 137/1 |
| 5,700,248 | A | * | 12/1997 | Lopez ........................... 604/249 |
| 5,702,374 | A | | 12/1997 | Johnson |
| 5,735,826 | A | * | 4/1998 | Richmond .................... 604/251 |
| 5,738,144 | A | * | 4/1998 | Rogers ...................... 137/614.03 |

| | | | |
|---|---|---|---|
| 5,749,861 A * | 5/1998 | Guala et al. ............... 604/249 |
| RE35,841 E | 7/1998 | Frank et al. |
| 5,782,816 A * | 7/1998 | Werschmidt et al. ......... 604/256 |
| 5,785,693 A * | 7/1998 | Haining ..................... 604/249 |
| 5,806,831 A * | 9/1998 | Paradis ..................... 251/149.1 |
| 5,814,024 A * | 9/1998 | Thompson et al. ........... 604/246 |
| 5,820,601 A * | 10/1998 | Mayer ..................... 604/167.02 |
| 5,839,715 A * | 11/1998 | Leinsing ..................... 251/149.1 |
| 5,848,994 A * | 12/1998 | Richmond ..................... 604/248 |
| 5,947,954 A * | 9/1999 | Bonaldo ..................... 604/533 |
| 6,029,946 A * | 2/2000 | Doyle ..................... 251/149.1 |
| 6,036,171 A * | 3/2000 | Weinheimer et al. ...... 251/149.1 |
| 6,050,978 A * | 4/2000 | Orr et al. ..................... 604/249 |
| 6,063,062 A * | 5/2000 | Paradis ..................... 604/249 |
| 6,068,011 A * | 5/2000 | Paradis ..................... 137/1 |
| 6,068,617 A * | 5/2000 | Richmond ..................... 604/255 |
| 6,079,432 A * | 6/2000 | Paradis ..................... 137/1 |
| 6,106,502 A * | 8/2000 | Richmond ..................... 604/246 |
| 6,113,068 A * | 9/2000 | Ryan ..................... 251/149.4 |
| 6,142,446 A * | 11/2000 | Leinsing ..................... 251/149.1 |
| 6,152,913 A * | 11/2000 | Feith et al. ..................... 604/533 |
| 6,206,860 B1 * | 3/2001 | Richmond ..................... 604/246 |
| 6,224,578 B1 | 5/2001 | Davis et al. |
| 6,242,393 B1 * | 6/2001 | Ishida et al. ..................... 508/462 |
| 6,245,048 B1 * | 6/2001 | Fangrow et al. ............. 604/249 |
| 6,290,206 B1 | 9/2001 | Doyle |
| 6,299,132 B1 * | 10/2001 | Weinheimer et al. ...... 251/149.6 |
| 6,428,520 B1 * | 8/2002 | Lopez et al. ..................... 604/249 |
| 6,431,219 B1 | 8/2002 | Redler et al. |
| 6,485,472 B1 | 11/2002 | Richmond |
| 6,499,719 B1 * | 12/2002 | Clancy et al. ..................... 251/149.6 |
| 6,508,792 B2 * | 1/2003 | Szames et al. ............... 604/237 |
| 6,508,807 B1 | 1/2003 | Peters |
| 6,541,802 B2 | 4/2003 | Doyle |
| 6,543,745 B1 * | 4/2003 | Enerson ..................... 251/149.7 |
| 6,581,906 B2 * | 6/2003 | Pott et al. ..................... 251/149.1 |
| 6,585,229 B2 | 7/2003 | Cote et al. |
| 6,595,964 B2 * | 7/2003 | Finley et al. ..................... 604/246 |
| 6,595,981 B2 * | 7/2003 | Huet ..................... 604/523 |
| 6,609,696 B2 * | 8/2003 | Enerson ..................... 251/86 |
| 6,666,852 B2 * | 12/2003 | Niedospial, Jr. ............. 604/415 |
| 6,695,817 B1 * | 2/2004 | Fangrow, Jr. ............. 604/167.01 |
| 6,745,998 B2 * | 6/2004 | Doyle ..................... 251/149.6 |
| 6,840,501 B2 | 1/2005 | Doyle |
| 6,875,205 B2 | 4/2005 | Leinsing |
| 6,899,315 B2 * | 5/2005 | Maiville et al. ............. 251/149.4 |
| 6,955,669 B2 * | 10/2005 | Curutcharry ..................... 604/415 |
| 6,964,406 B2 * | 11/2005 | Doyle ..................... 251/149.6 |
| 7,004,934 B2 * | 2/2006 | Vaillancourt ..................... 604/533 |
| 7,037,302 B2 * | 5/2006 | Vaillancourt et al. ......... 604/533 |
| 7,040,598 B2 * | 5/2006 | Raybuck ..................... 251/149.1 |
| 7,044,441 B2 * | 5/2006 | Doyle ..................... 251/149.6 |
| 7,100,891 B2 * | 9/2006 | Doyle ..................... 251/149.6 |
| 7,125,396 B2 * | 10/2006 | Leinsing et al. ......... 604/167.03 |
| 7,140,592 B2 * | 11/2006 | Phillips ..................... 251/149.6 |
| 7,182,313 B2 * | 2/2007 | Doyle ..................... 251/149.6 |
| 7,195,228 B2 | 3/2007 | Tiberghien et al. |
| 7,244,249 B2 * | 7/2007 | Leinsing et al. ............. 604/500 |
| 7,306,197 B2 * | 12/2007 | Parrino et al. ............. 251/149.6 |
| 7,306,198 B2 * | 12/2007 | Doyle ..................... 251/149.6 |
| 7,306,566 B2 * | 12/2007 | Raybuck ..................... 600/576 |
| 7,347,458 B2 * | 3/2008 | Rome et al. ..................... 285/384 |
| 7,350,764 B2 | 4/2008 | Raybuck |
| 7,361,164 B2 * | 4/2008 | Simpson et al. ............. 604/236 |
| 7,497,484 B2 * | 3/2009 | Ziman ..................... 285/402 |
| 7,559,530 B2 | 7/2009 | Korogi et al. |
| 7,588,563 B2 * | 9/2009 | Guala ..................... 604/535 |
| 7,645,274 B2 | 1/2010 | Whitley |
| 7,651,481 B2 | 1/2010 | Raybuck |
| 7,666,170 B2 * | 2/2010 | Guala ..................... 604/249 |
| 7,758,566 B2 | 7/2010 | Simpson et al. |
| 7,766,304 B2 | 8/2010 | Phillips |
| 7,766,897 B2 | 8/2010 | Ramsey et al. |
| 7,803,139 B2 * | 9/2010 | Fangrow, Jr. ..................... 604/256 |
| 7,803,140 B2 | 9/2010 | Fangrow, Jr. |
| 7,815,614 B2 | 10/2010 | Fangrow, Jr. |
| 7,857,805 B2 | 12/2010 | Raines |
| 7,976,532 B2 | 7/2011 | Kitani et al. |
| 7,998,134 B2 | 8/2011 | Fangrow et al. |
| 8,066,692 B2 | 11/2011 | Simpson et al. |
| 2001/0045539 A1* | 11/2001 | Doyle ..................... 251/149.1 |
| 2002/0104574 A1* | 8/2002 | Redler et al. ..................... 138/137 |
| 2003/0136932 A1* | 7/2003 | Doyle ..................... 251/149.1 |
| 2003/0153895 A1* | 8/2003 | Leinsing ..................... 604/403 |
| 2003/0183795 A1* | 10/2003 | Doyle ..................... 251/149.1 |
| 2003/0208165 A1* | 11/2003 | Christensen et al. ......... 604/256 |
| 2003/0209681 A1* | 11/2003 | Leinsing et al. ............. 251/149.1 |
| 2004/0124388 A1 | 7/2004 | Kiehne |
| 2004/0124389 A1* | 7/2004 | Phillips ..................... 251/149.4 |
| 2004/0227120 A1* | 11/2004 | Raybuck ..................... 251/149.1 |
| 2005/0015075 A1* | 1/2005 | Wright et al. ..................... 604/535 |
| 2005/0124942 A1* | 6/2005 | Richmond ..................... 604/246 |
| 2005/0228362 A1* | 10/2005 | Vaillancourt ..................... 604/533 |
| 2006/0058734 A1* | 3/2006 | Phillips ..................... 604/93.01 |
| 2006/0058773 A1* | 3/2006 | Raybuck ..................... 604/403 |
| 2006/0065873 A1* | 3/2006 | Doyle ..................... 251/149.1 |
| 2006/0129109 A1* | 6/2006 | Shaw et al. ..................... 604/246 |
| 2006/0142730 A1* | 6/2006 | Proulx et al. ..................... 604/403 |
| 2006/0142735 A1* | 6/2006 | Whitley ..................... 604/537 |
| 2006/0149213 A1* | 7/2006 | Raybuck ..................... 604/500 |
| 2006/0161115 A1* | 7/2006 | Fangrow ..................... 604/249 |
| 2006/0163514 A1* | 7/2006 | Doyle ..................... 251/149.1 |
| 2006/0202146 A1* | 9/2006 | Doyle ..................... 251/149.1 |
| 2006/0208210 A1* | 9/2006 | Raybuck ..................... 251/149.1 |
| 2006/0253084 A1* | 11/2006 | Nordgren ..................... 604/247 |
| 2007/0017583 A1* | 1/2007 | Fangrow, Jr. ............. 137/614.06 |
| 2007/0043334 A1* | 2/2007 | Guala ..................... 604/533 |
| 2007/0073270 A1* | 3/2007 | Christensen et al. ......... 604/533 |
| 2007/0088292 A1* | 4/2007 | Fangrow, Jr. ..................... 604/246 |
| 2007/0088293 A1* | 4/2007 | Fangrow, Jr. ..................... 604/246 |
| 2007/0088294 A1* | 4/2007 | Fangrow, Jr. ..................... 604/246 |
| 2007/0088324 A1* | 4/2007 | Fangrow, Jr. ..................... 604/533 |
| 2007/0088325 A1* | 4/2007 | Fangrow, Jr. ..................... 604/533 |
| 2007/0088327 A1* | 4/2007 | Guala ..................... 604/533 |
| 2007/0120083 A1* | 5/2007 | Simpson et al. ............. 251/149.6 |
| 2007/0179453 A1* | 8/2007 | Lim et al. ..................... 604/218 |
| 2008/0103485 A1* | 5/2008 | Kruger ..................... 604/533 |
| 2008/0190485 A1* | 8/2008 | Guala ..................... 137/1 |
| 2008/0287920 A1* | 11/2008 | Fangrow et al. ............. 604/535 |
| 2010/0174242 A1 | 7/2010 | Anderson et al. |
| 2010/0256574 A1 | 10/2010 | Simpson et al. |
| 2011/0015581 A1* | 1/2011 | Fangrow, Jr. ..................... 604/246 |
| 2011/0015582 A1 | 1/2011 | Fangrow, Jr. |
| 2011/0276035 A1 | 11/2011 | Fangrow, Jr. |

FOREIGN PATENT DOCUMENTS

| | | |
|---|---|---|
| GB | 2 353 078 | 2/2001 |
| WO | WO 01/03756 | 1/2001 |

OTHER PUBLICATIONS

U.S. Appl. No. 11/417,671, filed May 3, 2006, and its prosecution history, including office communications, amendments, remarks, and other potentially relevant documents, Gustus et al.

U.S. Appl. No. 11/417,648, filed May 3, 2006, and its prosecution history, including office communications, amendments, remarks, and other potentially relevant documents, Gustus et al.

U.S. Appl. No. 11/417,909, filed May 3, 2006, and its prosecution history, including office communications, amendments, remarks, and other potentially relevant documents, Gustus et al.

U.S. Appl. No. 11/417,882, filed May 3, 2006, and its prosecution history, including office communications, amendments, remarks, and other potentially relevant documents, Gustus et al.

U.S. Appl. No. 13/210,261, filed Aug. 15, 2011, including office communications, amendments, remarks, and other potentially relevant documents, Fangrow et al.

Search Report for PCT/US2006/026124, dated Mar. 13, 2007 in 5 pgs.

Written Opinion for PCT/US2006/026124, dated Jul. 6, 2006 in 11 pgs.

* cited by examiner

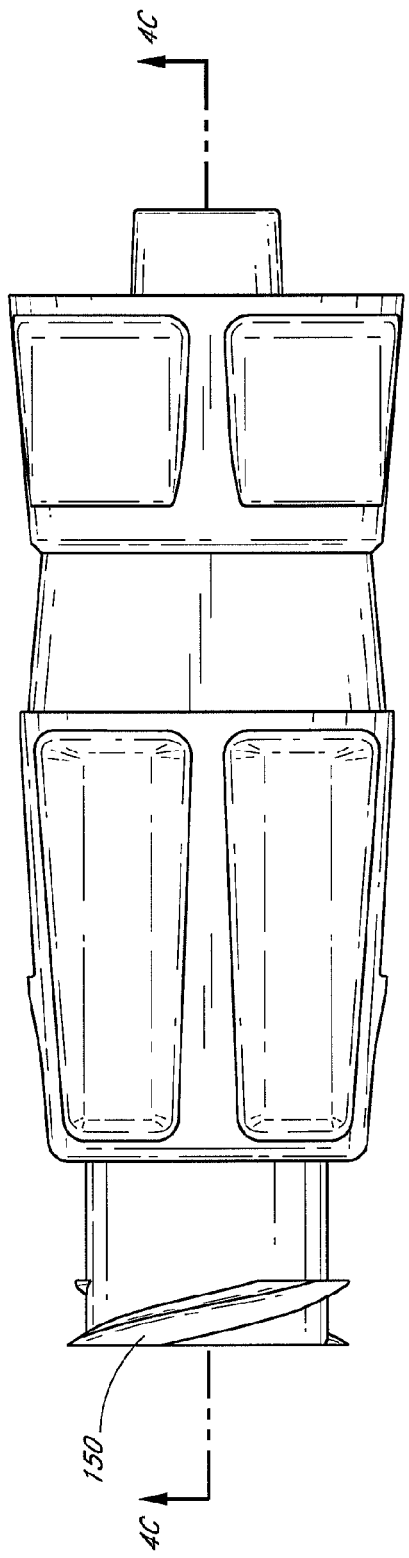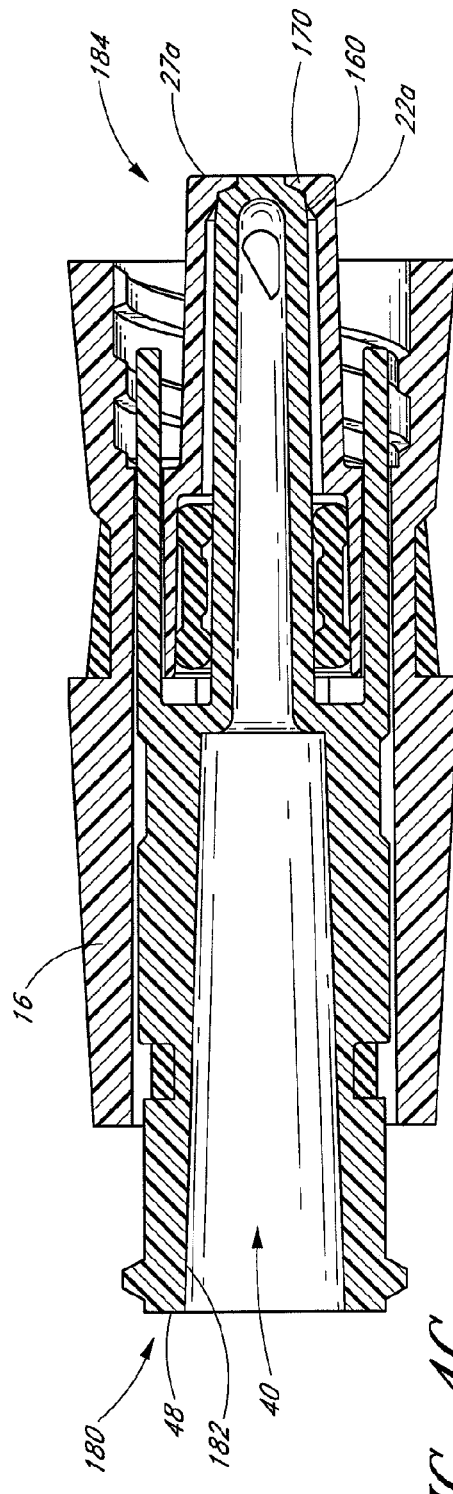

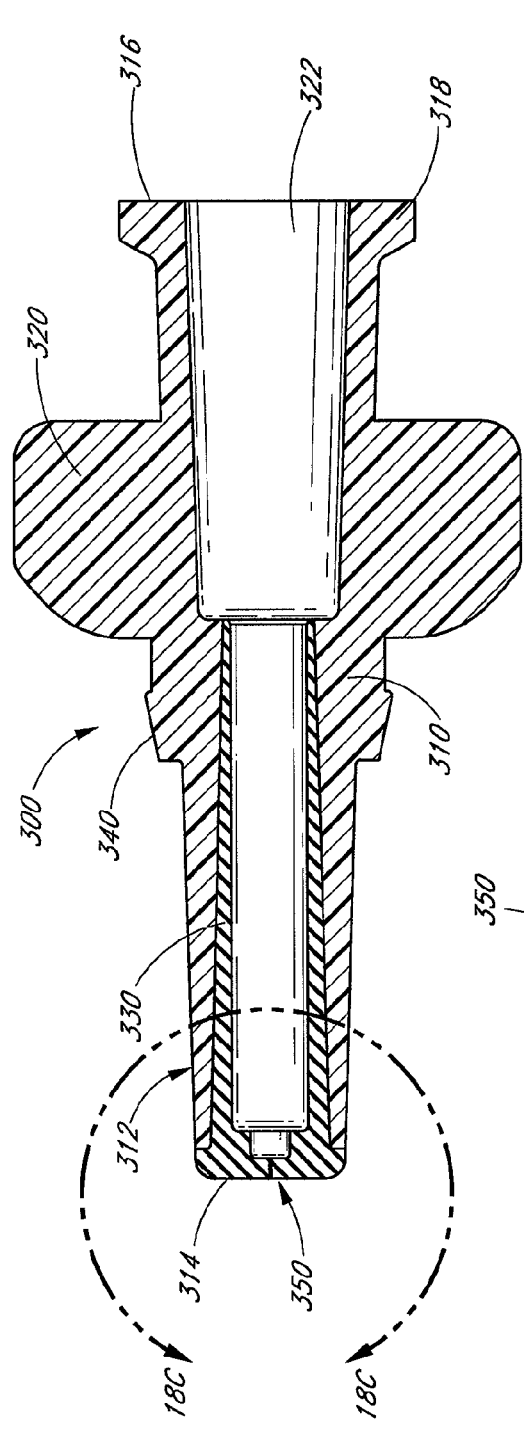
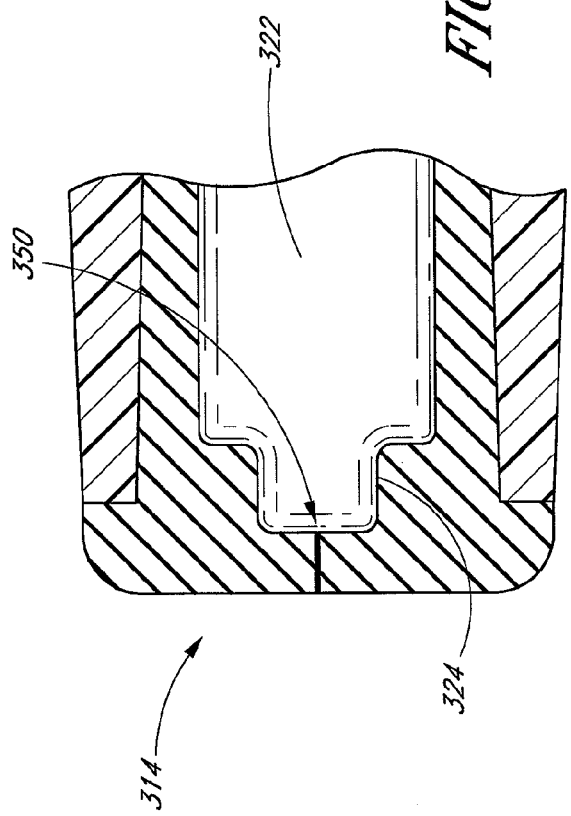
FIG. 18B
FIG. 18C

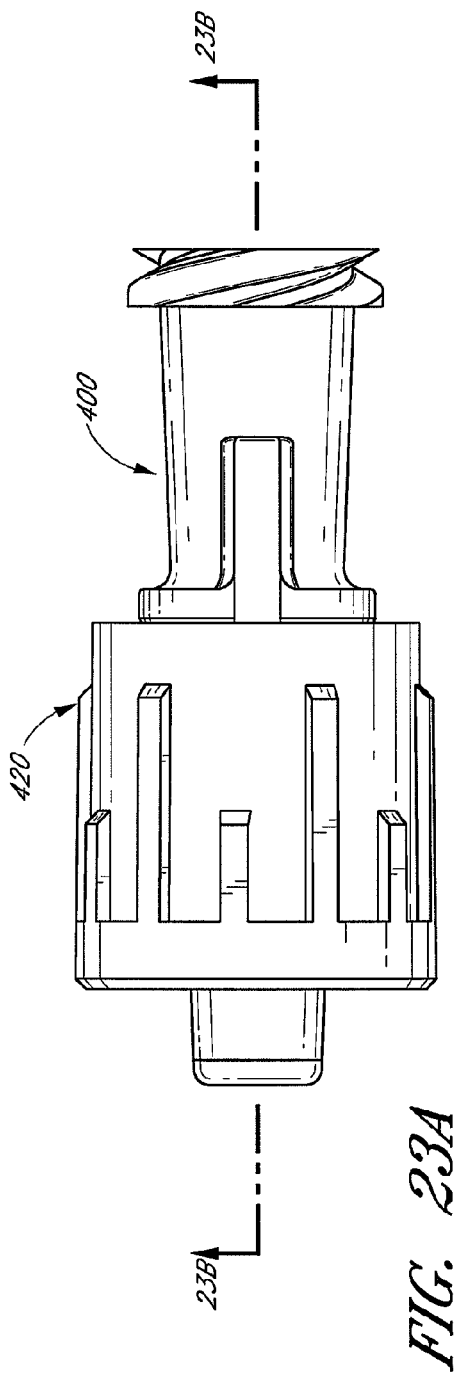
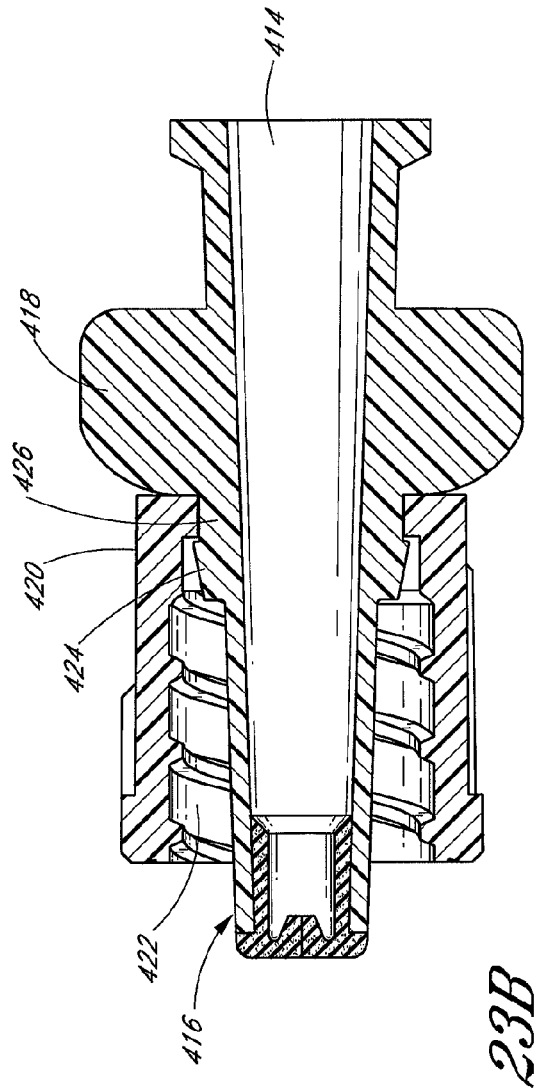
FIG. 23A
FIG. 23B

MEDICAL CONNECTOR WITH CLOSEABLE MALE LUER

CROSS-REFERENCE TO RELATED APPLICATIONS

This application is a continuation of U.S. patent application Ser. No. 11/417,604, filed May 3, 2006, pending, which claims the benefit under 35 U.S.C. §119(e) of U.S. Provisional Patent Application No. 60/696,894, filed Jul. 6, 2005, and U.S. Provisional Patent Application No. 60/707,319, filed Aug. 11, 2005, the disclosures of each being hereby incorporated by reference in their entireties.

BACKGROUND OF THE INVENTIONS

1. Field of the Inventions

This invention relates generally to medical connectors through which fluids flow, and in particular, to medical connectors with male luers.

2. Description of the Related Art

Systems of connectors, valves, and tubing are routinely used in hospitals and other medical settings for facilitating the transfer of fluids to and from patients. It is often a challenge to keep such systems sterile and to prevent leakage of fluids when the various components are engaged and disengaged.

In order to maintain a barrier to bacteria, debris, and fluid leakage, female connectors often have been provided with closures, such as septa, flexible seals, or other impediments, at their mating ends. When a male luer connector is engaged with the female connector, the closure of the female connector is temporarily opened, pierced, or moved to allow fluid to flow between the two connectors. Male connectors typically employ needles or luers to open, pierce, or move the closure on the female connectors.

In many systems, only the female connectors are automatically blocked from the external environment when disengaged. Male luer connectors are generally not provided with automatic closing mechanisms. Male luer connectors sometimes employ additional components, such as caps, to stop the flow of fluid and impede the entry of bacteria and debris. Because such closure mechanisms are not automatic (or not used at all), male luer connectors are sometimes left unsealed, allowing fluid to drip out. This may increase the risk of unsanitary conditions inside and outside of the fluid transfer system. In addition, in some medical applications such as certain chemotherapy treatments, the fluids in the tubing and connectors can be harmful if released.

Moreover, in the busy environment of hospitals and other medical settings, health care providers must often quickly manipulate multiple medical implements with one hand, making it difficult to retrieve male luer caps and rapidly attach them upon disengagement of male connectors. In addition, male luer connectors are often employed at the downstream end of gravity-fed fluid sources such as IV bags. When the connectors and tubing are initially connected to such sources, they are generally empty (i.e., filled with air) and must be primed with fluid before they can be connected to a patient. During the priming procedure, fluid is allowed to flow from the upstream end of the tubing toward the male luer connector on the downstream end. As the flow flows through the tubing, the air in the tubing escapes through the male connector on the downstream end into the environment. Once the fluid itself reaches the male connector, it can also escape and spill out. Because male luer connectors do not usually close automatically after priming, the male luer often drips out a small amount of fluid as the male connector is rapidly moved into mating engagement with a female connector. For this reason, the male luer is generally held over a sink or trash can at the end of the priming procedure to contain the dripping fluid.

There is a need for a closable male luer connector that automatically opens when engaged with a female connector and automatically closes when disengaged from such connector to minimize or eliminate dripping during priming and other procedures and to improve the barrier of the fluid transfer system against bacteria and other debris.

SUMMARY OF THE INVENTION

Disclosed are various embodiments of medical connectors with closable male luers. It is contemplated that the features of the various embodiments disclosed herein are combinable to form additional embodiments. Such combinations are within the scope of this disclosure.

In an exemplary embodiment, a male luer connector has a main housing with first and second ends. The second end of the housing comprises a male luer and a shroud surrounding at least a portion of the male luer. The shroud has screw threads disposed on an internal wall thereof. A tubular valve member with a fluid pathway is disposed within the housing. The valve member has a tip on its second end. In the region near the tip, a pair of fluid holes is positioned on opposite sides of the valve member. The tip is configured to abut snugly against an internal wall of the male luer in a region at or near the second end of the male luer. The valve member also has a pair of struts directed towards the second end. The struts extend axially through a portion of the housing, and the ends of the struts towards the second end are positioned within a space between the male luer and the shroud on the second end of the housing. A length of medical tubing is connected to the connector. An end of the tubing is attached to the first end of the valve member by adhesive, welding, or some other means. A resilient, elastomeric member extends from a mid-section region on the outside of the housing to a region at or near the first end of the valve member within the housing.

In a substantially closed state, the resilient member is configured to pull the housing and the tubular valve member together along their respective axes. In this state, the tip of the valve member is pressed into close contact with a portion of the internal wall on the second end of the male luer, and fluid flow from the medical tubing through the tubular valve member is impeded. Fluid generally cannot escape through the opening on the second end of the male luer because such opening is blocked by the tip of the valve member.

When a force is applied to separate the valve member from the housing, the resilient member is stretched and the tip of the valve member is displaced in the direction of the first end from the second end of the male luer. This separating force can be applied manually, for example, by grasping the external wall of the housing with two fingers and grasping the tubing adhered to the first end of the valve member with two other fingers, and then moving the fingers in opposite direction. The separating force can also be applied automatically by a different manual action. For example, the action of connecting the male luer to a female end of another medical implement can automatically separate the valve member from the housing. As the advancing end of the female connector proceeds up the screw threads on the second end of the housing of the male luer connector, the female connector makes contact with and exerts a force directed towards the first end against the struts of the valve member. This force moves the valve member towards the first end against the biasing force directed towards the second end exerted by the resilient member. In this opened state, fluid is permitted to flow through the opposing holes, around the tip of the valve member, and out of the connector through the gap between the tip of the valve member and the internal wall on the second end of the male luer. In some embodiments, the valve member is automatically advanced in the direction of the first end when the valve member contacts a fluid conduit (e.g., a spike positioned within a female connector) as the male and female connectors are brought together.

When the separating force is removed, for example, by releasing the manual grip on the housing and the tubing, or by detaching the female connector from the second end of the housing, the resilient member once again draws the housing and the valve member together. This causes the tip on the second end of the valve member to abut closely against a portion of the internal wall in a region near the second end of the male luer, and impedes fluid flow out of the valve.

Also disclosed herein are other features and configurations for the foregoing embodiment, as well as additional embodiments for other connectors with closable male luers. Such embodiments generally include means for permitting or impeding fluid flow through a male luer on a connector, preferably automatically upon connection with a corresponding female connector.

BRIEF DESCRIPTION OF THE DRAWINGS

Certain embodiments of this invention will now be discussed in detail with reference to the following figures. These figures are provided for illustrative purposes only, and the invention is not limited to the subject matter illustrated in the figures.

FIG. 4B shows a perspective view of another embodiment of a valve member portion of the connector of FIG. 2.

FIG. 4C shows a cross-sectional view of the embodiment of the valve member portion of the connector of FIG. 4B.

FIG. 18B is a cross-sectional view of the connector of FIG. 18A.

FIG. 18C is a detail of the cross-sectional view of the connector of FIG. 18A.

FIG. 23A is a side view of another embodiment of a closeable male luer connector with a shroud.

FIG. 23B is a cross-sectional view of the connector of FIG. 23A.

DETAILED DESCRIPTION OF THE PREFERRED EMBODIMENTS

In one aspect of the present inventions, a variety of means are shown for closing the second end of a male luer connector. In some embodiments, these closing mechanisms function to prevent and/or impede fluid from escaping from or entering into the male luer, while allowing fluid flow when the male luer is manually opened or engaged with a corresponding female luer. As used herein, terms such as "closed" or "sealed" should be understood as obstructions or barriers to fluid flow. These terms should not be understood to require that a particular structure or configuration achieves a complete fluid closure in all circumstances.

Figure 1A:
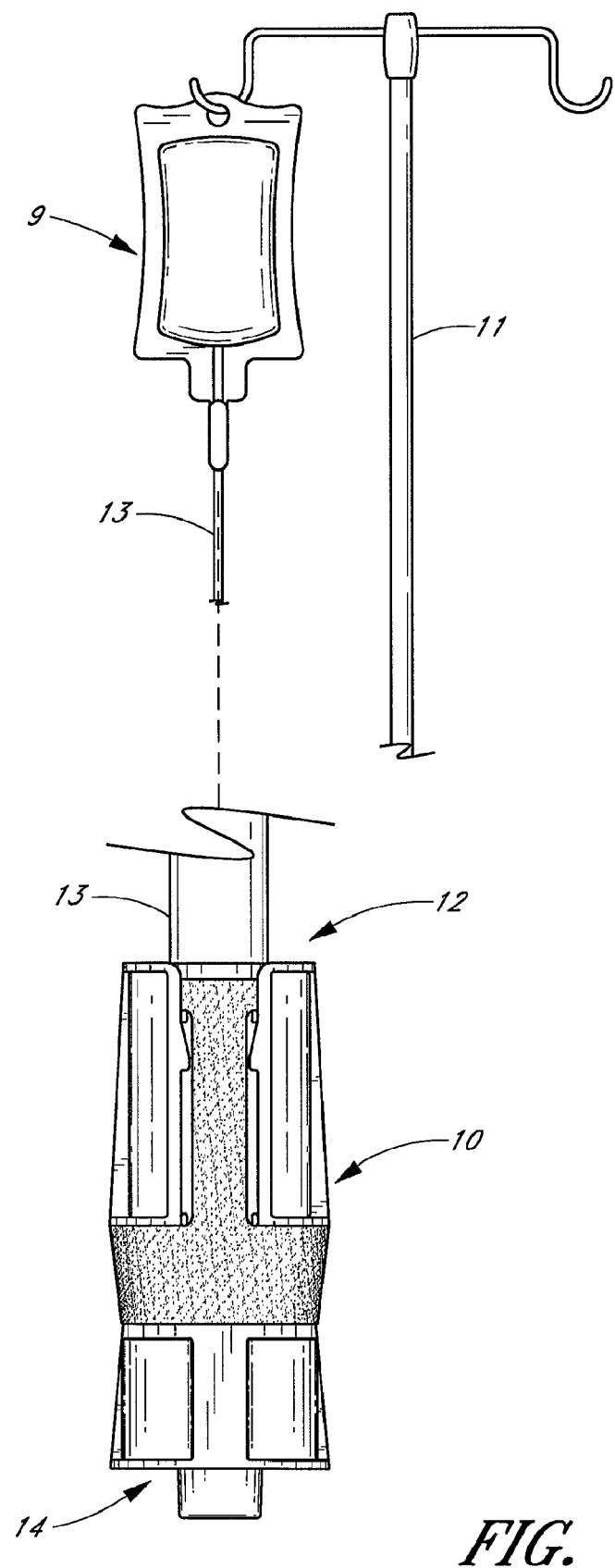
FIG. 1A shows a perspective view of an embodiment of a male luer connector attached to tubing configured to receive fluid from a hanging gravity-fed IV bag. In this and other figures, the relative size of the connector and attached tubing is increased in comparison to other objects to facilitate viewing certain details.

In FIG. 1A, an embodiment of a closable male luer connector 10 is shown in a closed position. The luer connector 10 is attached to a gravity-fed IV bag 9 filled with fluid hanging from a pole stand 11. At the bottom of the bag 9, a section of tubing 13 is attached. The opposite end of the tubing 13 is connected to the first end 12 of the luer connector 10. A closing mechanism on the interior of the second end 14 of the luer connector 10 prevents the fluid contained within the bag 9 from flowing through the tubing 13 and leaking out of the luer connector 10, as long as the luer connector 10 remains in a closed configuration.

Figure 1B:
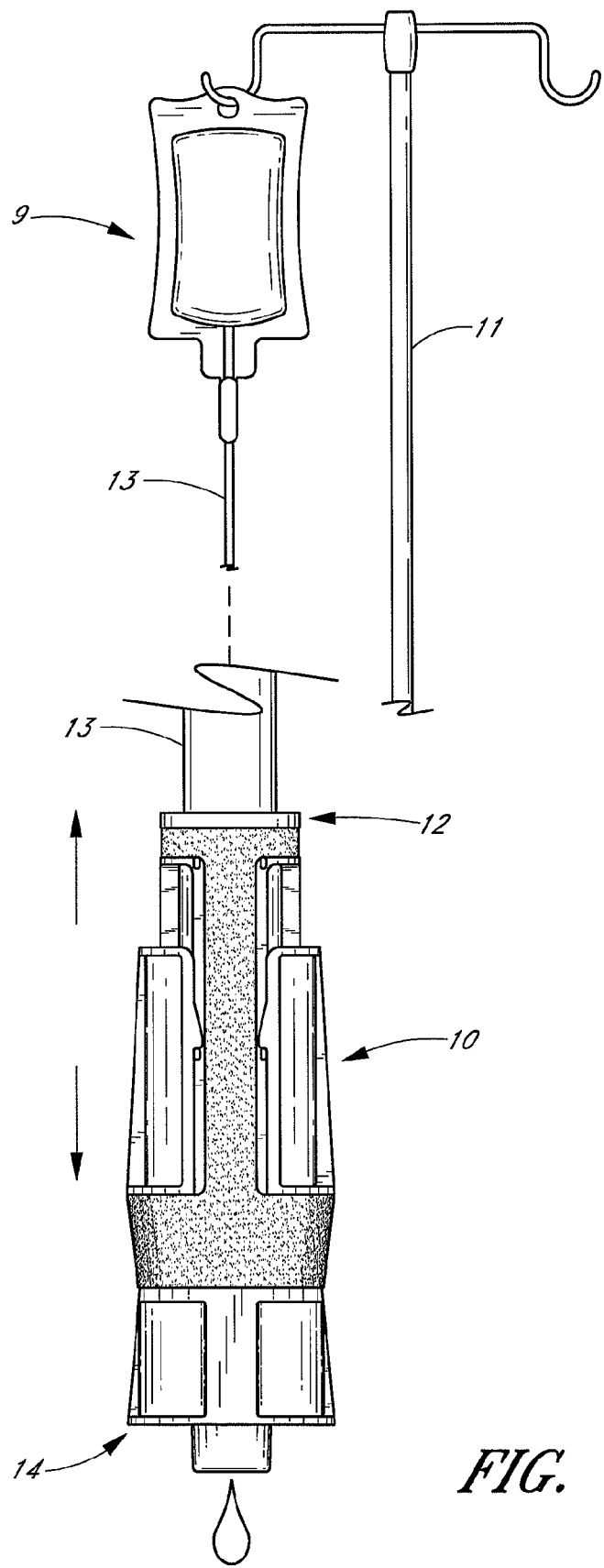
FIG. 1B shows a perspective view of the connector of FIG. 1A in a stretched, substantially opened configuration.

In FIG. 1B, the connector 10 is illustrated in an open position. Fluid can flow out into the first end 12 of the connector 10 and out of the second end 14 of the connector 10. A health care provider can move the male luer connector 10 into this configuration by grasping the second end of the closable male luer 10 with two fingers, grasping the tubing 13 with two other fingers, and gently moving the fingers in opposite directions.

The IV delivery system illustrated in FIGS. 1A and 1B can be easily readied for fluid communication with a patient. In most circumstances, the tubing 13 is filled with air when it is initially connected to the IV bag 9. If the other end of the tubing 13 is connected to a closed connector, as illustrated in FIG. 1A, the air cannot escape and fluid cannot enter the tubing 13 from the IV bag 9. The luer connector 10 is therefore manually moved into the opened position until all of the air has been purged through the luer 10 and the fluid in the IV bag 9 fills the tubing 13 and connector 10. This procedure is known as "priming." As soon as the fluid line and connector are properly primed, the health care provider can quickly release the opposing forces applied to the second end 14 of the luer connector 10 and the tubing 13, and the closing mechanism of the luer connector 10 can rapidly stop the flow of fluid through the luer connector 10.

Figure 1C:
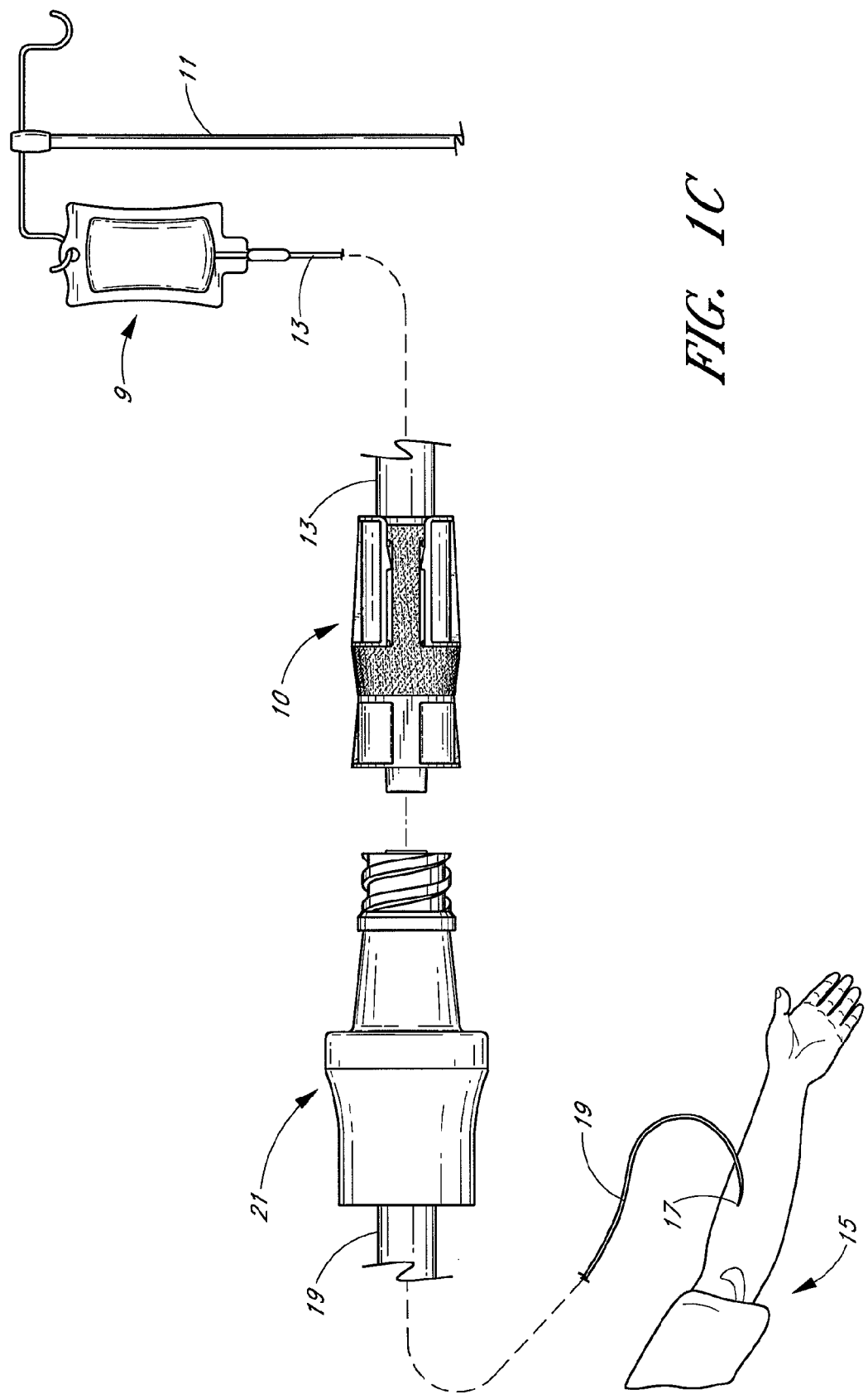
FIG. 1C shows a perspective view of an embodiment of the connector of FIG. 1A being connected to an exemplary female connector attached to tubing inserted into a patient.

Referring now to FIG. 1C, a catheter 17 has been inserted into a patient's arm 15. The catheter 17 penetrates the skin of the arm 15 and is preferably fluidly connected with the patient's bloodstream. The catheter 17 is also connected to a length of medical tubing 19 attached to a female medical connector 21. The example of a female medical connector 21 illustrated in FIG. 1C is a version of the Clave® connector manufactured by ICU Medical, Inc., San Clemente, Calif. Various embodiments of a connector of this type are illustrated and described in U.S. Pat. No. 5,685,866, which is incorporated herein by reference in its entirety. It is contemplated that many of the male luer embodiments disclosed herein can be used with other types of female connectors. The tubing 19, catheter 17, and female connector 21 were previously primed with fluid using standard procedures. The luer connector 10 is primed as described previously and brought into engagement with the female connector 21. As described in further detail below, when the male connector 10 and female connector 21 are engaged, fluid is permitted to flow from the IV bag 9 into the patient. When the male connector 10 and female connector 21 are disengaged, fluid is once again prevented from flowing out of the second end 14 of the male connector 10. In general, fluid is also prevented from flowing out of the opening in the female connector 21.

The embodiment illustrated in FIGS. 1A-1C is described in further detail below. Each of the other embodiments disclosed herein can be used in the illustrated fluid system, and in various modifications and alternatives thereof. Further, it is contemplated that the various embodiments of connectors in accordance with the inventions can be used in a wide variety of additional medical fluid systems. For example, the disclosed connectors can also be used to transfer bodily fluids such as blood, urine, or insulin, nourishing fluids, and/or therapeutic fluids such as fluids used in chemotherapy treatments. The disclosed connectors can also be used to interconnect various other components of fluid transfer systems.

Figure 2:
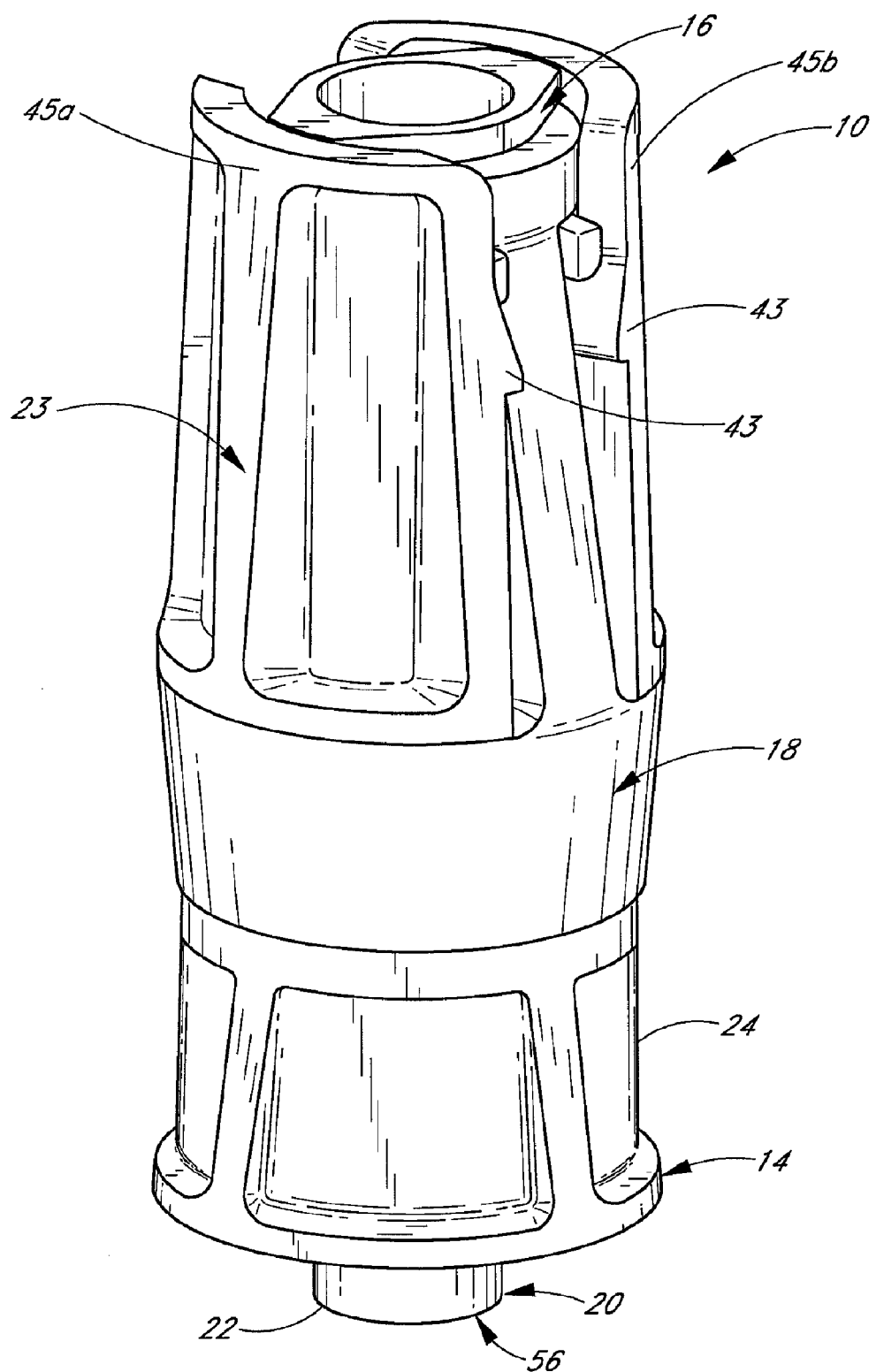
FIG. 2 shows a perspective view of an embodiment of a closeable male luer connector.

Referring now to FIGS. 2-9, the closeable male luer of FIGS. 1A-1C is illustrated in greater detail. As illustrated in FIG. 2, the assembled luer connector 10 comprises four portions: a housing 23, a valve member 16, a resilient member 18, and a sealing ring 20 (not visible in FIG. 2). These portions are individually illustrated in FIGS. 3 through 6, and will be discussed in further detail with reference to these figures. The luer connector 10 can be constructed of more or fewer portions, and such portions can be combined into different configurations.

Figure 3:
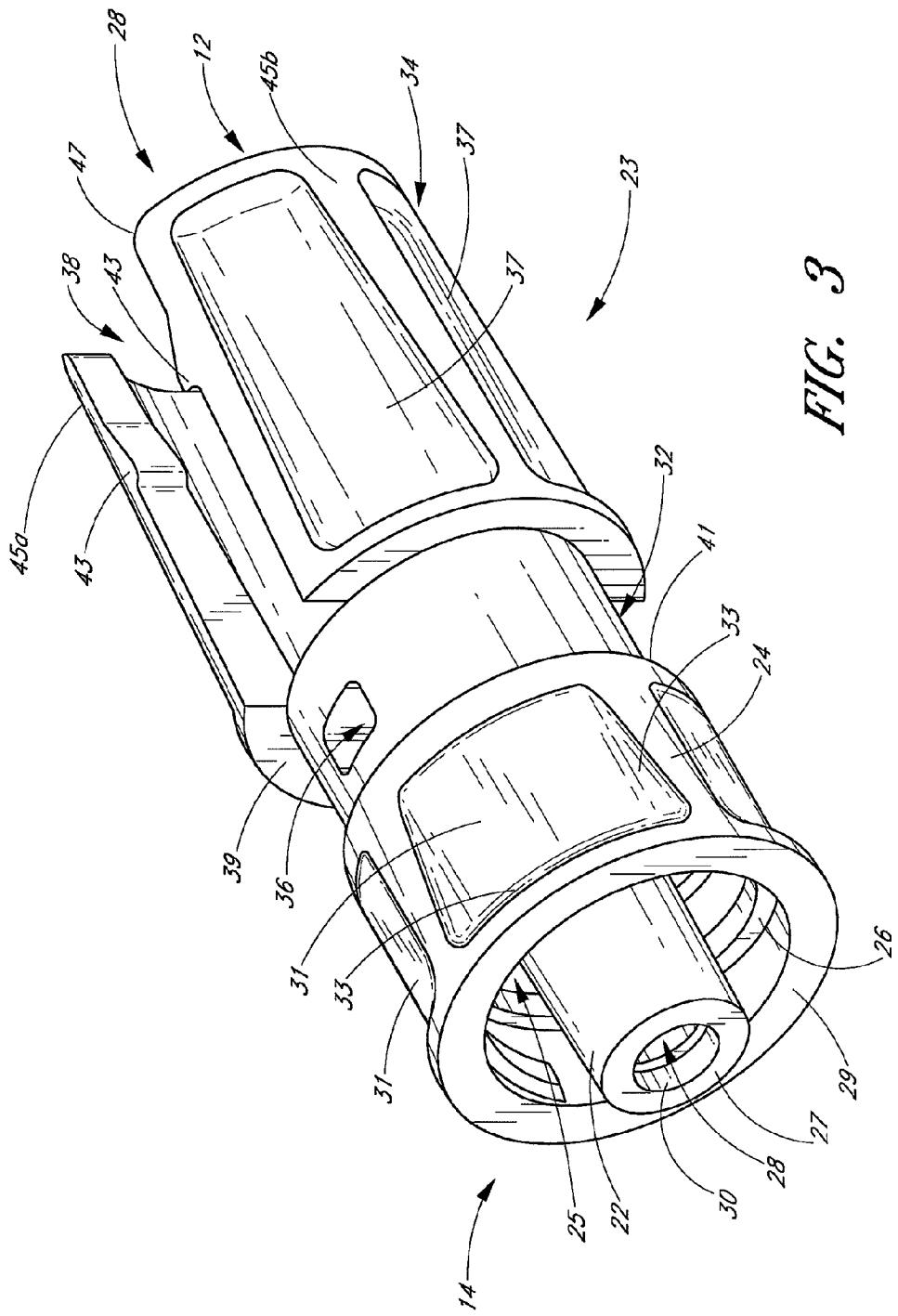
FIG. 3 shows a perspective view of a housing portion of the connector of FIG. 2.

FIG. 3 illustrates the housing 23 of the connector 10, apart from the other portions of the luer connector 10. The housing 23 is generally a tube-like structure with an axial passageway 28 that extends from the first end 12 of the connector 10 through the upper housing 34, and the middle portion 32, and the luer tip 22, to the second end 14 of the housing 23. In some embodiments, the length of the housing 23 from the first end 12 to the luer tip 22 is approximately 1⅛ inches. The housing 23 is preferably, but not necessarily, less than or equal to about 1½ inches from the first end 12 to the second end 14 so that the weight and bulk of the connector are minimized. The housing 23 can have any suitable length for a particular application. The luer tip 22 connects to the remainder of the housing 23 at a base 25 that is surrounded by a shroud 24. The end 27 of the luer tip 22 towards the second end of the luer connector 10 extends some distance beyond the edge 29 of the shroud.

The shroud 24 preferably has inner threads 26 on an interior wall that help securely attached the connector 10 in a removable fashion to another medical implement. In other embodiments, the shroud 24 can include other structures or materials for providing a releasable connection, including quick-release mechanisms and other means. The shroud 24 includes a plurality of depressions 31 on an outer surface to assist the user in firmly grasping and twisting the shroud 24 of the housing 23 with the fingers. The depressions 31 have upwardly tapering sidewalls 33 that prevent the fingers from sliding off the connector 10. On an end towards the first end of the connector 10 of each depression 31, the surface of the housing 23 is approximately co-planar with the surface of the depression 31, while on an end towards the second end 14 of the connector 12 of each depression 31, the surface of the housing 23 is offset from, and preferably lies above, the surface of the depression 31. This configuration allows the fingers to comfortably slide in a direction towards the second end 14 of the connector 10 along the housing 23 into a position for gripping or twisting the connector 10. Once the fingers are in the desired position, a tapered wall 33 on an end towards the second end 14 of the connector 10 of the depression 31 resists further movement by the fingers in the direction of the second end 14. A series of depressions 31 extend around substantially the entire outer surface of the shroud so that the user's fingers, when positioned on opposite sides of the connector 10, will likely encounter a depression 31 regardless of the orientation of the connector 10 during use.

In the illustrated embodiment, the tip 22 has a tapered external wall. The diameter of the tip 22 becomes gradually smaller from the base 25 towards the second end 27. The tip 22 includes a hole at its second end 27. At the base 25 of the luer tip 22, an interior hole 35 (see FIG. 8) leads into a region of the fluid passageway 28 in the middle portion 32 of the luer connector 10. The dimensions of the luer tip can be made to comply with applicable standards and/or regulations, such as the ANSI standards.

The interior wall of the luer tip 22 preferably includes a shelf 30 that extends radially inwardly toward the axis of the fluid passageway 28 surrounded by the luer tip 22, making the fluid passageway 28 narrower at its second end 27 than in the region adjacent to the second end 27. In the illustrated embodiment, the surface of the shelf 29 that faces radially inwardly toward the central axis of the connector 10 is tapered in a manner similar to the taper of the outer surface of the tip 22 (see FIGS. 8 and 9). In this configuration, the inner diameter of the shelf 29 narrows in a direction from the side towards the first end to the side of the shelf 29 towards the second end. As described in further detail below, the shelf 29 in the luer tip 22 helps to block and/or impede fluid flow through the connector 10 when the second end of the valve member 16 abuts against it.

The middle portion 32 of the housing 23 lies between the shroud 24 and the upper housing 34. As illustrated, the middle portion 32 has a smaller outer diameter than either the shroud 24 or upper housing 34. The middle portion 32 also has two generally rectangular openings 36 disposed on opposite sides of the housing 23 from each other. When the connector 10 is assembled, the middle portion 32 is generally covered by a portion of the resilient member 18 (see, e.g., FIG. 2). As a result, the middle portion 32 does not generally come into contact with the fingers during use. Thus, in some embodiments, a grippable surface need not be used for the middle portion 32. The middle portion 32 can therefore have a smaller diameter and smoother surface than either of the other sections of the housing 23.

The upper housing 34 is generally split into two wall sections 45a, 45b by two gaps 38 (only one shown in FIG. 3). The upper housing 34 includes a series of depressions 37 similar in shape and function to the depressions 31 on the shroud 24. The upper housing 34 may also comprise one or more protrusions 43 that extend into the gaps 38. In the assembled configuration, the protrusions 43 help to retain a portion of the resilient member 18 between the gaps 38 in the wall sections 45a, 45b (see FIG. 2). In some embodiments, the protrusions 43 are tapered from a smaller thickness on their ends towards the first end of the connector to a larger thickness on their ends towards the second end of the connector. The tapering of the protrusions 43 helps in the insertion and retention of the portion of the resilient member 18 in a desired position and orientation, while allowing for bending and contortion of the resilient member 18 during use. The protrusions 43 also help prevent the valve member 16 from advancing too far in the direction of the first end as the connector 12 is moved into the opened position by contacting the set of protrusions 44 toward the second end of the valve member 16. The tapering of the protrusions 43 allows the protrusions 44 of the valve member 16 to be advanced towards the second end during assembly into the housing 23 past the protrusions 43 of the housing 23. The corners 47 towards the first end of the connector on each of the wall sections are preferably rounded to prevent snagging, scratching, or other damage or irritation to the fingers or resilient member 18 during use.

As shown in FIG. 3, the exterior surface of the upper housing 34 includes a lower shelf 39 and the exterior surface of the shroud 24 includes a shelf 41 configured to help retain a central portion of the resilient member 18 around the housing 23 in the assembled configuration (see FIG. 2). The shelf 39 of the upper housing 34 is preferably substantially horizontal to discourage any sliding of the resilient member 18 in the direction of the first end of the connector. The shelf 41 of the shroud 24 is preferably tapered (see FIG. 8) to assist in the proper positioning of the resilient member 18 on the housing 23 during manufacturing of the connector 10.

The housing 23 can be constructed from any of a number of different materials. In some embodiments, the housing 23 can be constructed from a relatively rigid material, such as polycarbonate or other polymeric material. The housing 23 and/or valve member 16 of this embodiment, or components of other embodiments, can also be constructed of a hydrophobic material, such as Bayer Makrolon, or any other suitable material.

Figure 4A:
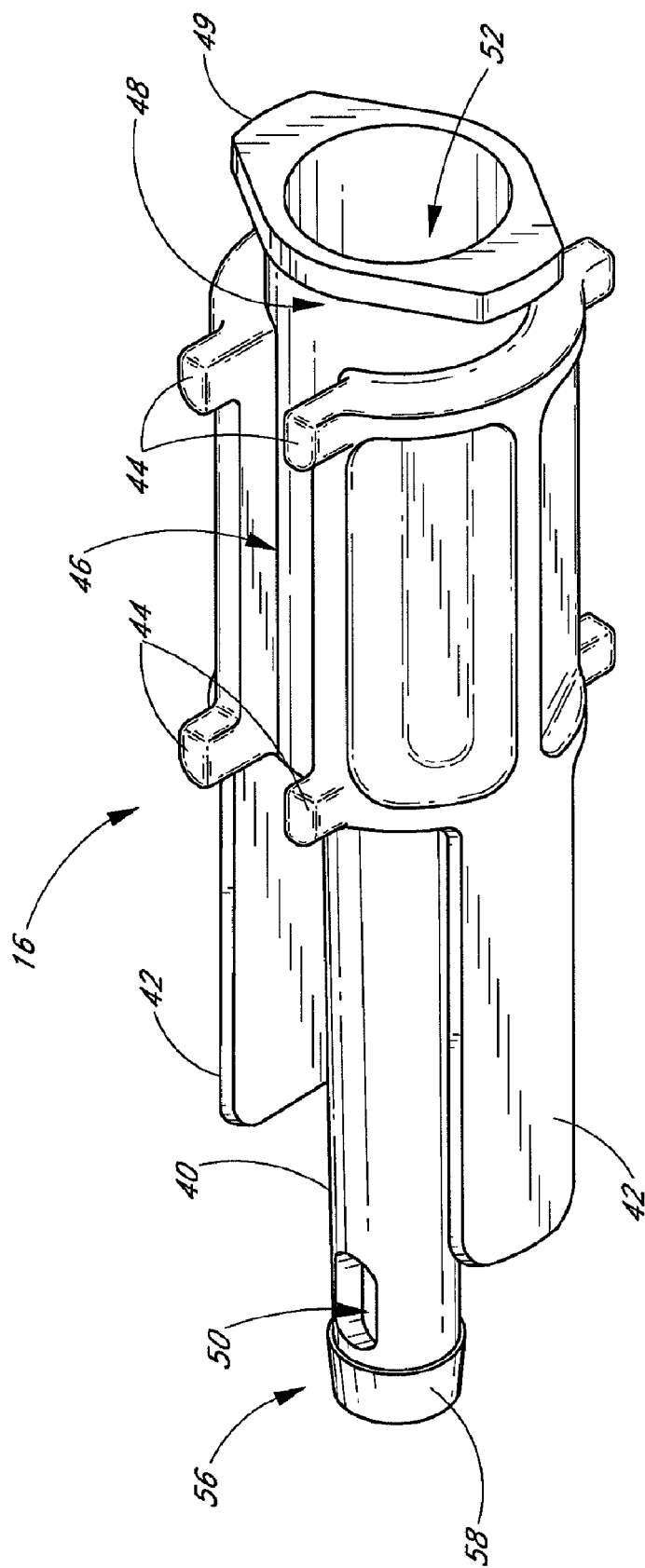
FIG. 4A shows a perspective view of a valve member portion of the connector of FIG. 2.

Referring now to FIG. 4A, the valve member 16 of the male luer 10 is illustrated apart from the other components of the connector 10. In some embodiments, the valve member 16 comprises a fluid passageway 52 of varying diameter extending from the first end 48 of the valve member 16 to the second end 56 thereof, surrounded by additional structures. Near the first end 48, the valve member 16 and corresponding section of the fluid passageway 52 are relatively wide to accommodate a section of standard-diameter medical tubing inserted therein. Near the middle of the valve member 16, a tube 40 surrounding a portion of the fluid passageway 52 is attached to the portion near the first end of the valve member 16. The tube is adjacent to two approximately parallel struts 42 along at least a portion of the tube 40. The tube 40 can have a circular cross-section or other appropriate cross-section. The struts 42 are preferably relatively thin and approximately planar. A first end of each strut 42 connects to the valve member 16 at approximately the middle section of the valve member 16, and a second end of each strut extends toward the second end 56 of the valve member 16. The second end 56 of the valve member 16 preferably extends further than the ends of the struts. There is preferably an open space between the inner wall of each strut 42 and the outer wall of the tube 40.

From near the middle of the valve member 16 to the first end 48 thereof, the fluid passageway 52 comprises a wider region with protrusions 44 along its external surface. Protrusions 44 form two channels 46 (only one is shown in FIG. 4A) lengthwise along opposing sides of the body of the valve member 16. In some embodiments, the struts 42 are spaced circumferentially from the channels 46, as illustrated.

Near the first end of the valve member 16 and tube 40, a circumferential channel 48 may be formed around the perimeter of the body of the valve member 16. Raised tabs 49 can be formed along the edge of the channel 48 toward the first end of the connector, while the raised middle portion of the valve member 16 can form the edge of the channel 48 toward the second end of the connector. In some embodiments, the raised tabs 49 do not extend evenly about the perimeter of the first end of the valve member 16, but instead have two larger sections that are spaced diametrically from each other.

The amount of material necessary to construct the valve member 16 can be reduced by indentations made in the outer layers of this portion. The tube 40 can have a passage 50 disposed therethrough. This passage 50 preferably extends from a hole 52 at the first end of the valve member 16 to a pair of holes 50 (only one shown in FIG. 4A) positioned substantially adjacent to the second end of the valve member 16. In the illustrated embodiment, these holes 52 are generally rectangular in shape. The region of the tube 40 near the second end of the connector can also be formed with only one hole or more than two holes, and other shapes for one or more of the holes can also be employed. For example, the holes 52 can be formed with a tear-drop shape (e.g., narrow on one end and wider on an opposite end), which facilitates an injection molding process of manufacture. Further, in some embodiments, the valve member 16 can be constructed without a fluid path and function as a blocking plunger for fluid flowing around the valve member 16 rather than a means for conveying fluid between the first and second ends of the connector 10.

The tube 40 of the valve member 16 comprises, at its second end, a flange section 58. The flange section 58 preferably extends further in the radial direction than the adjacent portion of the tube 40. In some embodiments, the flange section 58 can be formed of the same or substantially the same material as the rest of the tube 40. The flange section 58 preferably tapers from the first end of the valve member 16 towards the second end of the tube 40. In some embodiments, the taper is formed at a 5-degree angle, and has a substantially identical taper to that of the radially inwardly facing surface of the shelf 30 of the housing 23. Other amounts of taper, or no taper, can also be used.

The valve member 16, like the housing 23 of FIG. 3, may be constructed from a number of different materials. Examples of such materials include polycarbonate or other polymeric materials. The valve member 16 can be approximately the same length or somewhat shorter than the housing 23. For example, the length of the valve member 16 can be approximately 1 inch. In some embodiments, the valve member 16 can be substantially shorter than the length of the housing 23. The valve member 16 can be formed from the same rigid materials as the housing 23. In certain applications, for example, semi-rigid or even more flexible materials may be desirable for use in the valve member 16, and more particularly for the flange section 58 toward the second end of the tube 40.

The valve member 16 can be manufactured through injection molding. In some embodiments, at least two gates are used to facilitate distribution of molten plastic throughout the mold. Preferably, one gate can be located along one of the sides of the valve member 16 between the end of the struts 42 towards the first end of the connector and the raised tabs 49 and another can preferably be located near the holes 52 in the valve member 16. The locations of the gates are not fixed, however, and other locations on the valve member 16 can be used for gates when injection molding the valve member 16. Constructing both the housing 23 and the valve member 16 of this or other embodiments out of the same material lessens the chance of deteriorated performance of the connector 10 due to thermal expansion/contraction or chemical interaction between the connector 10 and its environment.

Although the valve member 16 of the illustrated embodiment is configured as shown in FIG. 4A, many other configurations are possible. In some embodiments, the valve member 16 can be relatively smooth on its external surface, and can principally comprise the tube 40 defining the passage 50. In still other embodiments, different numbers of struts 42 can be disposed along the sides of the valve member 16.

As can be seen in the embodiment illustrated in FIG. 4B, the raised tabs 150 near the first end of the valve member 16 can also comprise an external engaging surface 150, such as a screw thread, for removably attaching a medical implement (not shown), such as a syringe, with the first end of the valve member 16.

In the embodiment illustrated in FIG. 4C, the channel 48 additionally can be tapered along the internal surface 182. The taper of the channel 48 can result in a decrease in width of the channel with a larger size at the first end 180 of the valve member 16 and a smaller size towards the second end 184 of the valve member. The internal taper of the channel 48 can compliment and closely fit with the taper of a male luer. Such an internal taper can conform to ANSI standards and/or regulations, such as the standard for medical syringes. In the illustrated embodiment, the tube 40 of the valve member 16 does not have a flange section 58 that extends radially outwardly beyond the wall of the tube 40, as in the embodiment of FIG. 4A. Instead, the wall of the tube 40 tapers radially inwardly in the region of the second end. The second end 27*a* of the luer tip 22*a* can have a smaller cross-sectional second portion 170 which decreases the likelihood of fluid escaping along the internal surface of the second end 27*a* of the luer tip 22*a*. Near the second end 27*a* of the luer tip 22*a*, a larger cross-sectional region 160 can transition to the smaller cross-sectional portion 170 towards the second end of the connector in many different ways, such as with an abrupt stair-step transition as illustrated in FIG. 4C or with a gradual tapering transition, or other transitions. Some sample cross-sectional diameters of the opening at the second end 27*a* of the luer 22*a* include those of about 2 mm or less, including about 0.5 mm, 0.75 mm, 1.0 mm, 1.25 mm, 1.5 mm, and 1.75 mm. The diameters of the opening in the second end 27*a* can also be in the ranges of 0.4 mm-1.8 mm, 0.5 mm-1.5 mm, and 0.5-1.0 mm. Other diameters, either inside or outside the listed ranges can also be used. Additionally, the second end of the valve member 16 can be sized appropriately to occupy the space in the opening of the second end 27*a* of the luer 22*a*.

Figure 5:
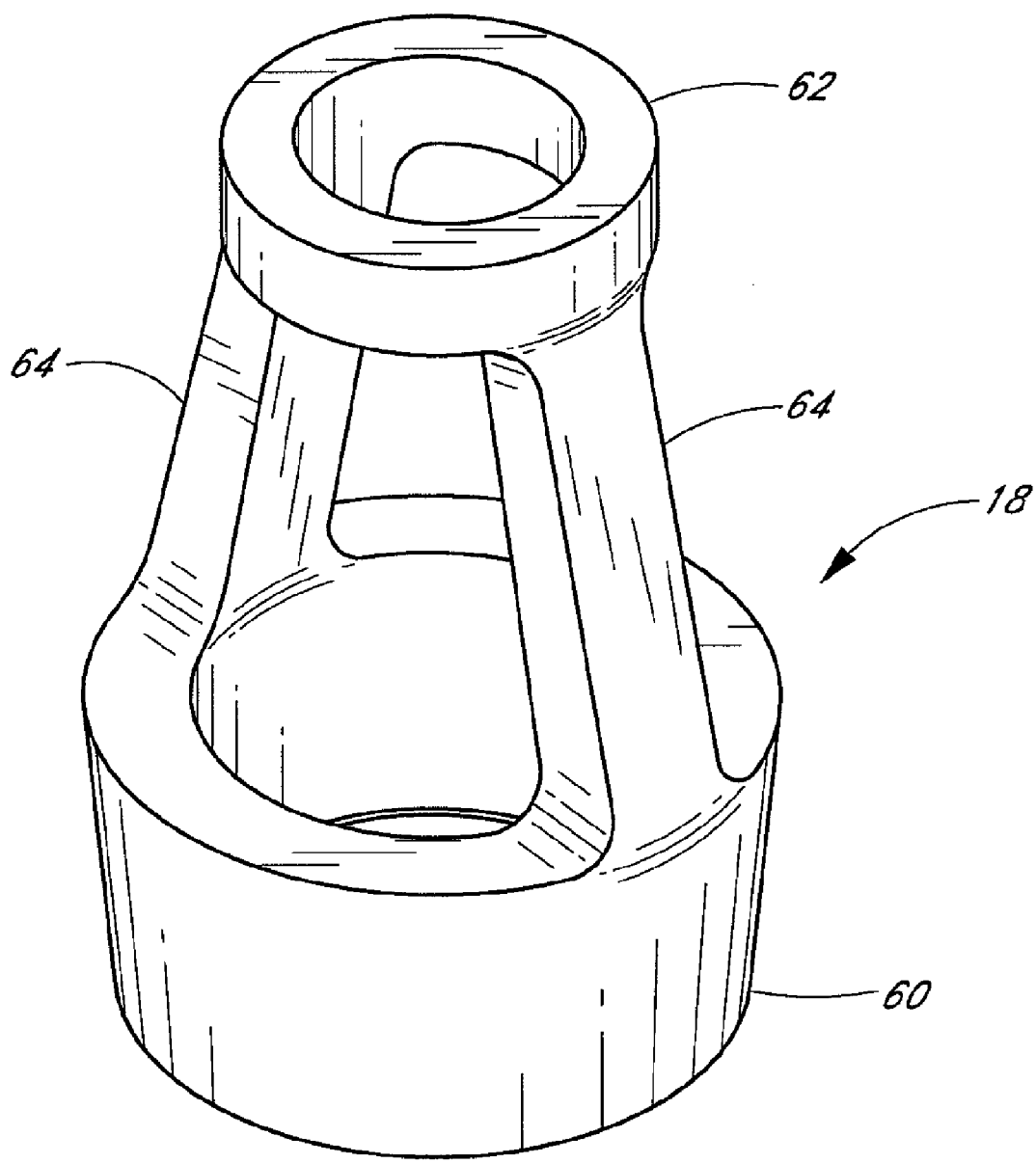
FIG. 5 shows a perspective view of a resilient member of the connector of FIG. 2.

Turning now to FIG. 5, the resilient member 18 is discussed in greater detail. In the illustrated embodiment, the resilient member 18 is formed from two rings 60, 62 separated by two elastic members 64. The rings 60, 62 and/or the elastic members 64 can be made of a deformable material configured to exert a restoring force when stretched. Thus, if the rings 60, 62 are pulled in opposing directions, the elastic members 64 function to restore the rings 60, 62 to their unextended configuration.

The elastic members 64 can be constructed from a number of elastic materials. In some embodiments, the elastic members 64 are made from a silicon rubber elastic material. In other embodiments, the elastic members 64 can be made from a shape-memory material. In still other embodiments, the elastic members 64 and/or the resilient member 18 can comprise springs or other structures capable of exerting a restoring force.

The rings 60, 62 can also be constructed from a number of materials. In some embodiments, the rings 60, 62 are constructed from the same deformable elastic material that comprises the elastic members 64. Thus, the rings 60, 62 can be stretched into a diameter to extend around the appropriate portion of the housing 23 to which each respective ring 60, 62 is attached. The resilience of the rings 60, 62 can function to effectively hold each ring 60, 62 in place on the housing 23. In other embodiments, the rings 60, 62 can be constructed from rigid or semi-rigid materials, and can, for example, comprise half-circles that can be snapped into and out of position. In some embodiments, the resilient member 18 can be integrated into the valve member 16 or housing 23.

Figure 6:
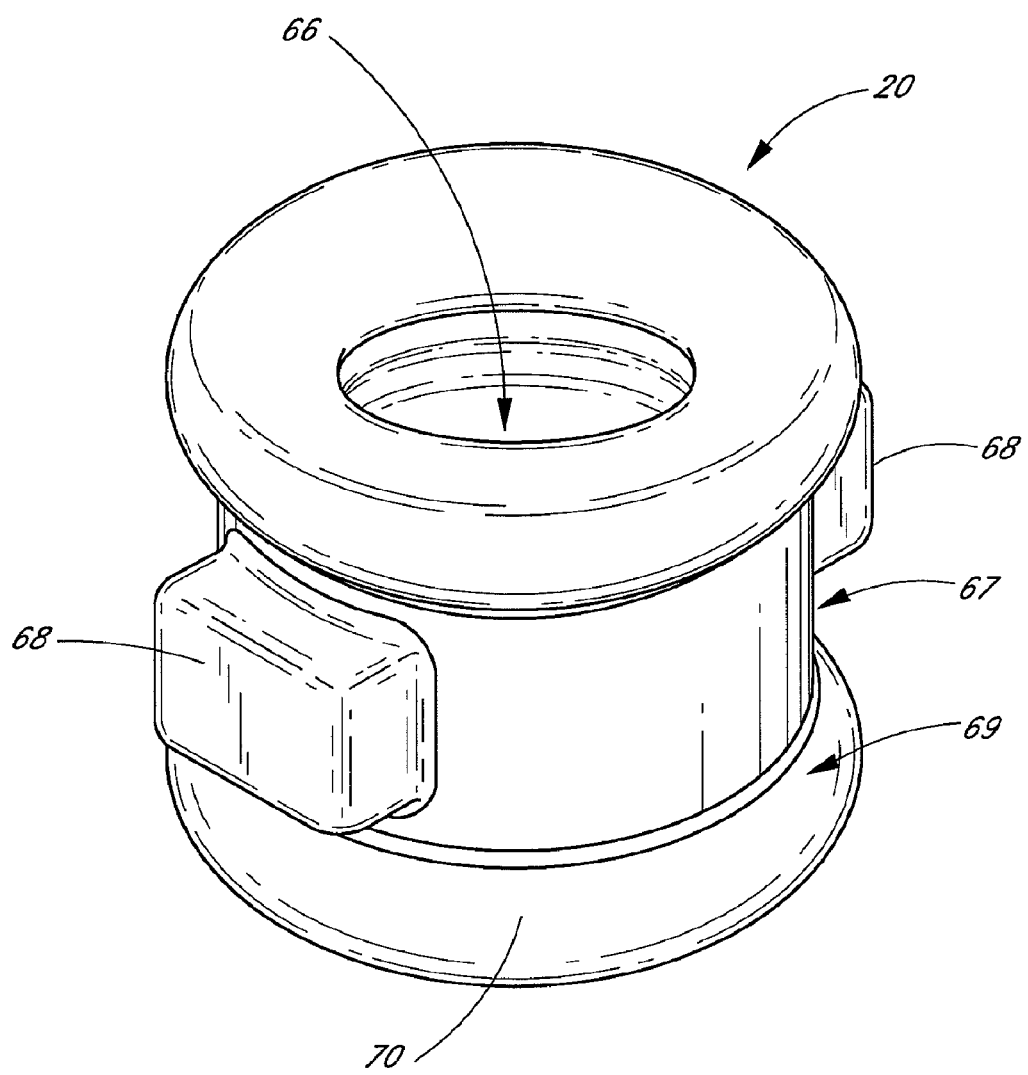
FIG. 6 shows a perspective view of a sealing portion of the connector of FIG. 2. The relative size of the sealing portion is increased in comparison with the components of the connector shown in other figures to facilitate viewing.

Turing now to FIG. 6, the sealing portion 20 is described in greater detail. In some embodiments, the sealing portion 20 is substantially cylindrical and has a bore 66 extending therethrough. In some embodiments, the sealing portion 20 further comprises a pair of generally rectangular protrusions 68 extending from the sidewalls of the cylindrical portion at diametrically opposed positions. The protrusions 68 can have different shapes and/or positions. The sealing portion 20 can also have a generally smaller-diameter middle portion 67 surrounded by two rings 69 at either end with larger diameters.

The sealing portion 20 can be constructed from a number of different materials. In some embodiments, the sealing portion 20 is made from a silicon-based deformable material 70. Silicon-based deformable materials are among those that form fluid-tight closures with plastics and other rigid polymeric materials. The sealing portion 20 can be made from the same material as the resilient member 18.

Figure 7:
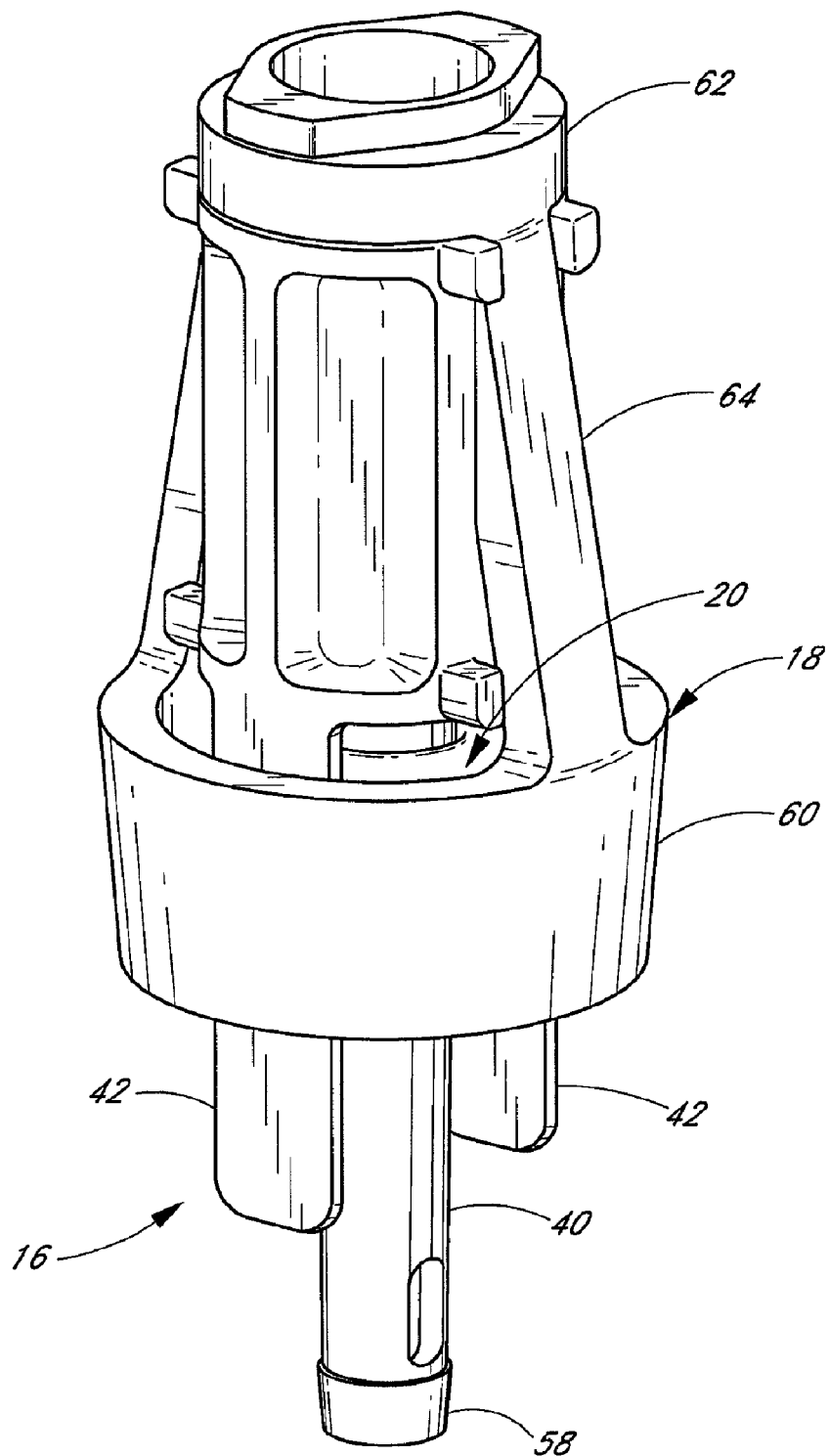
FIG. 7 shows a perspective view of certain components of the connector of FIG. 2 in a partially assembled configuration. The housing portion of FIG. 5 is not shown in FIG. 7.

In FIG. 7, certain components of the male luer 10 of an embodiment are shown. As illustrated, the housing 23 is omitted. The valve member 16, the resilient member 18, and the sealing portion 20 are shown in their respective assembled locations.

Certain interconnections between the various portions of the male luer 10 will now be discussed in further detail. As shown, the smaller ring 62 of the resilient member 18 fits within the circumferential channel 54 of the valve member 16. In some embodiments, the smaller ring 62 can be stretched until it has a larger inner diameter than the raised tabs 49 at the first end of the valve member 16. Once the small ring 62 has been advanced into position about the circular channel 54, it can be released, so that it wraps tightly about the circular channel 54, as shown.

The larger ring 60 of the resilient member 18 extends around the middle portion 32 of the housing 23 (as shown in FIG. 2), and can be stretched and positioned in a manner similar to that described above with respect to the small ring 62. The elastic members 64 of the resilient member 18 can then extend between the small ring 62 and the larger ring 60 of the resilient member 18 and preferably extend along and within the channels 46 in the valve member 16. Once located within these channels, the elastic members 64 are, in effect, trapped by the protrusions 44 along the channel outer walls. As seen in FIG. 2, the elastic members 64 can also extend along the gaps 38 in the upper housing 34 of the housing 23. The gaps 38 are generally located above the channels 46 in the illustrated embodiment. The resilient member 18 thereby provides an elastic connection between the housing 23 and valve member 16, pulling the valve member 16 into engagement with the housing 23.

The sealing portion 20, which is partially hidden by the resilient member 18 in FIG. 7, preferably fits snugly around the tube 40 and lies in between the struts 42 of the valve member 16.

Figure 8:
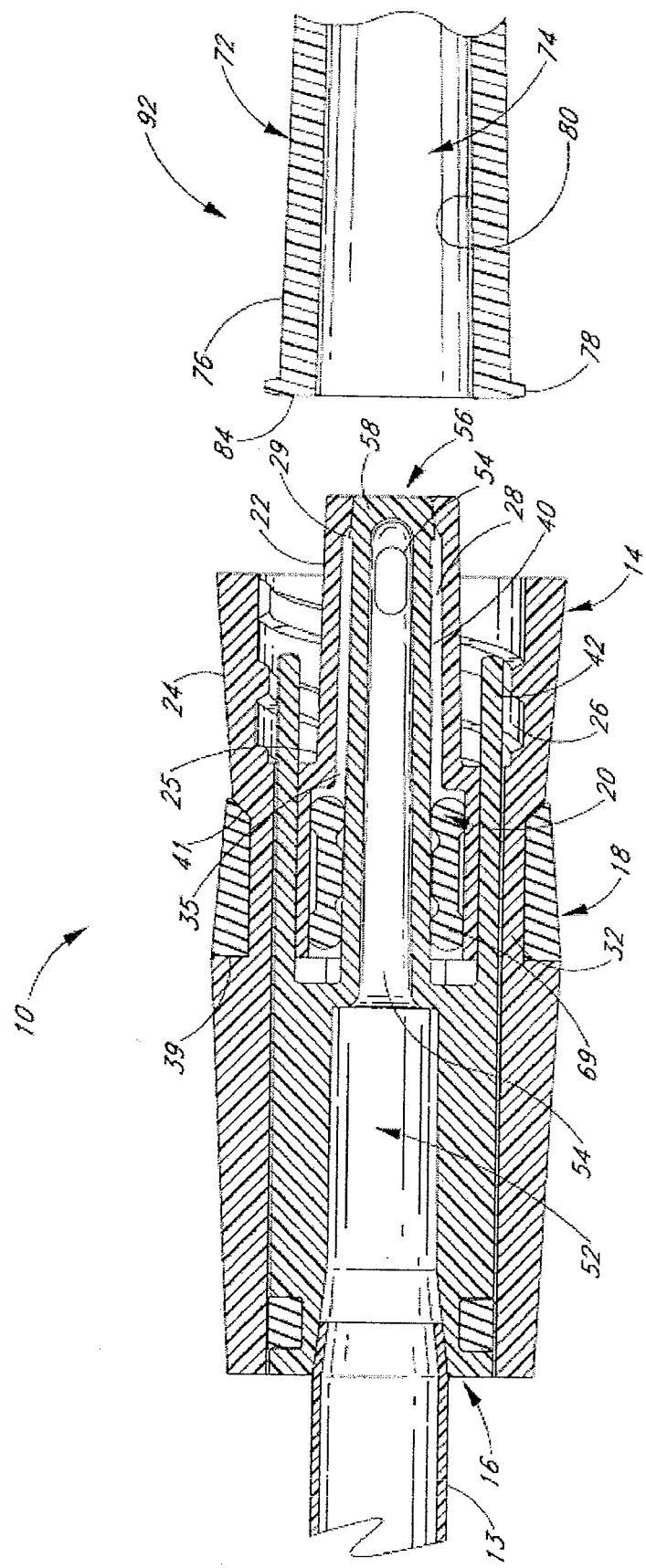
FIG. 8 shows a cross-sectional view of the connector of FIG. 2 adjacent a female portion of another medical implement. At this stage, fluid is impeded through the connector of FIG. 2.

FIG. 8 illustrates a cross-section of the male luer of the present embodiment adjacent an exemplary female connector 92. In this cross-sectional view, the interconnections and interactions between the housing 23, valve member 16 and sealing portion 20 can be seen in greater detail. The valve member 16 is configured to be positioned within the housing 23. As illustrated, the tube 40 of the valve member 16 can be inserted into and through the lumen 28. Meanwhile, the struts 42 are configured to pass through corresponding slots that extend lengthwise through the middle portion 32 of the housing 23. In an assembled configuration, the struts 42 are adjacent to the tip 22 along two sides, and the tube 40 is at least partially contained within the tip 22. The protrusions 44 are captured within the gaps 38 formed in the upper housing 34 of the housing 23.

A closing mechanism 56 is adapted to close the fluid passage extending through the closable male luer 10 from fluid communication with the external environment, preferably whenever the male luer 10 is not engaged with the female connector 92. In the illustrated embodiment, the fluid passageway 52 comprises the lumen 28 as well as the passage 54 of the valve member 16. The closing mechanism 56 of the illustrated embodiment comprises both the flange section 58 of the tube 40 and the internal taper of the raised portion 29 of the lumen 28. As these two surfaces contact, they can form a closure at or near the second end 20 of the male luer 10.

The substantially matched internal tapering surfaces of the raised portion 58 of the tube 40 and the raised portion 29 of the lumen 28 assist in providing closure of the female connector 92. Preferably a relatively fluid-tight closure is formed. The engagement between the raised portions 29 and 58 can also be created in a number of other ways. In some embodiments, the material of the flange section 58 and the material of the raised portion 29 of the lumen 28 are configured to fit closely together, and are made of sufficiently compatible materials, to form a fluid-tight closure. In other embodiments, the flange section 58, and/or additional portions of the valve member 16, can be constructed from a deformable material that more closely follows the contours of the internal surface of the lumen 28, and the lumen 28 need not have a taper. The sealing portion 20 is configured, in some embodiments, to prevent fluid from escaping from within the male luer connector 10. When the valve member 16 engages the housing 23, the sealing portion 20 sits between the middle portion 32 of the housing 23 and the tube 40. When fluid flows within the lumen 28 of the housing 23 and along the outer surface of the tube 40, the fluid is prevented from flowing past the middle portion 32 by the sealing portion 20, and more particularly by the rings 69 at either end of the sealing portion 20.

The sealing portion 20 is preferably held in position between the housing 23 and valve member 16 by the protrusions 68 (see FIG. 6) configured to fit within the holes 36 in the middle portion 32 of the housing 23. The protrusions 68 help to maintain the sealing portion 20 in proper alignment.

With reference to the embodiment illustrated in FIG. 8, the structure of an exemplary female connector 92 will now be discussed in further detail. The female connector 92 can comprise an elongate body 72 having a fluid passageway 74 therethrough, and the female connector 92 can have a tip 76 near its distal end. In some embodiments, the tip 76 of the female connector 92 has a radially extending surface 78 disposed on its external surface. The female connector 92 can have a fluid conduit positioned within the female connector 92. The fluid conduit is not included or required in all female connectors compatible with the connectors 10 disclosed herein. Along a proximal inner surface 80 of the female connector 92, the fluid passageway 74 is preferably tapered such that the diameter of the fluid passageway 74 decreases in the distal direction.

As shown in FIG. 8, the housing 23, the valve member 16, the resilient member 18, and the sealing portion 20 are in an assembled configuration, in which the closing mechanism 56 forms a closing engagement between the flange section 58 and the interior of the lumen 28. In addition, the sealing portion 20 is in closing engagement between the valve member 16 and the housing 23. Fluid from the passage 50 can flow through the windows 54 of the tube 40 of the valve member 16. In this position, the windows 54 communicate with the interior of the tip 22, but not yet with the external environment. The lumen 28 is closed at its second end by the closing mechanism 56 and at its first end by the sealing portion 20.

As shown in FIG. 8, the struts 42 of the valve member 16 extend through slots in the housing 23 such that their ends extend to positions near the end of the shroud 24 toward the second end of the connector. These struts 42 are configured to engage the proximal ends 84 of the female connector 92 as the female connector 92 advances into engagement with the closable male luer 10.

In FIG. 8, the male and female luers are shown in an unengaged configuration. To engage the male luer 10 and female connector 92, the radially extending surface 78 of the female connector 92 are screwed into the inner threads 26 of the male luer 10.

Figure 9:
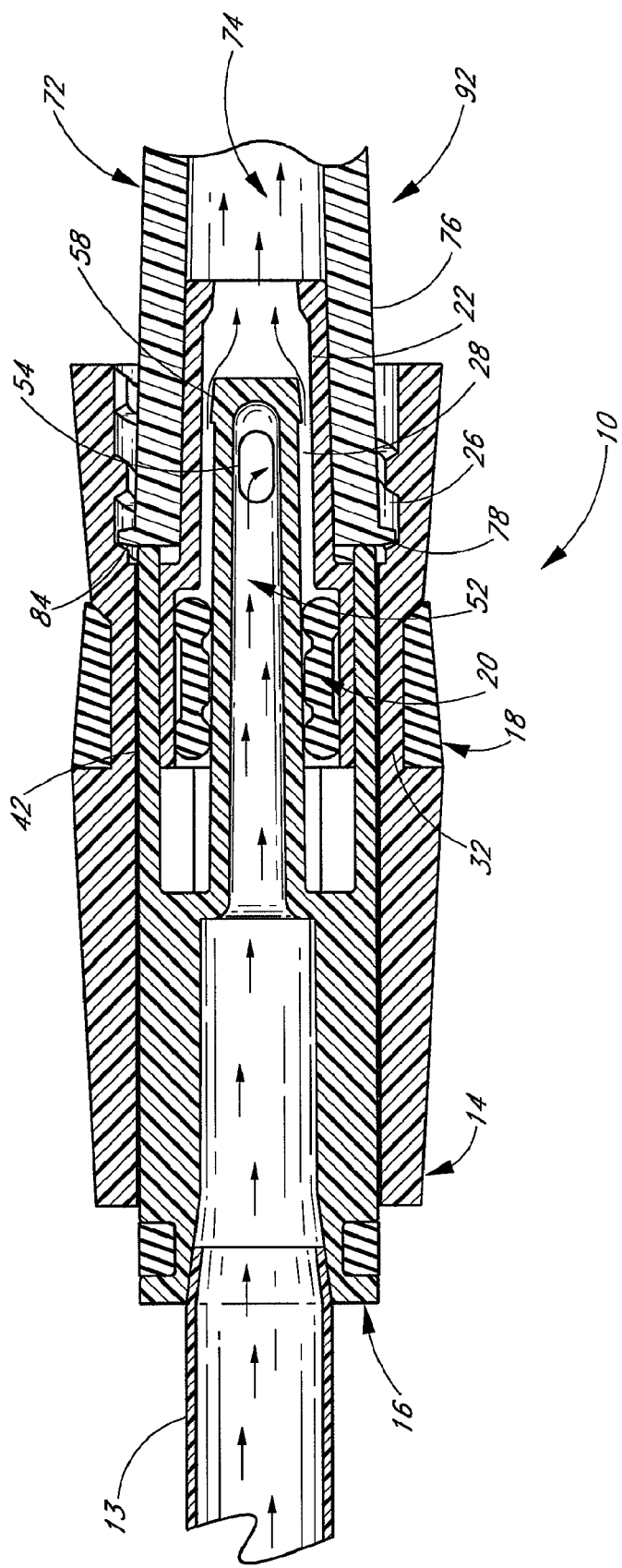
FIG. 9 shows a cross-sectional view of the connector of FIG. 2 in engagement with the medical implement of FIG. 8. Fluid is flowing through the engaged connectors.

As shown in FIG. 9, the two luers can be threadedly engaged towards one another until the taper of the inner surface 80 of the female connector 92 lies adjacent the correspondingly tapered external surface of the tip 22. In other embodiments, the two luers can be threadedly engaged until the second end of the tip 22 forms a closure with a corresponding surface (not shown) of the female connector 92.

As the male luer connector 10 and female connector 92 move towards each other into threaded engagement, the proximal end 84 of the tip of the female connector 92 contacts the struts 42 of the valve member 16. As the male luer connector 10 and female connector 92 move further into threaded engagement, the struts 42, and thereby the valve member 16, are moved in the direction of the first end of the male connector by the female connector 92, displacing the valve member 16 relative to the housing 23. Thus, the flange section 58 moves from the second end of the tip 22 of the housing 23 towards the first end of the male connector. As these two tapered surfaces separate, a space forms between the valve member 16 and the housing 23 and fluid is allowed to pass through the hole 30 into the fluid passageway 74 of the female connector 92, or vice versa. When used with some embodiments of the female connector 92, an internal fluid conduit contacts the second end of the valve member 16 before the housing of the female connector 92 contacts the struts 42 to open the male connector 10. In some embodiments, the closure remains intact until the inner surface 80 of the tip of the female connector 92 has formed a closing engagement with the outer surface of the tip 22 of the male luer 10. Thus, the passage 50 of the male luer 10 need not be in fluid communication with the external environment.

As the valve member 16 moves relative to the housing 23, the elastic members 64 (not shown in FIG. 9) of the resilient member 18 distend and exert a restoring force. As long as the female connector 92 engages the male luer 10, this restoring force can be resisted by the radially extending surface 78 of the female connector 92 contacting the inner threads 26 of the housing 23. However, when the female connector 92 is withdrawn from the male luer 10, the resilient member 18 returns the valve element of the valve member 16 to closing engagement with the lumen 28.

Despite the relative movement between the housing 23 and the valve member 16, the sealing portion 20 preferably maintains a fluid barrier between the outer surface of the tube 40 and the inner surface of the lumen 28. In some embodiments, the position of the sealing portion 20 is maintained by the protrusions 68. In other embodiments, the sealing portion 20 can be positioned by gluing the outer surface of the deformable material 70 to the inner surface of the lumen 28 of the housing 23. Other means of fixing the sealing portion 20 can also be used.

As shown in FIG. 9, in the opened configuration, the fluid passageway 74 of the female connector 92 can fluidly communicate with the passage 50 of the valve member 16. Fluid can thereby flow from tubing 13 attached to the male luer 10, into the passage 50 of the valve member 16, through the windows 54 into the lumen 28, out from the lumen 28 through the hole 30 at the second end of the tip 22 into the fluid passageway 74 of the female connector 92, and vice versa. Fluid is prevented from escaping the male luer 10 through the gap between the housing 23 and valve member 16 by the sealing portion 20. A fluid-tight closure can also be formed between corresponding tapers of the tip 22 of the housing 23 and the inner surface 80 of the female connector 92.

Figure 10:
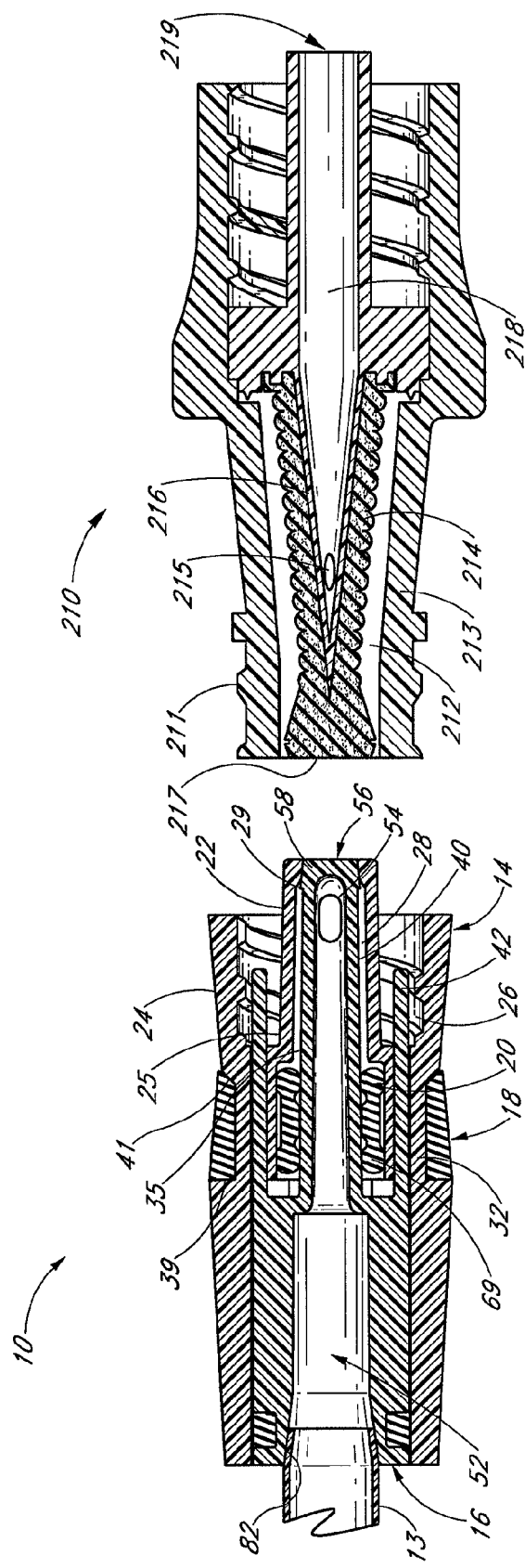
FIG. 10 shows a cross-sectional view of the connector of FIG. 2 adjacent another medical implement with a closeable female luer connector. At this stage, fluid is impeded through the connector of FIG. 2 and the female luer connector.

Turning to FIG. 10, the connector 10 is displayed adjacent to a closeable female luer connector 210. In the sample embodiment illustrated here, the closeable female luer connector 210 comprises an outer housing 213, a void space 212, a fluid passageway 218, a fluid conduit 216 with one or more holes 215, a compressible seal element 214 with a proximal surface 217, and a threaded engagement region 211. The closeable female connector 210 is positioned with its proximal end adjacent the second end 56 of the male connector 10. The threaded engagement region 211 of the closeable female connector 210 can conform to standard sizing for luer connectors, such as those that meet ANSI standards. The compressible seal element 214 can be composed of water-impermeable, resilient material which can reduce in size when a force is exerted upon it. The fluid conduit 216 can be composed of a rigid material, such as polycarbonate plastic, which is capable of resisting deformation when a force sufficient to compress the seal element 214 is exerted upon the closeable female connector 210. The fluid passageway 218 can place the fluid conduit 216 in fluid communication with the second end 219 of the closeable female connector 210. At least one hole 215 in the fluid conduit 216 can be sealed by the compressible seal element 214 to prevent the fluid passageway 218 from being in fluid communication with the void space 212 between the compressible seal element 214 and the inner wall of the housing 213 and/or with the exterior of the housing 213. The hole or holes 215 can be sized appropriately small enough to permit fluid to pass between the fluid passageway 218 and the void space 212 at an appropriate flow rate. One such size for the hole or holes 215 is approximately one millimeter in diameter, although irregular shapes and other sizes can be used. Holes of at least about 1 mm or approximately 1 mm-3 mm, or less than about 1 mm can also be used. The connector 10 can be engaged with a tubing 13 containing a fluid.

Figure 11:
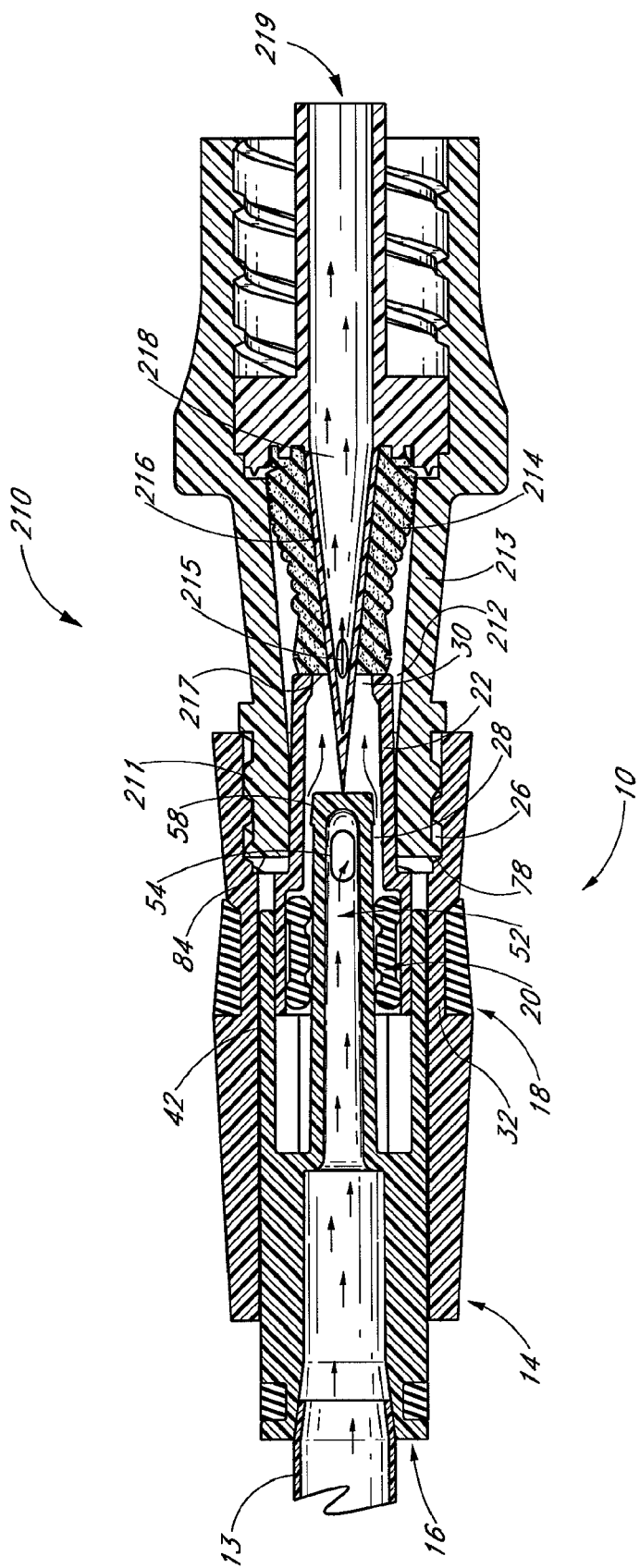
FIG. 11 shows a cross-sectional view of the connectors of FIG. 10 after engagement. Fluid is flowing through the engaged connectors.

With reference to FIG. 11, the connector 10 can be threadedly engaged with the closeable female connector 210. The threaded region 211 of the closeable female connector 210 can engage with the inner threads 26 of the male connector 10 to engage the connectors 10, 210, as illustrated. In the illustrated engagement, the luer tip 22 advances into the closeable female connector 210 by compressing the compressible seal element 214. As can be seen, the luer tip 22 contacts the compressible seal element 214 on the proximal surface 217 of the compressible seal element 214. The force exerted to engage the connectors 10, 210 and engage the threaded regions 26, 211 is sufficient to compress the seal element 214 to expose the holes 215 in the fluid conduit 216. With the seal element 214 compressed, the fluid passageway 218 is in fluid communication with the interior space of the luer tip 22.

As the luer tip 22 advances further into the closeable female connector 210, the fluid conduit 216 contacts the end of the valve member 16 towards the second end of the male connector. The valve member 16 is displaced towards the first end of the male connector by the contact and continued advancement of the luer tip 22. The resilient member 18 exerts a closing force in a direction towards the second end of the male connector on the valve member 16. As a result, the tip of the valve member 16 towards the second end of the male connector generally maintains contact with the fluid conduit 216 throughout the engagement. As the valve member is moved in a direction towards the first end of the male connector, the flange section 58 of the valve member 16 separates from the interior surface of the housing 23 through which the hole 30 passes. As a result, the windows 54 are opened to fluid communication with the closeable female connector 210. The compressed seal element 214 inhibits fluid flow into the interior of the closeable female connector 210 beyond the luer tip 22. In this configuration, fluid can flow from the tubing 13 at the end of the valve member 16 toward the second end of the male connector and into the tube 40 through the windows 54 into the interior of the lumen 28, out the hole 30 in the luer tip 22, into the interior of the outer housing 213 of the closeable female connector 210, in the holes 215 of the fluid conduit 216 and into the fluid channel 217 in the interior of the fluid conduit 216. Thus, the second end of the connector 210 is placed in fluid communication with the proximal end 219 of the closeable female connector 210. Additionally, the sealing portion 20 preferably maintains a fluid barrier between the outer surface of the tube 40 and the inner surface of the lumen 28, confining the flow of fluid towards the closeable female connector 210. When the surface of the valve member towards the second end of the connector is directly contacted by a female connector member such as the fluid conduit 216, the struts 42 may not be engaged by the female connector.

The connectors 10, 210 can be threadedly disengaged. During engagement, the force exerted by the resilient member 18 can return the connector 10 to its pre-engaged state by directing the valve member 16 to engage the flange section 58 of the end of the valve member 16 toward the second end of the male connector with the internal surface of the luer tip 22. Likewise, the resilient material of which the compressible seal is composed can return to its shape in the closed position and the proximal surface 217 can seal the proximal tip of the closeable female connector 210.

Figure 12:
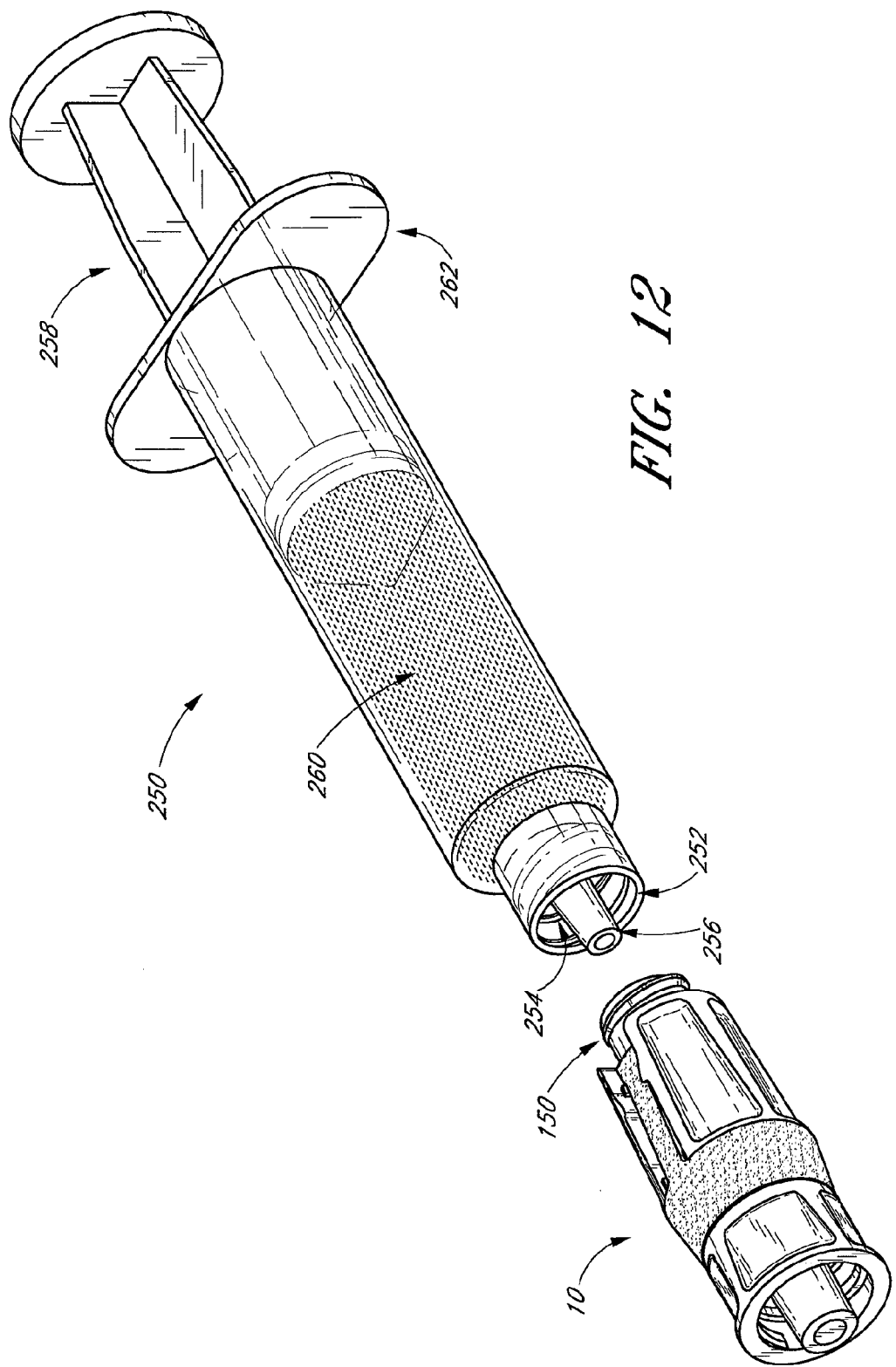
FIG. 12 shows a perspective of the connector of FIG. 2 adjacent a syringe with a male luer tip. At this stage, fluid is impeded through the connector.

Referring now to FIG. 12, the connector 10 can be engaged with a syringe 250. In FIG. 12, the syringe 250 and connector 10 are displayed adjacent to each other. The syringe can comprise a male luer connector 252, a plunger 258, a reservoir 260, and convenient finger anchors 262. The luer connector 252 can further comprise an internally threaded shroud 254 and a syringe luer tip 256. In the illustrated embodiment of the connector 10, a threaded surface 150 is disposed on the outside surface of the first end of the valve member 16.

Figure 13:
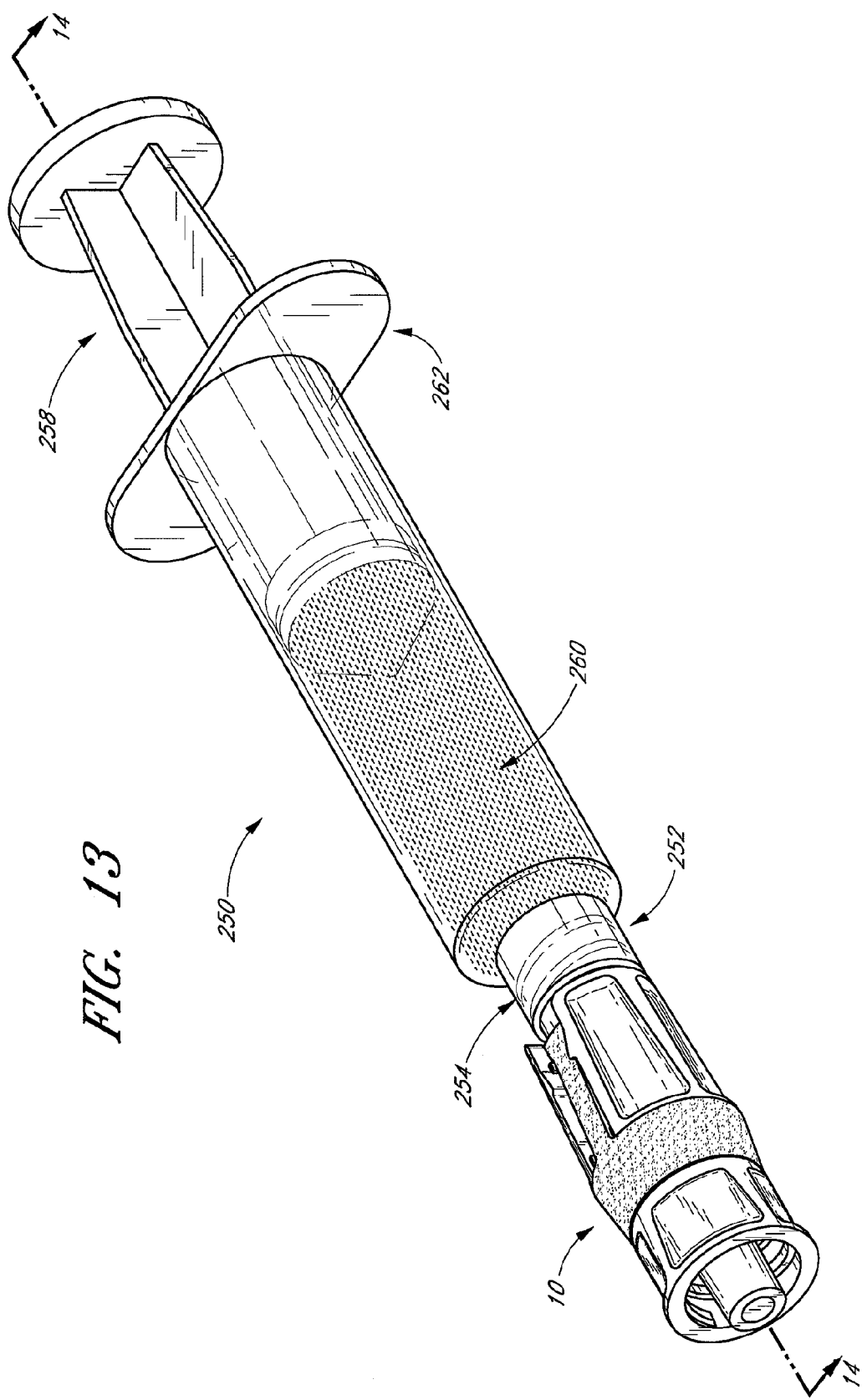
FIG. 13 shows a perspective view of the components of FIG. 12 after engagement. At this stage, fluid is still impeded through the connector.

With reference now to FIG. 13, the connector 10 can be threadedly engaged with the syringe 250. The shroud 254 can engage with the end 16 of the valve member toward the first end of the connector to connect the connector 10 to the syringe 250. The reservoir 260 of the syringe 250 can be placed in fluid communication with the tube 40 interior to the valve member 16.

Figure 14:
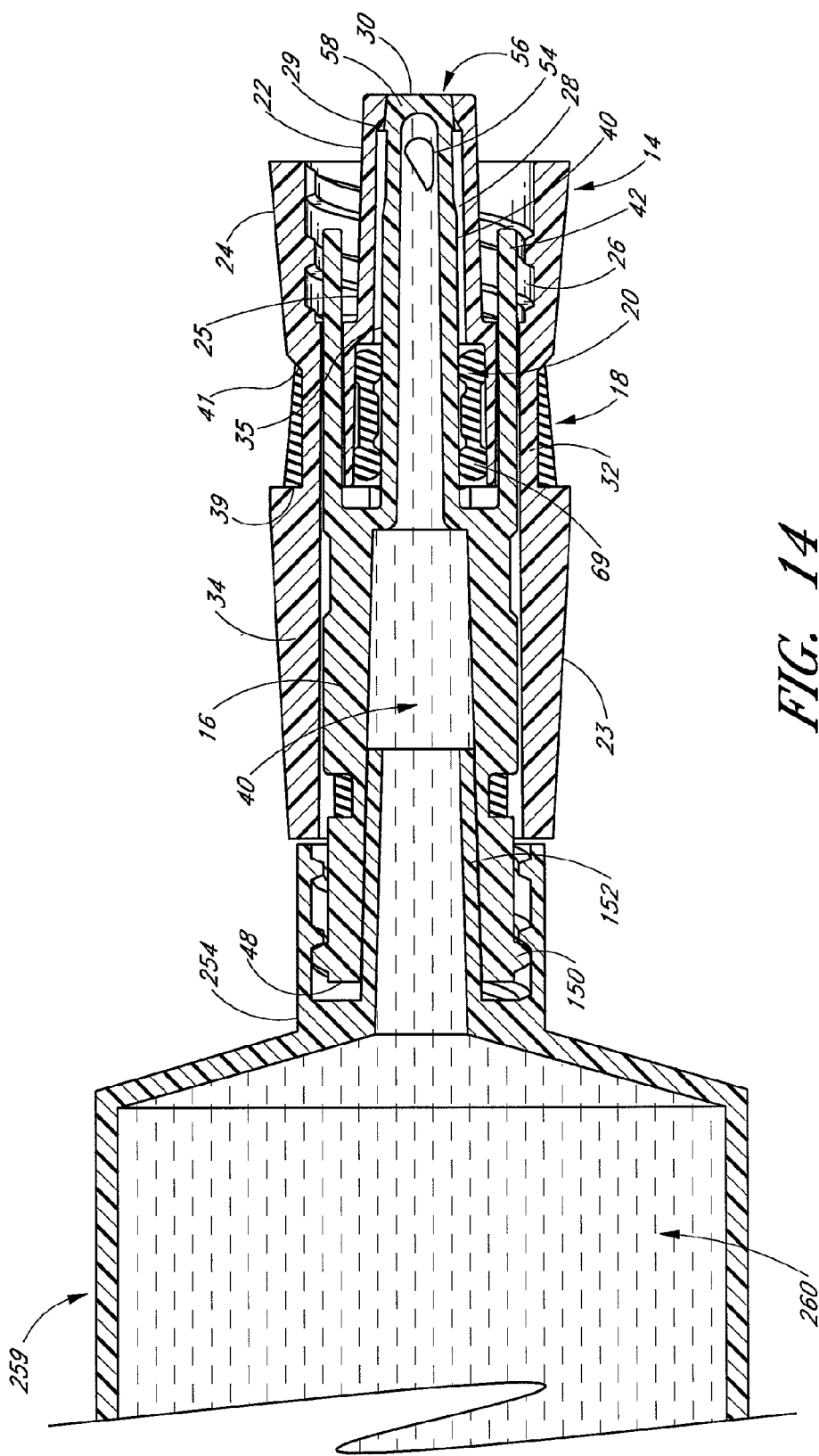
FIG. 14 shows a cross-sectional view of the connector and the male luer tip of the syringe of FIG. 13.

Turning to FIG. 14, the engagement illustrated in FIG. 13 is shown in a cross-sectional view. The syringe 250 is threadedly engaged with the connector 10 by the engagement between the shroud 254 and the threaded surface 150 of the valve member 16. The luer tip 252 of the syringe 250 is extended into the tube 40 of the valve member 16. The reservoir 260 of the syringe, shown here with a fluid in the reservoir 260, is in fluid communication with the interior of the valve member 16. The fluid can pass through the tube 40 and towards the luer tip 22 of the connector 10. In the illustrated embodiment, the fluid cannot exit the connector 10 out its male luer tip 22 because the flange section 58 is in contact with the interior surface of the lumen 28. Accordingly, the hole 30 in the tip of the housing 23 towards the second end of the connector is blocked by the valve member 16. In order for the syringe 250 and connector 10 to transition from the stage shown in FIG. 12 to the stage shown in FIG. 14, the valve member 16 may need to be temporarily opened to release air (as described in more detail below).

Figure 15:
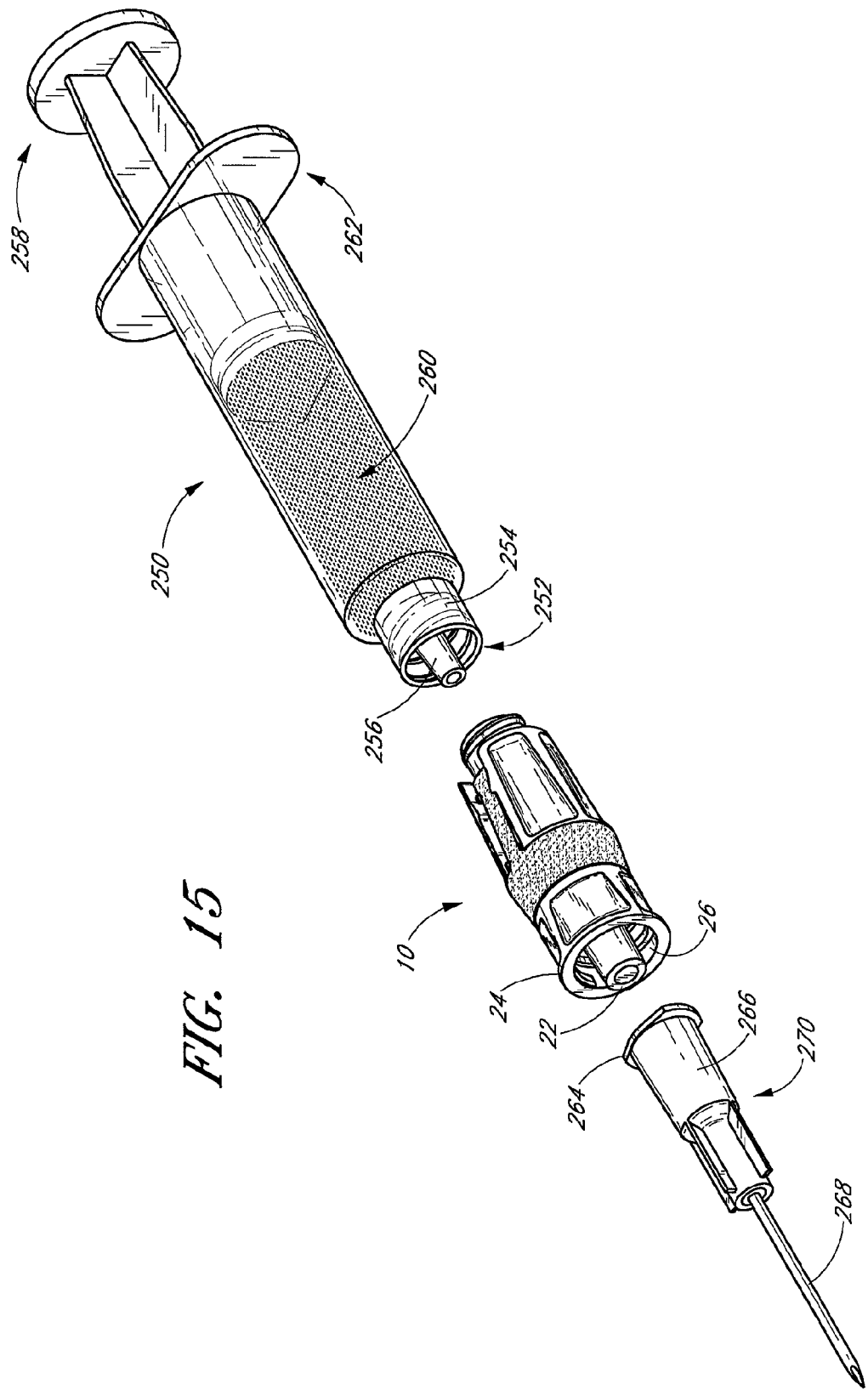
FIG. 15 shows a perspective view of the a closeable male luer connector located with its first end adjacent a syringe with a male luer tip and with its second end located adjacent a hypodermic needle with a female luer attachment portion.

Referring to FIG. 15, the connector 10 is shown adjacent to and between a syringe 250 and a hypodermic needle with sheath 270. The syringe 250, like that of FIG. 12, can comprise a male luer connector 252, a plunger 258, a reservoir 260, and convenient finger anchors 262. The luer connector 252 can further comprise an internally threaded shroud 254 and a syringe luer tip 256. The needle with sheath 270 can comprise a housing 266 with raised tabs 264 on the engagement end and a needle 268.

Figure 16:
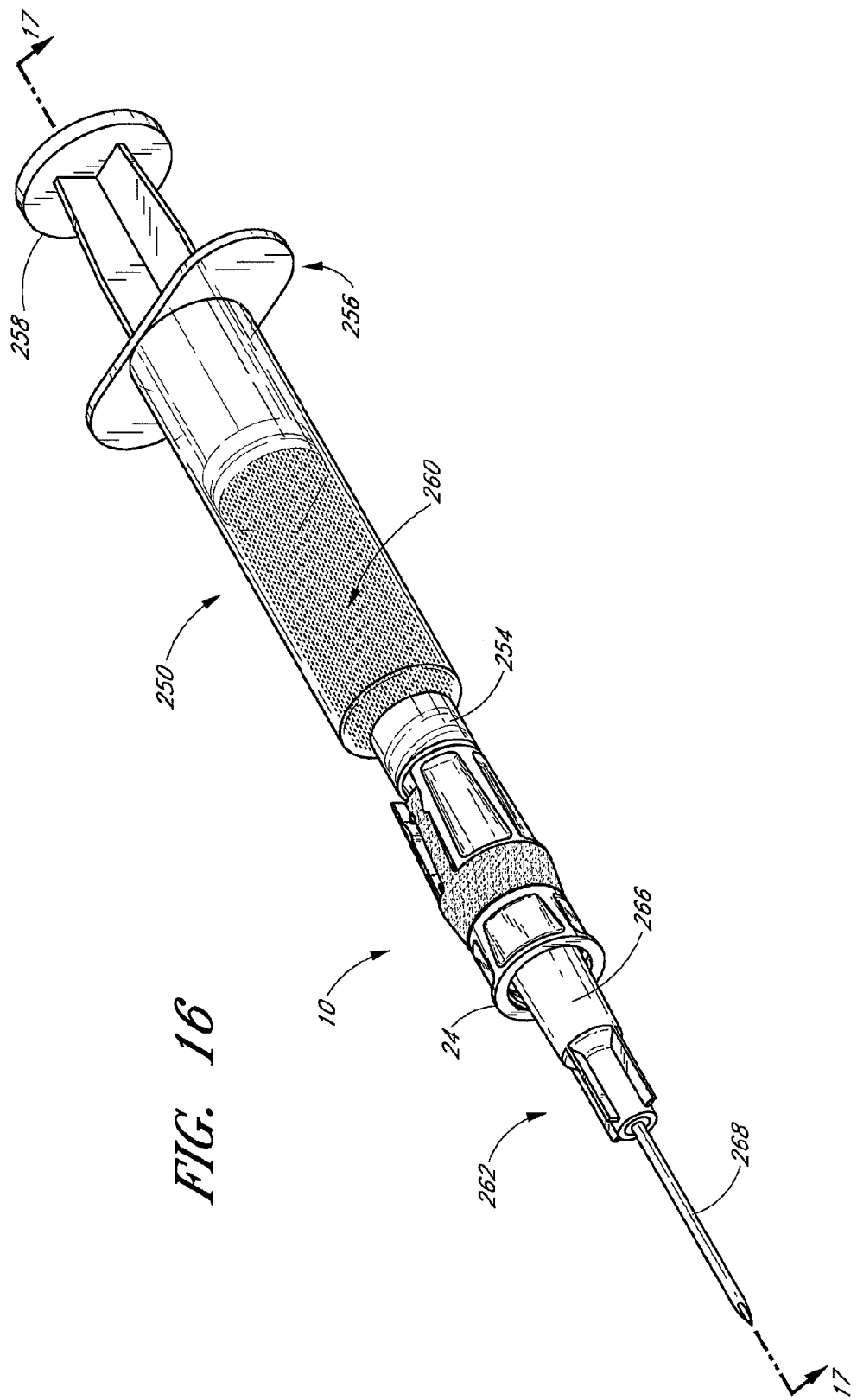
FIG. 16 shows a perspective view of the components of FIG. 15 in engagement. At this stage, fluid can flow through the connector.

With reference to FIG. 16, the connector 10 is shown threadedly engaged with both the syringe 250 and needle with sheath 270. The threaded surface 150 of the valve member 16 of the connector 10 can engage with the threaded shroud 154 of the syringe 250. Accordingly, the luer tip 256 can protrude into the tube 40 of the valve member 16. Similarly, the raised tabs 264 can engage with the inner threads 26 of the shroud 24 of the connector 10. The luer tip 22 of the connector 10 can protrude into the housing 266 of the needle sheath.

Figure 17:
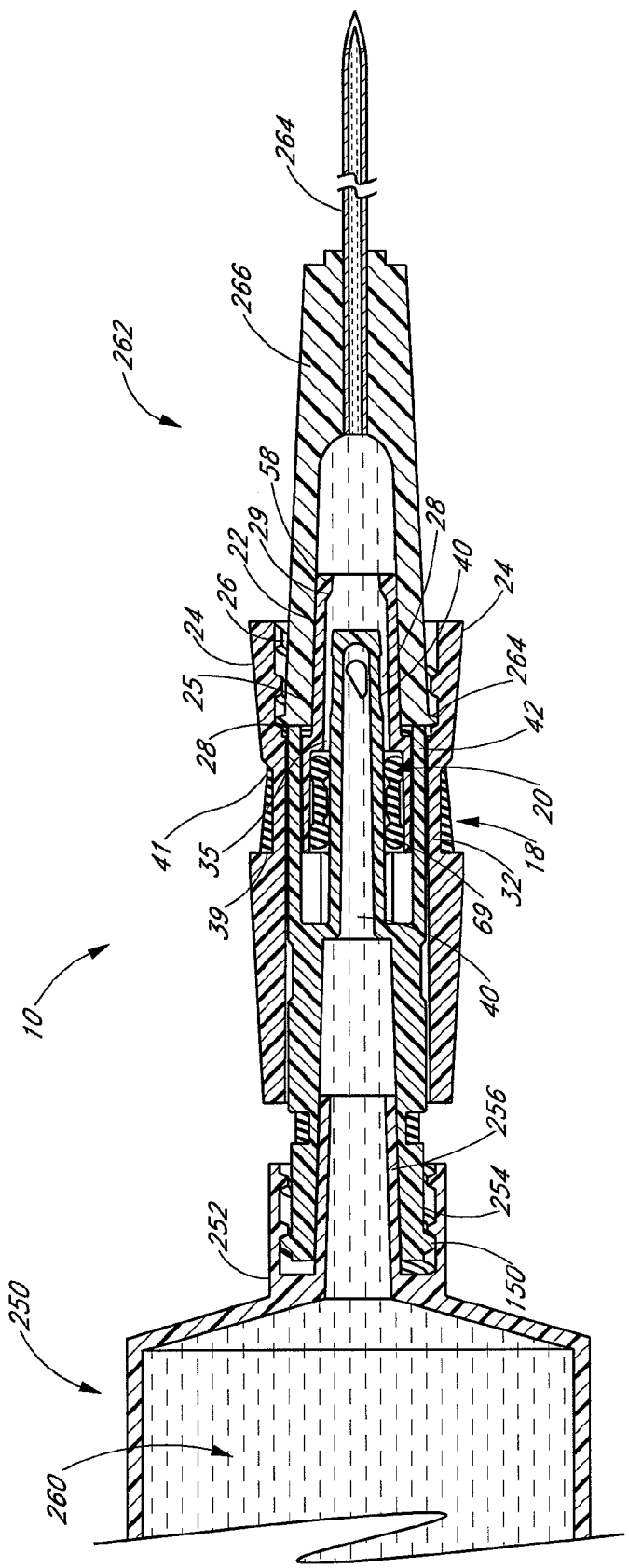
FIG. 17 is a cross-sectional view of the connector, male luer tip of the syringe, and hypodermic needle of FIG. 16. At this stage, fluid can flow through the connector.

In FIG. 17, the engagement shown in FIG. 16 is illustrated in a cross-sectional view. The connector 10 is engaged by a syringe 250 and a needle with a sheath 270. The syringe 250 is threadedly engaged with the threaded surface 150 of the valve member 16 of the connector 10. The needle with sheath 270 is threadedly engaged with the inner threads 26 of the shroud 24.

The luer tip 256 of the syringe 250 protrudes into the tube 40 of the valve member 16. The reservoir 260 of the syringe 250 is in fluid communication with the tube 40 of the valve member 16 through the luer tip 256.

The connector 10 is engaged with the needle with a sheath 270. The housing 266 of the needle with sheath 270 has raised tabs 264 near its proximal end. The raised tabs 264 threadedly engage the inner threads 26 of the shroud 24 of the connector 10. As the luer tip 22 advances into the housing 266 of the needle 268, the proximal end of the housing 266 can contact the struts 42 of the valve member 16. When the needle with sheath 270 is fully engaged with the connector 10, the valve member 16 has been displaced a distance which separates the flange section 58 from the tapered interior wall of the lumen 28 sufficiently to permit fluid to flow out the windows 54 of the valve portion 16. The fluid can then flow out the hole 30 in the end of the luer tip 22 and into the housing 266 of the needle with sheath 270. The hollow needle 268 permits the fluid to flow from within the housing 266 out the distal tip of the needle 268. The sealing portion 20 preferably maintains a fluid barrier between the outer surface of the tube 40 and the inner surface of the lumen 28, confining the fluid in the lumen and the direction of flow toward the hole 30 in the luer tip 22. Thus, at this stage, the syringe 250 is in fluid communication with the distal tip of the needle 268. As was previously illustrated in FIGS. 13 and 14, in some embodiments, the connector 10 will generally not permit fluid to flow out of the syringe 250 without a component engaged with the second end 14 of the connector 10. The component illustrated in FIGS. 15-17 is a needle with a sheath 270; however, other components, such as those which permit fluid flow and possess a female luer engagement portion, can also be used.

Figure 18A:
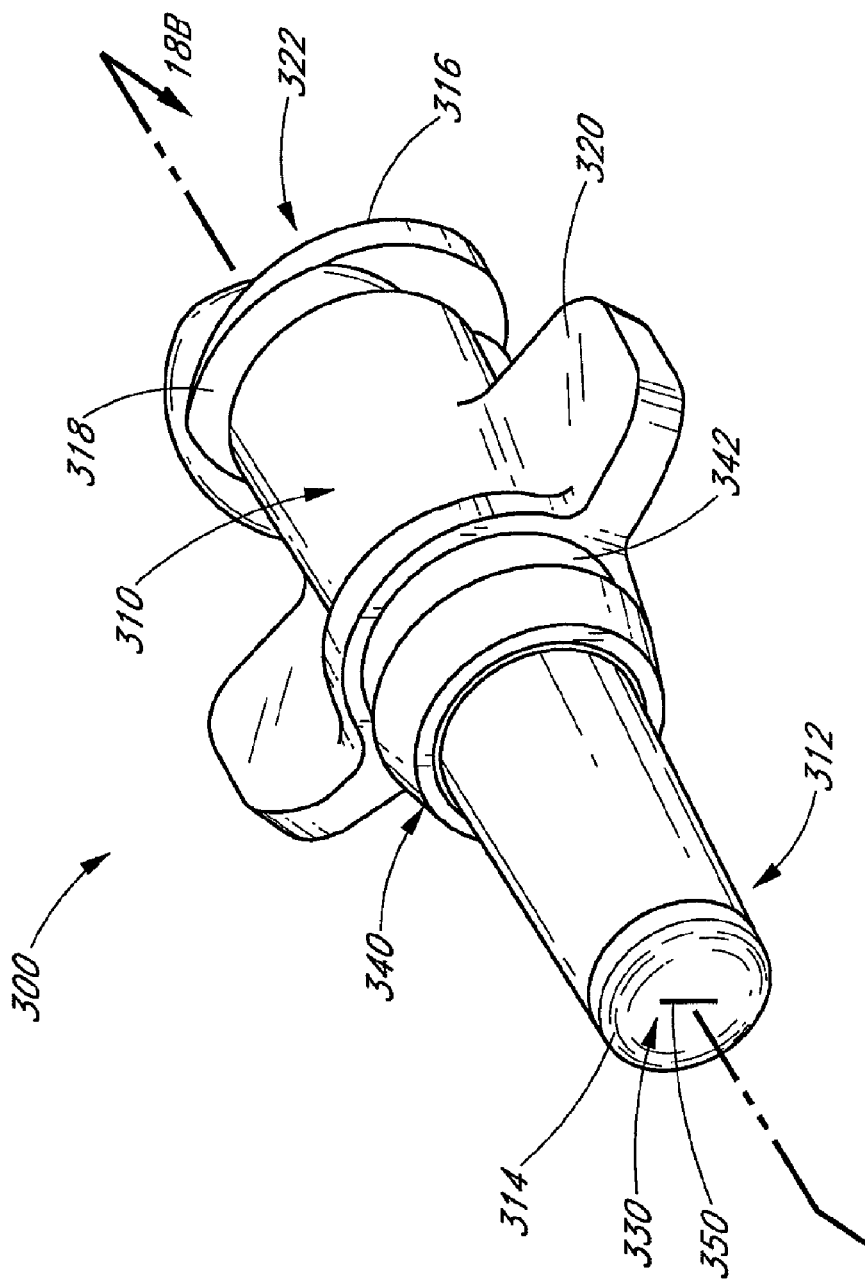
FIG. 18A is a perspective view of another embodiment of a closeable male luer connector.

FIG. 18A displays a perspective view of another embodiment of a closeable male luer. The rotatable connector 300 is comprised of a housing 310, an internal passageway 322 and a seal element 330. The housing is further comprised of a luer tip 312, a luer receiver 316 at the first end of the connector 300, an engagement portion 318, a manipulation portion 320, and a raised portion 340. The seal element 330 can have an opening 350 along its face 314 in a transverse direction. The internal passageway 322 can extend from the luer receiver 316 to the luer tip 312. The housing 310 can be composed of a water-impermeable material, such as a polycarbonate plastic. The housing 310 can also be composed of a hydrophobic plastic. Other examples of materials suitable for construction of the housing 310 are glassed-filled GE Valox 420 or polypropylene. Depending on the application, many other materials can also be used.

The housing 310 illustrated is configured to receive a male luer tip at the luer receiver 316 by threadedly engaging the male luer at its engagement portion 318. The receiver 316 can conform to ANSI standards for a luer receiver. The illustrated manipulation portion 320 has two tabs extending radially from the central axis of the housing 310. The manipulation portion 320 is configured to aid the user in grasping and rotating the connector 300.

The housing 310 illustrated is also constructed to provide a closeable male luer at its second end. The luer tip 312 at the second end can be constructed to ANSI standards for a male luer tip. The luer tip joins the main body of the housing 310 at the raised portion 340. The raised portion 340 is constructed to inhibit the luer tip 312 from advancing too far into a luer receiver. The housing 310 can also have a recessed portion 342 behind the raised portion 340. The luer tip 312 can also have a seal element 330 which has a face 314 towards the second end of the connector. The seal element 330 can be any water-impermeable, resilient material, including without limitation, silicone. The selection of the material for construction of the seal can be accomplished by one skilled in the art. The luer tip 312 can taper smaller in a direction from the raised portion 340 as it approaches its second end.

The seal element 330 can also have an opening 350 in the face 314 toward the second end of the connector prior to engagement with any other component. The opening 350 can be a slit in a transverse direction to the longitudinal axis of the housing 310. The opening 350 can be centered across the face 314, or located in another position on the face 314. The seal element 330 can cover the entire second end of the luer tip 312, or only a portion thereof. The seal element 330 can be attached to the housing by an overmolding process, among other attachment methods. In such an overmolding process, the housing 310 can be formed by injection molding in a first step, and then in a second step, the housing 310 can be re-inserted into a mold (or remain in a mold) and an appropriately sized molding pin (not shown) can be inserted through a wider end of the housing 310, such as the second end. Silicone material can then be injected into the mold to form the seal element 330. In other embodiments, the seal element 330 can be glued or otherwise adhered into the housing 310.

As can be seen from the illustrated embodiment in FIG. 18A, the seal element 330 can inhibit fluid from flowing through the housing 310 when the luer tip 312 is not engaged with another component. Thus, when a fluid-containing component (not shown) with a male luer connector is connected to the luer receiver 316, the connector 300 can be used to control flow of fluid through its luer tip 312. For example, when a fluid-containing component such as a syringe is engaged with the connector 300, fluid is permitted to fill the housing 310 of the connector 300 by flowing through the internal passageway 322, but the seal element 330 can substantially inhibit flow of fluid out the luer tip 312. If the interior space of the housing is filled with air or another gas before the fluid enters, the connector 300 may need to be opened to allow the air or other gas to escape before the fluid can enter. In some embodiments, as described in detail below, the internal surface of the seal element 330 can be adapted to increase the resistance against the widening of the opening 350, which could allow fluid to escape when the fluid (not shown) exerts a pressure against the seal element 330 from the internal passageway 322. Thus, the connector 300 inhibits flow of fluid from a fluid-bearing component when the connector 300 is attached to the male luer of the fluid-bearing component without another component connected to the luer tip 312 of the connector 300.

In some modes of use, the opening 350 on the face 314 of the seal element 330, normally closed in the position shown, can be opened when the luer tip 312 comes in contact with a suitable female connector, such as a Clave® connector sold by ICU Medical, San Clemente, Calif. An illustrated engagement of this configuration is discussed in detail below. The engagement can be achieved in many other ways, and with many other structures, including connectors other than the Clave connector.

FIG. 18B is a cross-sectional view of the connector 300 illustrated in FIG. 18A. The connector 300 can have an internal passageway 322 which connects the luer receiver 316 to the luer tip 312. The engagement portion 318 can be configured to receive an internally threaded shroud of a male luer connector (see FIG. 19). The manipulating portion 320 can extend radially away from the internal passageway 322, as shown. The seal element 330 can extend along at least part of the internal passageway 322, and can be disposed across at least part of the second end of the connector 300. The seal element 330 can extend beyond the end of the luer tip 312. The seal element 330 can have a cross-sectional area approximately equal to the housing 310 at the end of the luer tip 312. In those embodiments where the luer tip 312 and seal element 330 are generally circular, the outside diameter of the seal element 330 can be equal to the outside diameter of the luer tip 312. The seal element 330 is not confined to a circular shape (nor are any other structures disclosed herein), and other shapes can be used. In other embodiments, the seal element 330 does not extend beyond the end of the housing 310 towards the second end of the connector 300, but can have a maximum outer dimension equal to that of the inner dimension of the luer tip 312. The seal element 330 can have a closing portion 324. The closing portion 324 can permit fluid flow through the seal element 330 of the connector 300, but is biased to generally close the opening 350 in the seal element 330. The structure of the closing portion 324 can be adapted to resist permitting fluid (not shown) from exiting the opening 350 when the luer tip 312 is not engaged with another component, as described in further detail below.

As can be seen in FIG. 18C, which is a detail of the cross-sectional view presented in FIG. 18B, the seal element 330 can comprise the entire face of the second end of the connector 300. In other embodiments, the seal element 330 may not extend beyond the housing 300. The internal passageway 322 can extend to the seal at the second end of the connector 300.

Figure 19:
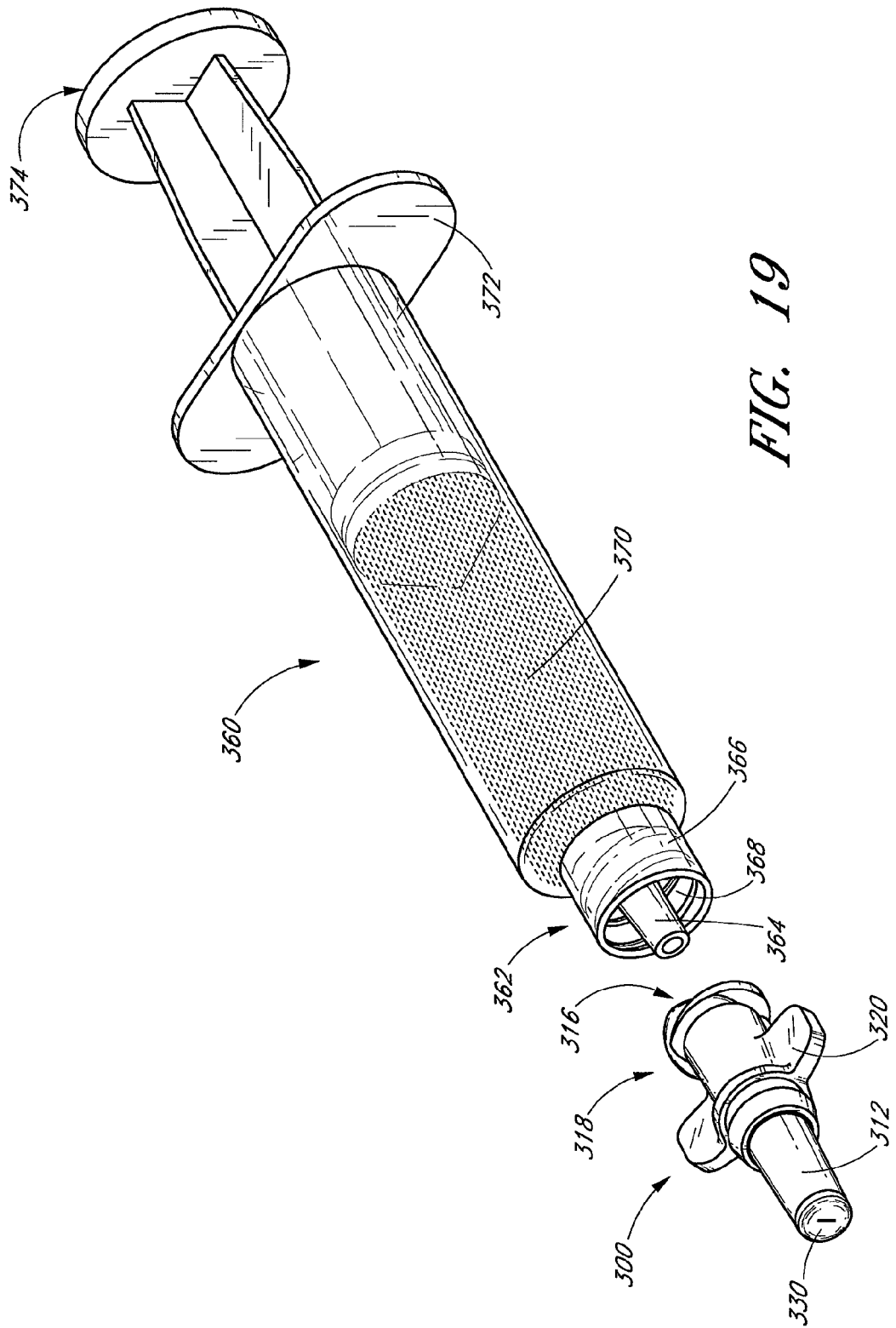
FIG. 19 is a perspective view of the connector of FIG. 18A located adjacent a syringe with a male luer tip.

FIG. 19 illustrates a perspective view of the connector 300 adjacent a syringe 360. As in previous descriptions, the syringe can comprise a male luer connector 362, a fluid reservoir 370, a plunger 374, and finger anchors 372. The luer receiver 316 of the connector 300, which can be of appropriate size and shape to engage with standard luer connectors, is positioned to receive the luer tip 364 of the syringe 360. The internal threads 368 of the shroud 364 of the syringe 360 are properly aligned to threadedly connect with the engagement portion 318. In this way, the receiver 316 can engage the luer connector 362 and connect the connector 300 to the syringe 360. Before engagement of the syringe 360 with the connector 300, the fluid within the reservoir 370 is not inhibited from exiting the luer tip 364 by any physical component.

Figure 20:
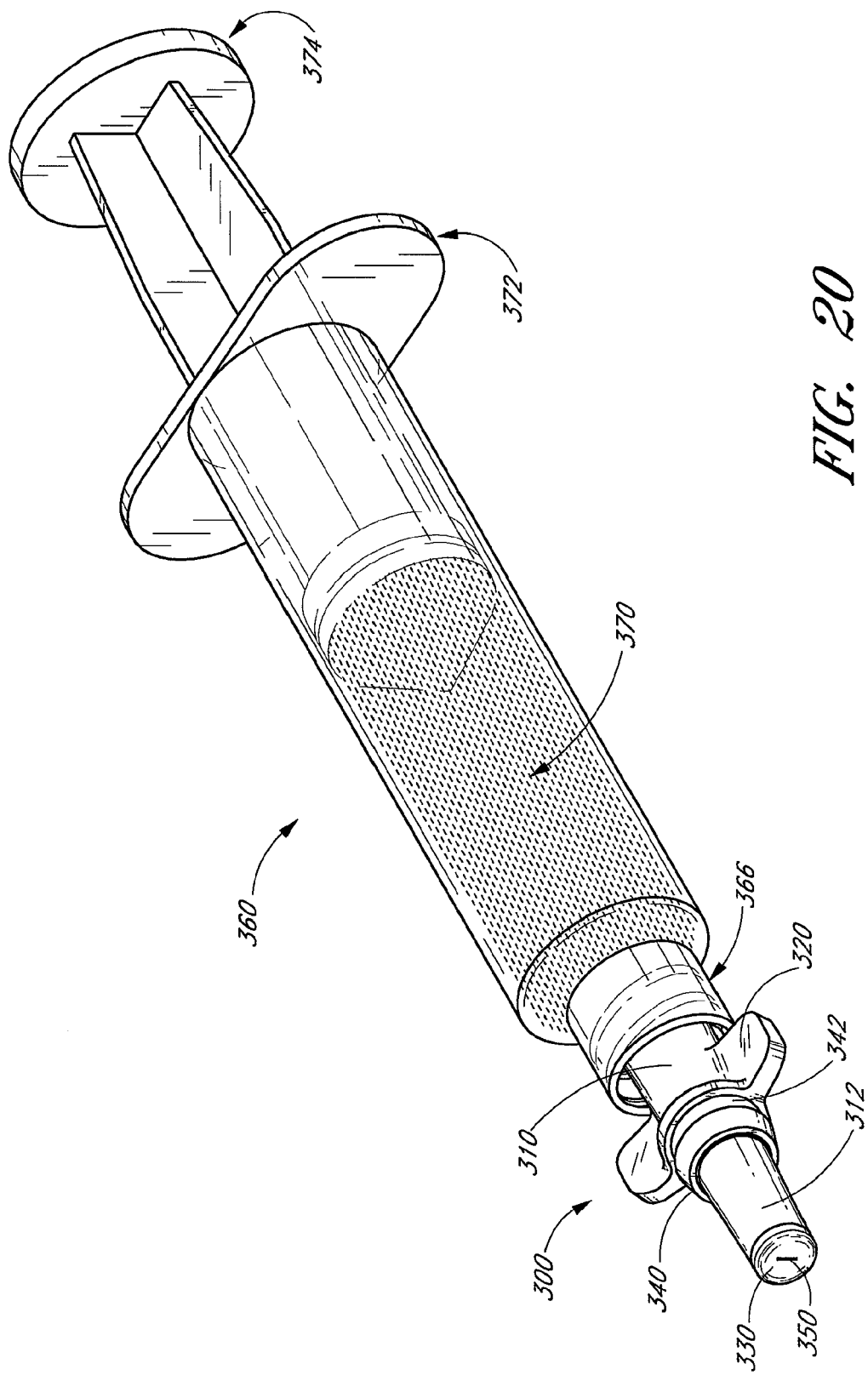
FIG. 20 is a perspective view of the components of FIG. 19 in engagement.

Referring now to FIG. 20, a perspective view of the connector 300 threadedly connected to a syringe 360 is shown. The connector 300 can be connected to the syringe 360, or other medical implement, by many other means, such as glue, adhesive, solvent, ultrasonic welding, epoxy, interference fits, mechanical connections, and/or unitary constructions. The receiver 316 (not shown) contains at least part of the luer tip 364 of the syringe 360. The luer tip 364 extends at least partially into the internal passageway 322. The threaded engagement portion 318 is engaged with the internal threads 368 of the shroud 364 of the syringe 360. Fluid from the reservoir 370 can then flow freely within the housing 310 of the connector 300, by way of the internal passageway 322. If the interior space of the housing is filled with air or another gas before the fluid enters, the connector 300 can be opened to allow the air or other gas to escape before the fluid can enter. In some cases, the housing 310 of the connector 300 may be filled with a gas, such as air. Before the fluid enters the housing 310, the connector may need to be opened to allow the gas to escape before the fluid can flow. The seal element 330 inhibits fluid from leaving the connector 300. The luer tip 312 of the connector 300 can be used to connect the connector-syringe 300, 360 combination to other components for controlled fluid transfer. The connector 300 can also be formed integrally with the syringe 360 (not shown), such that the housing 310 of the connector is formed by the fluid-delivery end of the syringe. During use of this combination connector-syringe, the male luer tip 312 of the connector 300 can, in effect, replace the luer tip 364 of the syringe for connection purposes.

Certain medications, such as chemotherapy medications, are contact toxins, and avoiding exposure to the skin is desirable. Such medications are often stored in a syringe with a hypodermic needle, such as depicted in FIGS. 15 and 16. Under certain conditions, without the use of a closeable male luer connector, it can be possible for the toxic fluid to flow out of the syringe. Even if steps are taken to avoid accidental fluid flow, such as orienting the syringe with attached needle such that gravity aids the retention of the medication within the syringe, the medication can also vaporize and seep out of the hypodermic needle in a gaseous state. The use of a closeable male luer between the syringe and hypodermic needle inhibits the uncontrolled flow of medication, in both liquid and gaseous states. Accordingly, risk of accidental exposure to such toxic medications is minimized.

Figure 21:
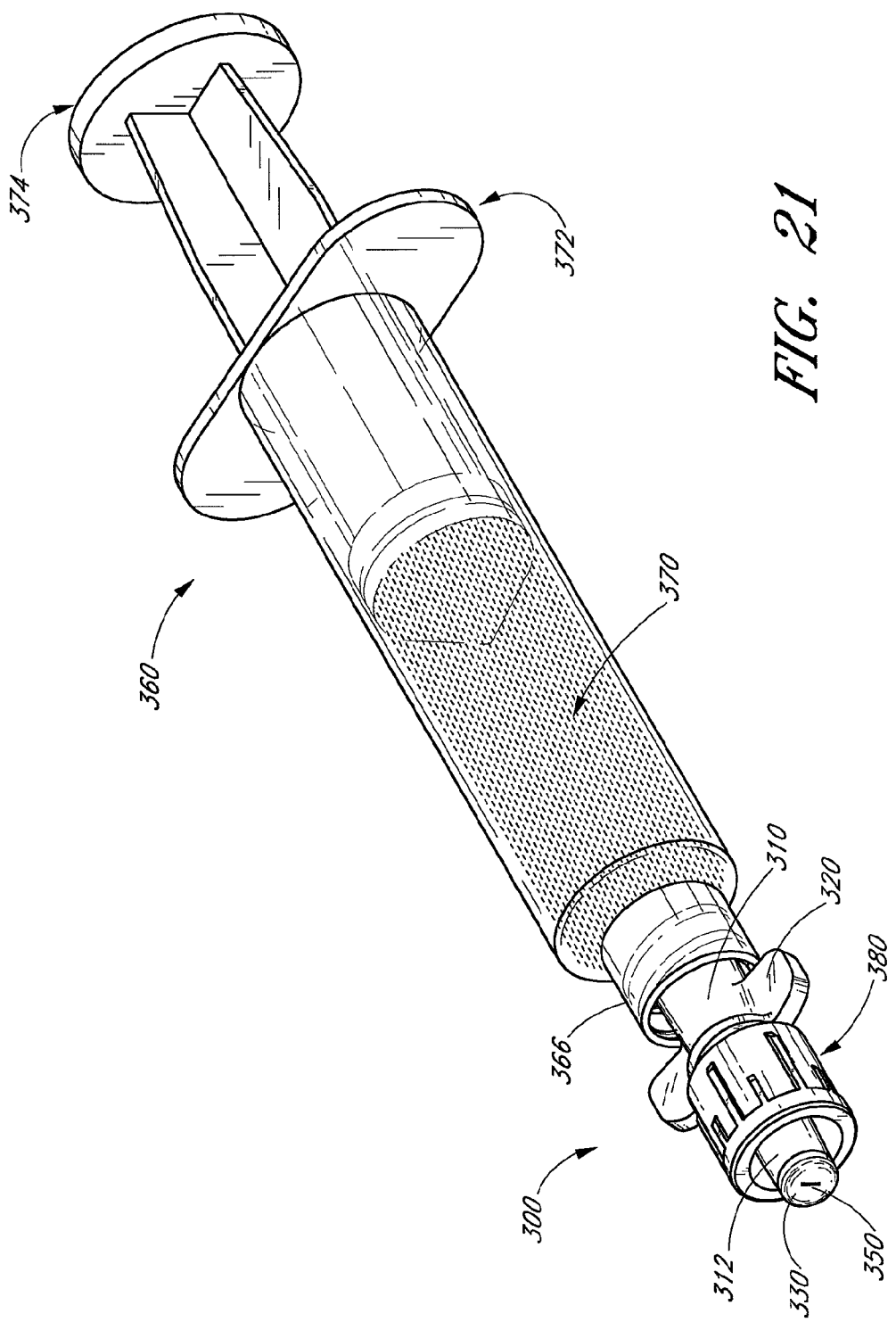
FIG. 21 is a perspective view of another embodiment of a closeable male luer connector engaged with a syringe with a male luer tip.

Referring now to FIG. 21, the closeable male luer connector 300 is illustrated in another embodiment, wherein an internally threaded shroud 380 is disposed on the housing 310. The shroud 380 at least partially or entirely encircles the housing 310 at approximately the recessed portion 342 (visible in FIG. 18A). In some embodiments, the shroud 380 is not attached to the connector 300, and instead can rotate freely about the longitudinal axis of the connector 300. The raised portion 340 (visible in FIG. 18A) can inhibit the movement of the shroud 380 towards the luer tip 312 of the connector 300. Additionally, the manipulation portion 320 of the connector 300 can inhibit the movement of the shroud 380 towards the luer receiver 316. The shroud 380 can be threaded consistent with ANSI specifications for luer connectors. The shroud 380 can assist the luer tip 312 in forming a connection between the connector 300 and other components (not shown).

Figure 22A:
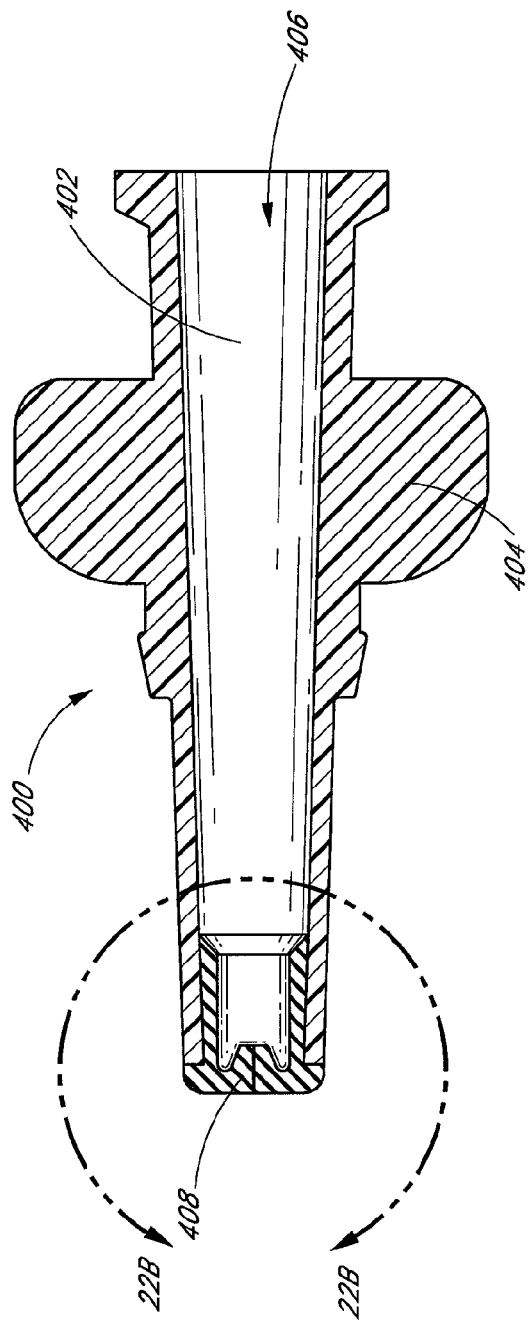
FIG. 22A is a cross-sectional view of another embodiment of a closeable male luer connector.

With reference now to FIG. 22A, the cross-section of a closeable male luer connector 400 with a continuously tapering internal passageway 402 is illustrated. The housing's 404 tapering internal passageway 402 permits for varied injection molding techniques of manufacture. For example, if the taper is wider at an end with a luer receiver 406, a molding pin can be tapered in a corresponding manner to closely fit against the wall of the internal passageway 402, producing a seal 408 that is shorter than the seal illustrated in FIG. 18B.

Figure 22B:
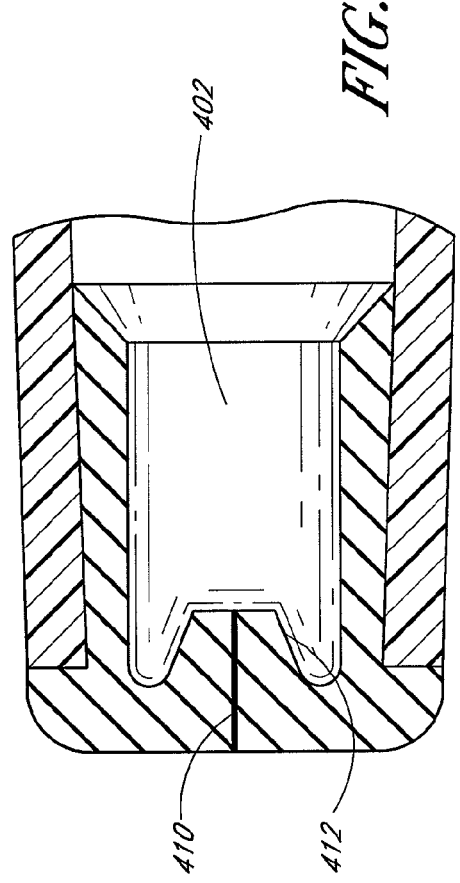
FIG. 22B is a detail of the cross-sectional view of the connector of FIG. 22A.

With reference to FIG. 22B, the seal 408 in the illustrated embodiment has a closing portion 412 similar to that of the closing portion 324 in FIG. 18B. In addition, the internal surface of the seal 408 can be adapted to increase resistance against permitting fluid from exiting the opening 410 when a fluid (not shown) in the internal passageway 402 exerts a pressure against the seal 408. The internal surface of the closing portion 412 can include slanted surfaces against which such fluid presses to urge the opening 410 more tightly closed.

Turning to FIG. 23A, a side view of another embodiment of the connector 400 of FIG. 22A is displayed. An internally threaded shroud 420 is disposed about the outer surface of the housing 404.

As can be seen in FIG. 23B, the housing 404 can have a raised portion 424 which inhibits axial movement of the shroud 420 toward the luer tip 416. The housing 404 can also have a manipulation portion 418 which extends radially outwardly from the longitudinal axis of the connector 400. The housing 404 also has an internal passageway 428 extending from the luer receiver 414 to the seal element 430. The manipulation portion 418 can inhibit movement of the shroud towards the luer receiver 414 of the connector 400. The manipulation portion can also be a convenient place for the user to place his or her fingers while turning the connector 400. Additionally, there can be a recessed portion 426 of the connector 400. The recessed portion 426 can be a portion of the connector 400 with a smaller outer diameter than the outer diameter of the raised portion 424 or the manipulation portion 418. The shroud 420 can be disposed on the connector 400 such that a narrow portion of the shroud 420 encircles the connector 400 about the recessed portion 426. The shroud 420 can be unaffixed to the housing 404 and thus free to rotate. The internal threads 422 of the shroud can conform to ANSI standards for luer connectors, allowing the shroud to assist the luer tip 416 in engaging the female connector of another component (not shown).

Figure 23C:
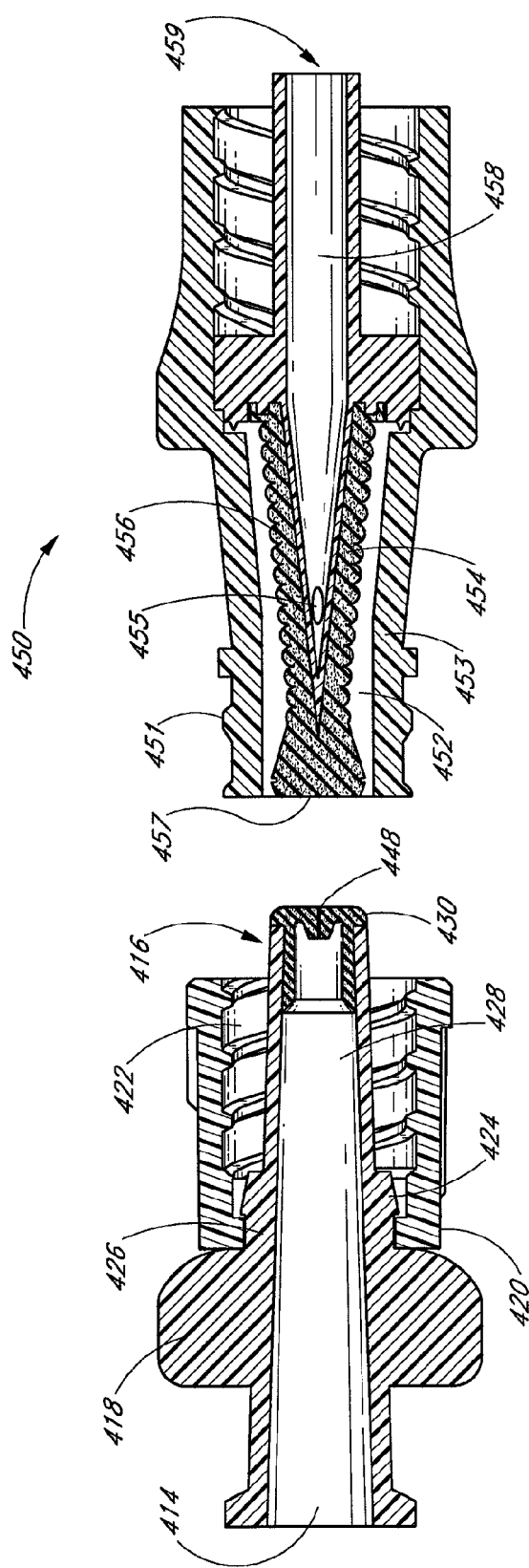
FIG. 23C is a perspective view an embodiment of a closeable male luer connector adjacent a closeable female connector. At this stage, fluid flow is impeded through the female luer connector.

FIG. 23C depicts the closeable male luer connector 400 of FIG. 23B in the proximity to a suitable female connector 450, such as a Clave® connector sold by ICU Medical, San Clemente, Calif. The female connector 450 is similar to that illustrated in FIG. 10.

Figure 23D:
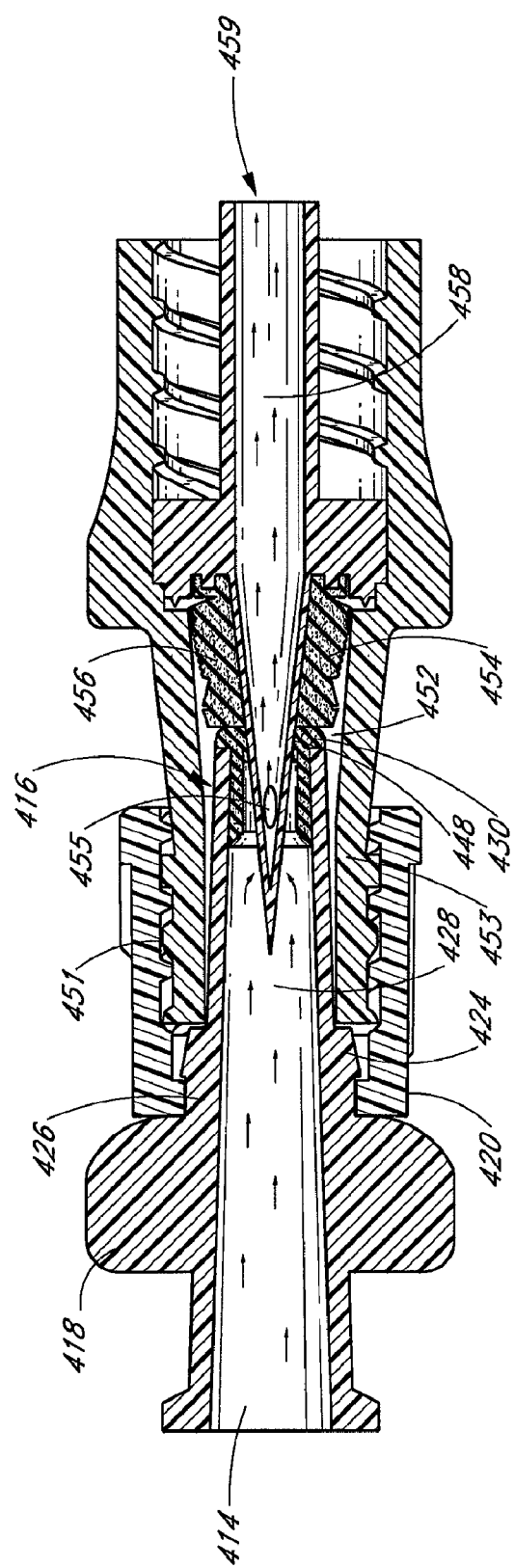
FIG. 23D is a perspective view of the components of FIG. 23C in engagement.

FIG. 23D illustrates an engagement between the male luer connector 400 and female connector 450. The internal threads of the shroud 420 can engage with a threaded region 451 of the female connector 450. The luer tip 416 of the male luer connector 400 can advance into the female connector 450 by compressing a compressible seal 454. As the male connector 400 advances, a stationary fluid conduit 456 of the female connector 450 can penetrate the opening 448 in the seal element 430 of male connector 400. The fluid conduit 456 can advance far enough into the male connector 400 that the holes 455 advance into the internal passageway 428 of the male connector 400. Once the holes 455 of the female connector 450 are disposed within the internal passageway 428 of the male connector, fluid can flow from the luer receiver 414 of the male connector 400 through the internal passageway 428 of the male connector 400 to the holes 455 of the fluid conduit 456 of the female connector 450. The fluid can then flow through the holes 455 and into a fluid conduit 458 of the female connector 450. Thus, fluid can flow from the first end of the male connector 400 to the distal end of the female connector 450 when the two are engaged. When the connectors 400, 450 are disengaged, the fluid conduit 456 withdraws from the internal passageway 428 and the seal element 430 closes, thereby inhibiting fluid flow through the male connector 400. Additionally, the compressible seal 411 of the female connector 450 returns to its original position, and inhibits flow through the holes 455 in the fluid conduit 456.

Figures 24A, 24B:
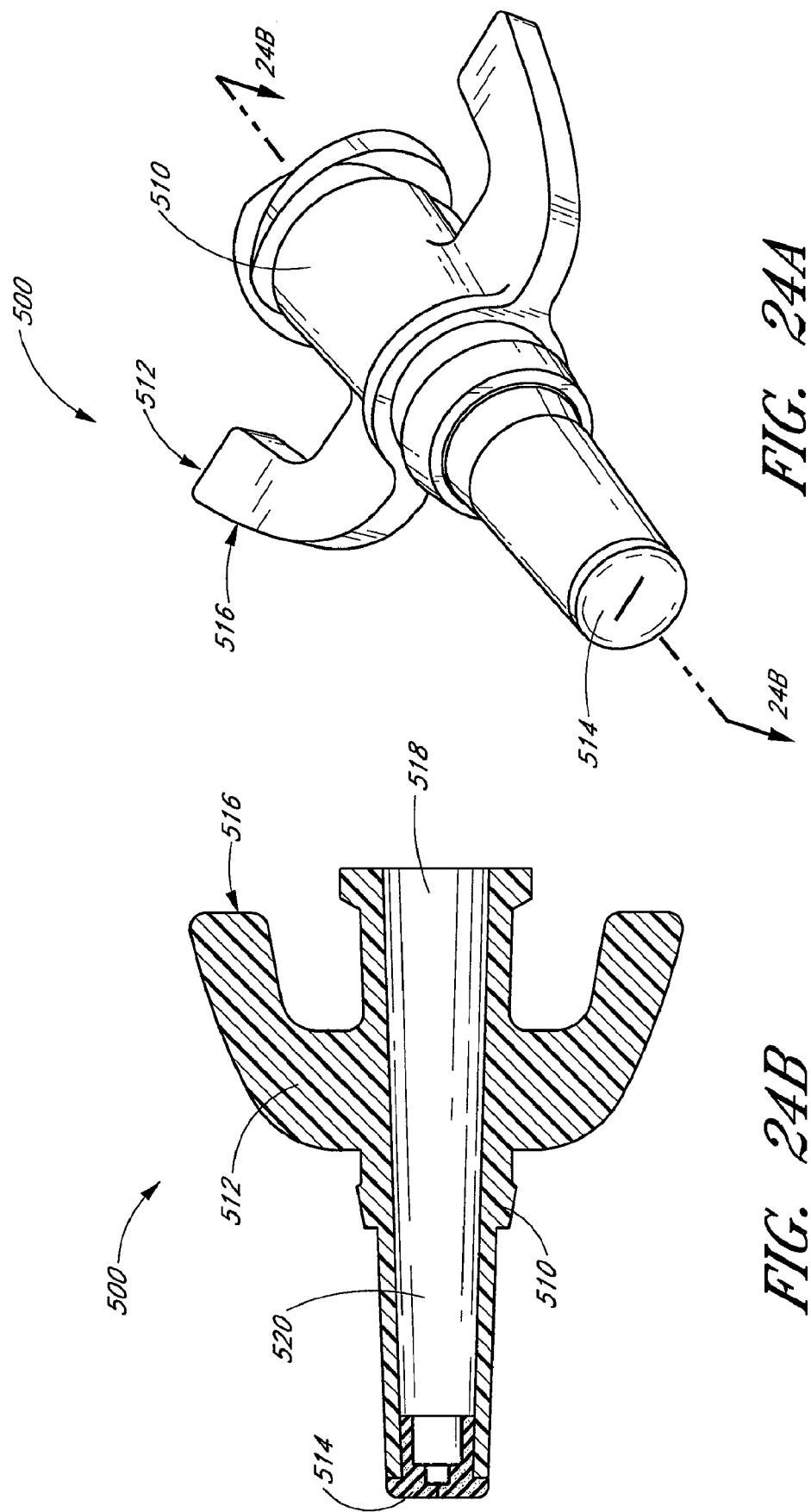
FIG. 24A is a perspective view of another embodiment of a closeable male luer connector.
FIG. 24B is a cross-sectional view of the connector of FIG. 24A.

With reference now to FIG. 24A, a closeable male luer connector 500 is displayed in a perspective view. The connector 500 has a housing 510 and a seal 514. The housing is comprised of a manipulation portion 512. In this exemplary illustration, the manipulation portion 512 includes wings 516. The wings 516 are adapted to provide a place for the user to grasp and rotate the housing 510 of the connector 500.

Referring now to FIG. 24B, the connector 500 of FIG. 23A is shown in cross-section. The wings 516 are shown as extending outward from the longitudinal axis of the connector 500 and towards the luer receiver 518 of the connector. The internal passageway 520 of the housing 510 has a continual taper, as described in the embodiment of the connector 400 in FIG. 22A.

Figure 25A:
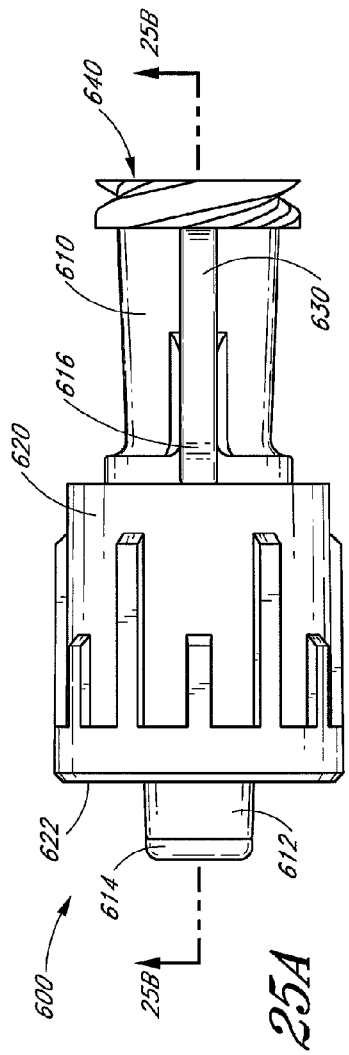
FIG. 25A is a side view of another embodiment of a closeable male luer connector with a shroud.

Turning to FIG. 25A, a side view of a closeable male luer connector 600 is illustrated. The connector 600 has a housing 610, a seal element 614, and a shroud 620. The housing comprises an internal passageway 640, a luer tip 612, and a manipulation portion 616. The manipulation portion can be constructed to comprise two wings 630, as described in FIG. 24A. The shroud can have internal threading 622, and such threading can be constructed to comply with ANSI specifications for luer connectors. The seal element 614 can be biased closed when not engaged.

Figure 25B:
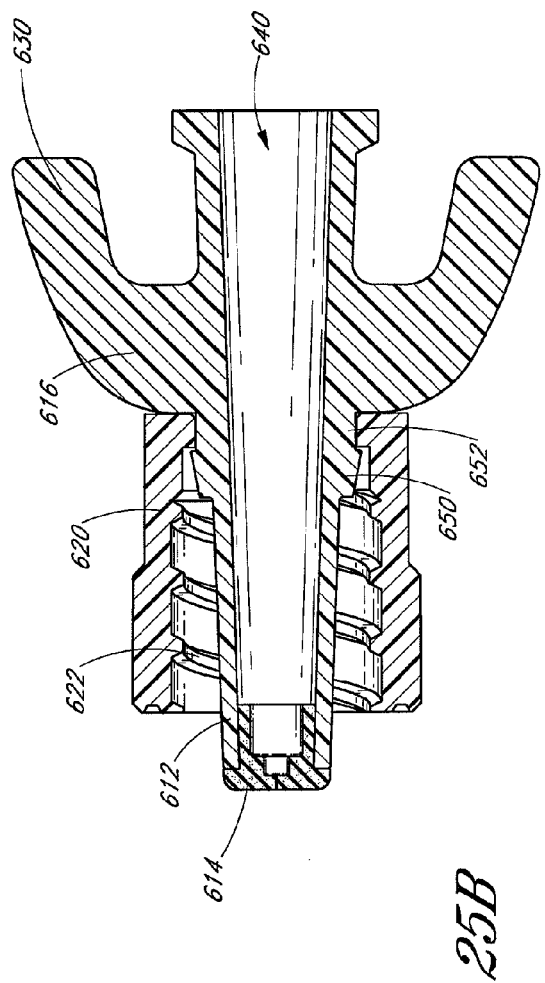
FIG. 25B is a cross-sectional view of the connector of FIG. 25A.

With reference now to FIG. 25B, a cross-sectional view of the connector 600 from FIG. 25A is displayed. The shroud 620 can encircle the housing 610 at a recessed portion 652 of the housing 610. A raised portion 650 can inhibit motion of the shroud 620 in the direction of the second end of the connector 600 while the manipulation portion 616 can inhibit motion of the shroud in the direction of the first end of the connector 600. The internal threading 622 of the shroud 620 can be used to engage other components (not shown) when used in conjunction with the luer tip 612. The continuously tapering internal passageway 640 has characteristics that assist in injection molding as discussed with regard to FIG. 22A.

Figure 26A:
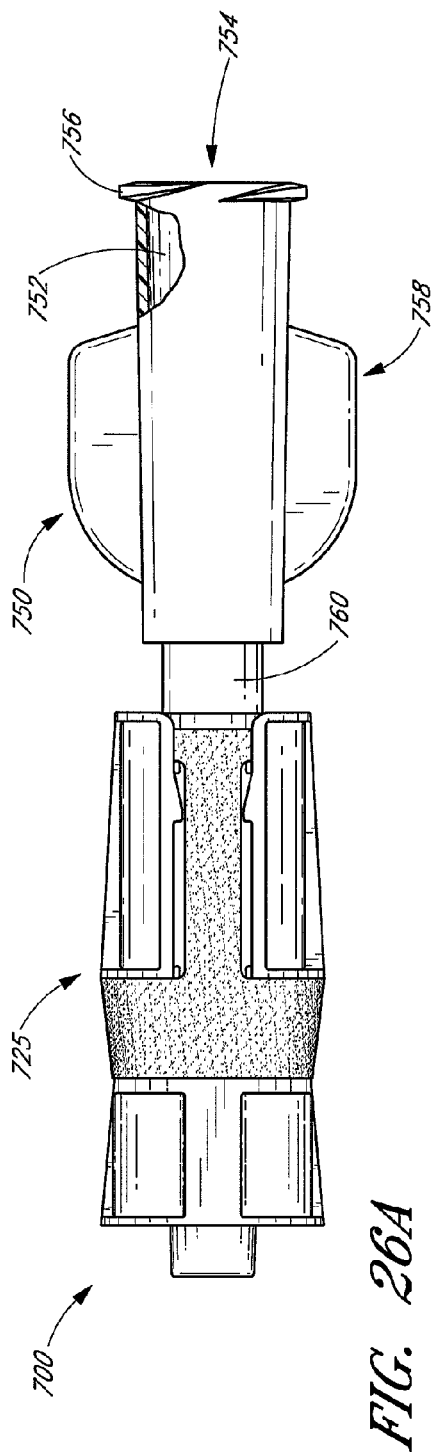
FIG. 26A is a perspective view of another embodiment of a closeable male luer with a flexibly connected female luer connector.

Referring to FIG. 26A, a perspective view of a closeable male luer assembly 725 comprising a closeable male luer 700 and a flexibly connected female luer connector 750 is displayed. The closeable male luer 700 can embody any number of the aspects and features described in this application. The female luer connector 750 is adapted to receive a standard male luer connector (not shown). The female luer connector 750 is located adjacent the male luer connector 700 and flexibly connected to it. The female luer connector 750 comprises an internal passageway 752, a luer receiver 754, and an engagement portion 756. The internal passageway 752 places the luer receiver 754 in fluid communication with an internal passageway of the closeable male luer connector 700. The closeable male luer connector 700 can be attached to the female luer connector 750 through a flexible segment 760. In some embodiments, such a segment 760 can include an accordion-like flexible portion of resilient material. In other embodiments, a straight, flexible material can be used. In other embodiments, both a flexible outer segment and a flexible tube can be used to connect the closeable male luer 700 with the female luer 750.

With continued reference to FIG. 26A, the flexible segment 752 permits the user to orient the female connector 750 of the assembly 725 in a different attitude than that of the closeable male luer connector 700. As an example, the closeable male luer 700 can remain stationary against a patient's arm while the female connector 750 is angled away from the arm to assist in easy connection with a syringe or other component (not shown). By flexibly connecting the closeable male luer 700 to the female luer connector 750, the moment generated by moving the female luer connector 750 is accepted at a point between the two components of the assembly 725 and is less likely to be transmitted to another component (not shown) attached to the closeable male luer connector 700. Such a component could include an I.V. site, where angling of the connection could result in harm to the patient. Moreover, the moment will be less likely to bend and/or dislodge the tip of the tube 40 from the interior of the lumen 28 (see, e.g., FIG. 28).

Figure 26B:
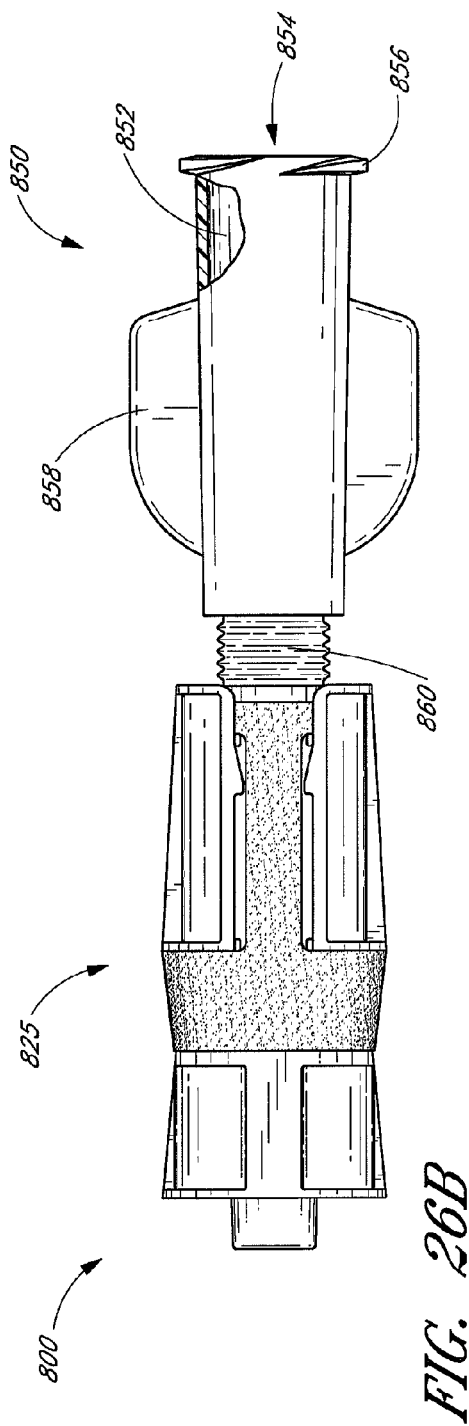
FIG. 26B is a perspective view of another embodiment of a closeable male luer with a flexibly connected female luer connector.

FIG. 26B illustrates another embodiment of a closeable male luer assembly 800 comprising a closeable male luer connector 825 and a flexibly connected female luer connector 850. The connectors 825, 850 and their components are similar in many respects to the embodiment depicted in FIG. 26 and can embody any number of the aspects and features described above. The closeable male luer connector 825 and the female luer connector 850 are flexibly connected by a connecting member 860. The connecting member 860 places the connectors 825, 850 in fluid communication. The connecting member 860 illustrated here comprises an accordion-shaped plastic conduit. The connecting member 860 is configured to permit the closeable male luer connector 825 and the female luer connector 850 to be positioned at different angular orientations. By way of example, the closeable male luer connector 825 can remain stationary while the female luer connector 850 can be positioned at an angle to the closeable male luer connector 825. In another example, the female luer connector 850 can remain stationary while the closeable male luer connector can be positioned at an angle to the female luer connector 850. In yet another example, the closeable male luer connector 825 and the female luer connector 850 can both be placed at an angle.

As described above, some medications, including those used during chemotherapy, can be harmful through certain forms of exposure to a patient. For example, exposure to the skin can sometimes result in a chemical burn. Inhalation of aerosolized forms of some medications can be harmful. Thus, control over the containment of the medication is highly desirable.

At present, some potentially harmful medications are distributed in sealed vials. The medication is removed from the vial by inserting a needle, and drawing the medication into a syringe. The needle is then withdrawn from the vial and the medication can be dispensed. However, by inserting the needle into the medication for drawing into the syringe, medication is disposed on the outside of the needle, which can inadvertently come in contact with the skin and cause harm. Alternatively, an injector which penetrates the vial with a withdrawal mechanism can be used. In such an injector, the medication is drawn through the mechanism and passed directly to a needle for injection without the additional step of withdrawing the mechanism from the vial. Even if such an injector is used, there is still the possibility of latent medication remaining on the needle used to inject the medication, or on the mechanism after the vial is decoupled.

Additionally, some medications can be distributed by attaching a needle to a syringe with the medication located therein. The engaged syringe with medication and needle is sterilized and placed into a vacuum-sealable container. The container is then evacuated and sealed. This type of arrangement can result in the draw of medication out through the syringe when the container is evacuated. While in the sealed container, the medication may aerosolize or coat the outer surface of the components.

Additionally, when the ambient atmospheric pressure of the treatment location is different, particularly lesser, than that of the internal pressure of the medication within a container, there is the possibility that an uncontrolled spray of the medication occurs when fluid communication between the medication and the ambient atmosphere occurs. For example, medication may escape when a vial with a greater internal pressure than the ambient atmosphere is penetrated by a needle for drawing the medication into a syringe. Alternatively, medication may escape when the needle is withdrawn from the vial seal before the vial seal completely closes.

With a closeable male luer, flow of the medication out of a syringe with a needle is inhibited, except during desired application. For example, in some embodiments, a syringe with a closeable male luer connected will not leak medication when packaged for shipment, even if the package is vacuum-sealed. Once the package is opened, the male luer connector can be engaged with a female luer connector of an IV tube, for example, and the medication dispensed only when the connection is engaged. Following flow of the medication from the syringe through the engaged connectors and into the IV tube, the male luer connector can be disengaged from the female luer connector. As described above, the male luer connector can close on disengagement, preventing excess flow through the connector. When a closeable female luer connector, such as a Clave® connector sold by ICU Medical, San Clemente, Calif., is used, flow is inhibited from exiting the female connector as well.

Additionally, a syringe with a closeable male luer can be engaged with a needle as described above. Flow through the needle can thus be controlled by proper use of the closeable male luer connector.

Medication can also be disposed within a syringe with an integrally formed, and/or permanently attached, closeable male luer.

Thus, direct exposure of the dangerous medications described can be essentially limited to the highly controlled environments where the medications are produced and contained. Such medications can be placed in a syringe with a closeable male luer connector prior to distribution for use, minimizing the risk of inadvertent exposure of the medication during use of the medication.

Any features of the embodiments shown and/or described in the figures that have not been expressly described in this text, such as distances, proportions of components, etc. are also intended to form part of this disclosure. Additionally, although this invention has been disclosed in the context of various embodiments, features, aspects, and examples, it will be understood by those skilled in the art that the present invention extends beyond the specifically disclosed embodiments to other alternative embodiments and/or uses of the invention and obvious modifications and equivalents thereof. Accordingly, it should be understood that various features and aspects of the disclosed embodiments can be combined with, or substituted for, one another in order to perform varying modes of the disclosed inventions. Thus, it is intended that the scope of the present invention herein disclosed should not be limited by the particular disclosed embodiments described above, but should be determined only by a proper reading of the claims.

What is claimed is:

1. A luer connector, comprising:
    a housing having a hollow bore having a first end, a second end, and a male luer tip with a tapering interior surface;
    a rigid valve member configured to at least partially extend through the housing, the valve member comprising:
        a first open end;
        a second closed end;
        a passageway within the valve member;
        at least one opening near the closed end of the valve member extending outwardly from the passageway through the valve member;
        at least one strut attached to the valve member, at least a portion of the strut extending substantially parallel to the central axis of the valve member; and
    a resilient retaining member configured to couple the valve member and the housing;
    wherein:
        the first open end of the valve member extends past a first end of the housing in a direction away from the closed end of the valve member such that at least a portion of the first open end of the valve member is positioned outside of the housing; and
        the valve member is manually movable relative to the housing between an open position and a closed position.

2. The connector of claim 1, wherein the valve member is openable by moving the open end of the valve member away from the first end of the housing, thereby allowing fluid to flow through the passageway within the valve member.

3. The connector of claim 2, wherein moving the open end of the valve member away from the first end of the housing moves the closed end of the valve member away from the second end of the housing, thereby allowing fluid to flow through the passageway within the valve member.

4. The connector of claim 1, wherein the valve member is openable by moving a male luer tip of a medical implement engaged with the open end of the valve member away from the first end of the housing, thereby moving the valve member to an open position and allowing fluid to flow through the passageway within the valve member.

5. The connector of claim 1, wherein the rigid valve member comprises an outwardly extending flange near the second end of the valve adapted to seal the hollow bore at the second end of the housing when placed in contact with a tapering interior surface of the housing.

6. The connector of claim 1, further comprising screw threads or other external engaging features projecting from an outside surface of the first open end of the valve member.

7. The connector of claim 1, wherein the valve member is manually openable to prime the luer connector.

8. The connector of claim 1, further comprising a sealing element disposed within the housing configured to inhibit fluid communication through the hollow bore of the housing between an interior of the male luer tip of the housing and the first end of the housing.

9. The connector of claim 8, wherein the sealing element has a body portion, at least one ring portion generally coaxially aligned with the body portion, and at least one protrusion extending from an outside wall of the body portion.

10. The connector of claim 9, wherein the sealing element is configured such that the ring portion is positioned at an end portion of the body portion.

11. The connector of claim 1, wherein the resilient member is configured to bias the valve member toward the second end of the housing while permitting the valve member to displace toward the first end of the housing when an opening force is applied to the luer connector.

12. The connector of claim 11, wherein the force is applied to either the second closed end of the valve member or the at least one strut attached to the valve member.

13. The connector of claim 11, wherein the force is applied to the first open end of the valve member.

14. The connector of claim 1, wherein the resilient member has at least two interconnected rings interconnected by at least one elastic member.

15. The connector of claim 14, wherein at least one of the rings is supported on the outside of the housing and at least one of the rings is supported by the valve member.

16. The connector of claim 1, wherein one or more depressions are formed in an outside surface of the housing, the depressions being sized and configured to assist a user in grasping and/or twisting the housing with his or her fingers.

17. The connector of claim 1, comprising a section of tubing attached to the open end of the valve member.

18. A method of opening a valve member in a luer connector having a male luer tip, comprising:
grasping a housing having a first end and a second end, wherein the male luer tip has a hollow bore axially therethrough and is positioned at or near the second end of the housing;
connecting a medical implement to an open end portion of the valve member, the valve member being supported partially within the housing such that the open end portion of the valve member extends past the first end of the housing so as to be positioned outside of the housing and a first closed end of the valve member extends into an inner portion of the male luer tip; and
opening the valve member to permit fluid to flow through a passageway extending through the valve member and through the male luer tip by moving the valve member away from the second end of the housing so that the closed end of the valve member moves away from an opening in the end of the male luer tip.

19. The method of opening a valve member in a luer connector of claim 18, wherein moving the valve member away from the second end of the housing comprises pulling on the open end portion of the valve member so as to manually move the open end portion of the valve member away from the first and second ends of the housing.

20. The method of opening a valve member in a luer connector of claim 18, wherein moving the valve member away from the second end of the housing comprises pushing at least one strut attached to the valve member toward the first end of the housing.

21. The method of opening a valve member in a luer connector of claim 18, wherein moving the valve member away from the second end of the housing comprises pushing the closed end of the valve member toward the first end of the housing.

22. The method of opening a valve member in a luer connector of claim 18, comprising threadingly connecting a medical implement to the open end portion of the valve member.

23. The method of opening a valve member in a luer connector of claim 22, wherein moving the valve member away from the second end of the housing comprises moving the medical implement threadingly connected to the open end portion of the valve member away from the first and second ends of the housing.

24. The method of opening a valve member in a luer connector of claim 18, wherein moving the open end of the valve member away from the first end of the housing moves the closed end of the valve member away from the second end of the housing, thereby allowing fluid to flow through the passageway within the valve member.

25. The method of opening a valve member in a luer connector of claim 18, wherein the valve member is openable by moving a male luer tip of a medical implement engaged with the open end of the valve member away from the first end of the housing, thereby moving the valve member to an open position and allowing fluid to flow through the passageway within the valve member.

26. The method of opening a valve member in a luer connector of claim 18, wherein the rigid valve member comprises an outwardly extending flange near the closed end thereof adapted to seal the hollow bore at the second end of the housing when the valve member is in a closed position.

27. The method of opening a valve member in a luer connector of claim 18, wherein the luer connector comprises screw threads or other external engaging features projecting from an outside surface of the first open end of the valve member.

28. The method of opening a valve member in a luer connector of claim 18, wherein the luer connector comprises a sealing element disposed within the housing configured to inhibit fluid communication through the hollow bore of the housing between an interior of the male luer tip of the housing and the first end of the housing.

29. The method of opening a valve member in a luer connector of claim 18, wherein the luer connector comprises a resilient member configured to bias the valve member toward the second end of the housing while permitting the valve member to displace toward the first end of the housing when an opening force is applied to the valve member.

30. The method of opening a valve member in a luer connector of claim 29, wherein the force is applied to the first open end of the valve member.

31. The method of opening a valve member in a luer connector of claim 29, wherein the resilient member has at least two interconnected rings interconnected by at least one elastic member.

32. The method of opening a valve member in a luer connector of claim 31, wherein at least one of the rings is supported on the outside of the housing and at least one of the rings is supported by the valve member.

33. The method of opening a valve member in a luer connector of claim 18, wherein one or more depressions are formed in an outside surface of the housing, the depressions being sized and configured to assist a user in grasping and/or twisting the housing with his or her fingers.

* * * * *